US009365903B2

(12) United States Patent
Michot et al.

(10) Patent No.: US 9,365,903 B2
(45) Date of Patent: Jun. 14, 2016

(54) COMPOSITIONS COMPRISING POLYNUCLEOTIDES FOR DETECTING LUNG CANCER

(71) Applicant: Cepheid, Sunnyvale, CA (US)

(72) Inventors: Bernard Michot, Pern (FR); Olivier Delfour, Caraman (FR)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 14/266,215

(22) Filed: Apr. 30, 2014

(65) Prior Publication Data

US 2014/0349869 A1 Nov. 27, 2014

Related U.S. Application Data

(63) Continuation of application No. 13/359,267, filed on Jan. 26, 2012, now abandoned.

(60) Provisional application No. 61/397,729, filed on Jan. 26, 2011, provisional application No. 61/436,399, filed on Jan. 26, 2011, provisional application No. 61/525,008, filed on Aug. 18, 2011.

(51) Int. Cl.
*C07H 21/02* (2006.01)
*C07H 21/04* (2006.01)
*C12Q 1/68* (2006.01)

(52) U.S. Cl.
CPC .......... *C12Q 1/6886* (2013.01); *C12Q 2600/118* (2013.01); *C12Q 2600/158* (2013.01); *C12Q 2600/16* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 6,582,908 B2 * | 6/2003 | Fodor et al. | 506/9 |
| 6,706,867 B1 * | 3/2004 | Lorenz | 536/23.1 |
| 7,709,616 B2 | 5/2010 | Bentwich et al. | |
| 2004/0081959 A9 * | 4/2004 | Reed et al. | 435/6 |
| 2005/0221370 A1 | 10/2005 | Hodge | |
| 2006/0068434 A1 | 3/2006 | Stoerker | |
| 2006/0134663 A1 | 6/2006 | Harkin et al. | |
| 2007/0050146 A1 | 3/2007 | Bentwich et al. | |
| 2007/0099196 A1 * | 5/2007 | Kauppinen et al. | 435/6 |
| 2007/0161004 A1 | 7/2007 | Brown et al. | |
| 2008/0026951 A1 | 1/2008 | Brown et al. | |
| 2008/0090245 A1 | 4/2008 | Jones et al. | |
| 2008/0182237 A1 | 7/2008 | Bentwich et al. | |
| 2008/0193943 A1 | 8/2008 | Murray | |
| 2008/0306017 A1 | 12/2008 | Croce et al. | |
| 2009/0143326 A1 * | 6/2009 | Obad et al. | 514/44 |
| 2010/0010072 A1 | 1/2010 | Dmitrovsky et al. | |
| 2010/0227325 A1 | 9/2010 | Vilanova et al. | |
| 2010/0233704 A1 | 9/2010 | Michot et al. | |
| 2010/0240049 A1 | 9/2010 | Svanholm Barrie et al. | |
| 2011/0015080 A1 | 1/2011 | Golub et al. | |
| 2011/0053158 A1 | 3/2011 | Mambo et al. | |
| 2012/0244530 A1 | 9/2012 | Michot et al. | |
| 2013/0084343 A1 | 4/2013 | Vilanova et al. | |
| 2013/0102487 A1 | 4/2013 | Gironella i Cos et al. | |
| 2013/0102488 A1 | 4/2013 | Barrie et al. | |
| 2013/0157886 A1 | 6/2013 | Michot et al. | |
| 2013/0177624 A1 * | 7/2013 | Corry et al. | 424/450 |
| 2014/0200153 A1 | 7/2014 | Michot et al. | |
| 2015/0051103 A1 | 2/2015 | Barrie et al. | |

FOREIGN PATENT DOCUMENTS

| | | |
|---|---|---|
| EP | 1783645 A1 | 5/2007 |
| JP | 2008-538494 A | 10/2008 |
| JP | 2010539959 A | 12/2010 |
| WO | 99/47706 A1 | 9/1999 |
| WO | 2005024061 A2 | 3/2005 |
| WO | WO 2005/024061 * | 3/2005 |
| WO | 2005/098029 A2 | 10/2005 |
| WO | 2006/069584 A2 | 7/2006 |
| WO | 2007/054520 A2 | 5/2007 |
| WO | 2007/073737 A1 | 7/2007 |
| WO | 2007/081196 A1 | 7/2007 |
| WO | 2007/081740 A2 | 7/2007 |
| WO | 2008/040355 A2 | 4/2008 |
| WO | 2008/046911 A2 | 4/2008 |
| WO | 2008/074328 A2 | 6/2008 |
| WO | 2010083464 A2 | 7/2010 |
| WO | 2010/139810 A1 | 12/2010 |
| WO | 2010139810 A1 | 12/2010 |
| WO | 2012/103355 A2 | 8/2012 |
| WO | 2013/040379 A1 | 3/2013 |
| WO | 2014/159073 A1 | 10/2014 |
| WO | 2014/164480 A1 | 10/2014 |

OTHER PUBLICATIONS

Rui et al. J Cellular and Molecular Medicine. Published online Nov. 9, 2009. vol. 14:206-214.*
Morin et al Genome Research. 2008. 18:610-621.*
Bissels et al. RNA. 2009. 15: 2375-2384.*
Beauchamp et al. Poster for Life Technologies, Nov. 8, 2003, available via url: <lifetechnologies.com/us/en/home/references/ambion-tech-support/posters/new-tools-for-mirna-and-sirna-analysis.html>.*
Pigati et al PLOS One. Oct. 20, 2010. 5(10):e13515.*
Ferretti et al Int J. Cancer. 2009. 124: 568-577.*
miRBase for has-mir-1246. available via url: <mirbase.org/cgi-bin/mirna_entry.pl?acc=MI0006381>, printed on Feb. 18, 2016.*
Brameier et al., "Human box C/D snoRNAs with mlRNA like functions: expanding the range of regulatory RNAs," Nucleic Acid Res., 2011, 39(2):675-686.
Burroughs et al., "Deep-sequencing of human argonaute-associated small RNAs provides insight into miRNA sorting and reveals argonaute association with RNA fragments of diverse origin," RNA Biol., 2011, 8:158-177.

(Continued)

*Primary Examiner* — Carla Myers
(74) *Attorney, Agent, or Firm* — McNeill Baur PLLC

(57) ABSTRACT

Methods of detecting lung cancer, such as non-small cell lung cancer, including squamous cell carcinoma and adenocarcinoma, are provided. Methods of detecting changes in the levels of one or more small RNAs associated with lung cancer are also provided. Compositions and kits are also provided.

10 Claims, 14 Drawing Sheets

(56) References Cited

OTHER PUBLICATIONS

Castoldi et al., "miChip: a microarray platform for expression profiling of microRNAs based on locked nucleic acid (LNA) oligonucleotide capture probes," Methods, 2007, 43(2):146-52.
Haussecker et al., "Human tRNA-derived small RNAs in the global regulation of RNA silencing," RNA, 2010, 16:673-695.
Lee et al., "A novel class of small RNAs: tRNA-derived RNA fragments (tRFs)," Genes Devel., 2009, 23:2639-2649.
Liu et al., "An oligonucleotide microchip for genome-wide microRNA profiling in human and mouse tissues," PNAS, 2004, 101(26):9740-4.
Miyoshi et al., "Many ways to generate microRNA-like small RNAs: non-canonical pathways for microRNA production," Mol Genet Genomics, 2010, 284(2):95-103.
NEB Catalog (1998/1999), pp. 121, 284 (3 pages).
NCBI GEO record describing Platform GPL7766, including full miRNA_LIST table accessed from http://www.ncbi.nlm.nih.gov/geo on Jul. 10, 2013 (14 pages).
Pederson, "Regulatory RNAs derived from transfer RNA?," RNA, 2010, 16:1865-1869.
Reese et al., "Identification of Novel MicroRNA-Like Molecules Generated from Herpesvirus and Host tRNA Transcripts," J Virol., 2010, 84(19):10344-10353.
Rothstein et al., "Chronic inhibition of superoxide dismutase produces apoptotic death of spinal neurons," PNAS, 1994, 91(10):4155-9.
Speicher et al., "Karyotyping human chromosomes by combinatorial multi-fluor FISH," Nat Gen., 1996, 12(4):368-75.
Yang & Lai, "Dicer-independent, Ago2-mediated microRNA biogenesis in vertebrates," Cell Cycle, 2010, 9:4455-4460.
File History for U.S. Appl. No. 13/658,276, filed Oct. 23, 2012.
File History for U.S. Appl. No. 13/684,874, filed Nov. 26, 2012.
File History for U.S. Appl. No. 13/359,267, filed Jan. 26, 2012.
File History for U.S. Appl. No. 13/617,789, filed Sep. 14, 2012.
Mazieres et al., "Alternative Processing of the U2 Small Nuclear RNA Produces a 19-22nt Fragment with Relevance for the Detection of Non-Small Cell Lung Cancer in Human Serum," PLoS One, 2013, 8(3):e60134 (13 pages).
Baraniskin et al., "Circulating U2 small nuclear RNA fragments as a novel diagnostic biomarker for pancreatic and colorectal adenocarcinoma," Int J Cancer, 2013, 132:E48-E57.
International Search Report and Written Opinion for PCT/US2014/021854, mailed Jul. 14, 2014, 13 pages.
Applied Biosystems, TaqMan MicroRNA Assays and Arrays Product Bulletin, 2011, 4 pages.
Boyd, Everything you wanted to know about small RNA but were afraid to ask, Laboratory Investigation (2008), 88:569-578.
Chang et al, miR-122, a Mammalian Liver-Specific microRNA, is Processed from her mRNA and May Downregulate the High Affinity Cationic Amino Acid Transporter CAT-1, RNA Biology (2004), 1(2):106-113.
Chen et al, Real-time quantification of microRNAs by stem-loop RT-PCR, Nucleic Acids Research (2005) 33(20): e179, 9 pages.
Dalmay, microRNAs and cancer, Journal of Internal Medicine (2008) 263(4):366-375.
Griffiths-Jones et al, miRBase: microRNA sequences, targets and gene nomenclature, Nucleic Acids Research (2006), 34:D140-D144.
Griffiths-Jones et al, miRBase: tools for microRNA genomics, Nucleic Acids Research (2008), 36:D154-D158.
Guo et al, Cross-Mapping Events in miRNAs Reveal Potential miRNA-Mimics and Evolutionary Implications, PLoS One (2011), 6: e20517, 7 pages.
Gusev et al, MicroRNA expression profiling in cancer from a bioinformatics prospective, Expert Review of Molecular Diagnostics (2007), 7(6): 787-792.
Hammond, microRNA detection comes of age, Nature Methods (2006), 3(1):12-13.
Heegaard et al, Circulating microRNA Expression Profiles in Early Stage Non-Small Cell Lung Cancer, International Journal of Cancer, doi:10.1002/ijc.26153, Aug. 26, 2011; 26 pages.
Kotake et al. Splicing factor SF3b as a target of the antitumor natural product pladeinolide, Nature Chem. Biol. (2007), 3(9):570-575.
Liu et al, Expression profiling of microRNA using oligo DNA arrays, Methods (2008), 44, 22-30.
Mora et al, Enzymatic microRNA detection in microtiter plates, BioTechniques (2006), 41(4):420-424.
Mora et al, High-sensitivity detection methods for low-abundance RNA species: applications for functional genomics research, Expert Review of Molecular Diagnostics (2007), 7(5), 775-785.
Nelson et al, Microarray-based, high-throughput gene expression profiling of microRNAs, Nature Methods (2004), 1 (2)155-161.
Persson et al, Identification of New MicroRNAs in Paired Normal and Tumor Breast Tissue Suggests a Dual Role for the ERBB2/Her2 Gene, Cancer Res. (2011), 71:78-86.
Varallyay et al, MicroRNA detection by northern blotting using locked nucleic acid probes, Nature Protocols (2008), 3:190-196.
Wark et al, Multiplexed Detection Methods for Profiling MicroRNA Expression in Biological Samples, Angew Chem Int Ed Engl (2008), 47:644-652 (Author manuscript, 18 pages).
Watahiki et al, MicroRNAs Associated with Metastatic Prostate Cancer, PLoS One (2011), 6(9):e24950, 13 pages.
Wilkinson, A rapid and convenient method for isolation of nuclear, cytoplasmic and total cellular RNA, Nucleic Acids Research (1988), 16(22):10934.
Zuker, Mfold web server for nucleic acid folding and hybridization prediction, Nucleic Acids Research (2003), 31:3406-3415.
Butnor, Avoiding Underdiagnosis, Overdiagnosis, and Misdiagnosis of Lung Carcinoma, Arch Pathol Lab Med (2008), 132:1118-1132.
Dziadziuszko et al, Advances in Genomic and Proteomic Studies of Non-Small-Cell Lung Cancer: Clinical and Translational Research Perspective, Clinical Lung Cancer (2008), 9(2):78-84.
Field et al, Lung Cancer Screening: the way forward, British Journal of Cancer (2008), 99:557-562.
Jay et al, miRNA Profiling for Diagnosis and Prognosis of Human Cancer, DNA and Cell Biology (2007), 26:293-300.
Lim et al, Mustering the micromanagers: microRNA expression has been profiled in a broad range of cell types, Nature Biotechnology (2007), 25(9):996-997.
Mascaux et al, Evolution of microRNAs expression during human brochial squamous carcinogenesis, ERJ Express (2008), dol: 10.1183/09031936.00084108; 23 pages.
Weiss et al, EGFR regulation by microRNA in lung cancer: correlation with clinical response and survival to gefitinib and EGFR expression in cell lines, Annals of Oncology (2008), 19:1053-159.
Zhang et al, microRNAs as oncogenes and tumor suppressors, Devel Biol. (2007), 302:1-12.
Baraniskin et al, Circulating U2 small nuclear RNA fragments as a novel diagnostic biomarker for pancreatic colorectal adenocarcinoma, Int J Cancer (2012), Accepted Article, doi:10.1002/ijc.27791, 57 pages.
International Search Report and Written Opinion mailed Sep. 7, 2010, for Application No. PCT/US2010/025446, filed Feb. 25, 2010; 17 pages.
International Search Report and Written Opinion mailed Jul. 11, 2012, for Application No. PCT/US2012/022756, filed Jan. 26, 2012; 21 pages.
SEQ ID No. 68404 from US2006/0134663, published Jun. 22, 2006; 2 pages.
SEQ ID No. 115101 from US2006/0134663, published Jun. 22, 2006; 1 page.
SEQ ID No. 2501 from US2007/0050146, published Mar. 1, 2007; 1 page.
Palmer et al., "Cell-type specific gene expression profiles of leukocytes in human peripheral blood," BMC Genomics, 2006, 7:115-129.
Coleman, "Of mouse and man—what is the value of the mouse in predicting gene expression in humans," DDT, 2003, 8(6):233-235.
Saetre et al., "From wild wolf to domestic dog: gene expression changes in the brain," Molecular Brain Research, 2004, 126:198-206.

(56) References Cited

OTHER PUBLICATIONS

Liu et al., "Coomparision of differentially expressed genes in T lymphocytes between human autoimmune disease and murine models of autoimmune disease," Clin Immunol, 2004, 112:225-230.

Dermer, "Another Anniversary for the War on Cancer," Biotechnology, 1994, 12:320.

Gao et al., MiR-21 overexpression in human primary squamous cell lung carcinoma is associate with poor patient prognosis,: J Cancer Res Clin Oncol, 2011, 137:557-566.

Fabbri et al., "MicroRNA-29 family reverts aberrant methylation in lung cancer by targeting DNA methyltransferases 3A and 3B," PNAS, 2007, 104(40)1 5805-15810.

Volinia et al., "A microRNA expression signature of human solid tumors defines cancer gene targets," PNAS, 2006, 103(7):2257-2261.

Volinia et al., "A microRNA expression signature of human solid tumors defines cancer gene targets, Supporting information" PNAS, 2006, doi:10.1073/pnas.0510565103, 24 pages.

Office Action mailed Jun. 25, 2012 for U.S. Appl. No. 12/713,072, 38 pages.

Calin et al., "Human microRNA genes are frequently located at fragile sites and genomic regions involved in cancers," Proc. Natl. Acad. Sci. USA, 2004, 101(9):2999-3004.

Extended European Search Report mailed Aug. 22, 2012 for EP Patent Application 10746849.8, 20 pages.

Extended European Search Report mailed Dec. 3, 2013, for EP Patent Application 13159760.1, 14 pages.

Grad et al., "Computational and Experimental Identification of *C. elegans* microRNAs," Molecular Cell, 2003, 11:1253-1263.

Japanese Notice of Reasons for Rejection mailed Aug. 5, 2014 for JP Patent Application 2011-551323, includes English translation, 8 pages.

Keller et al., "miRNAs in lung cancer—Studying complex fingerprints in patient's blood cells by microarray experiments," BMC Cancer, 2009. 9(1):353.

Mascaux et al, Evolution of microRNA expression during human brochial squamous carcinogenesis, Eur Respir J (2009), 33: 362-369.

McManus, M. "MicroRNAs and Cancer," Seminars in Cancer Biology, 2003, 13:253-258.

Qian et al., "MicroRNA expression profile of bronchioalveolar stem cells from mouse lung," Biochemical and Biophysical Research Communications, 2008, 377(2):668-673.

Raponi et al., "MicroRNA classifiers for predicting prognosis of squamous cell lung cancer," Cancer Res, 2009, 69 (14):5776-5783.

Takamizawa et al., "Reduced expression of the let-7 microRNAs in human lung cancers in association with shortened post operative survival," Cancer Res, 2004, 64(1):3753-3756.

Yanaihara et al., "Unique microRNA molecular profiles in lung cancer diagnosis and prognosis," Cancer Cell, 2006. 9:189-198.

Yu et al., "MicroRNA Signature Predicts Survival and Relapse in Lung Cancer," Cancer Cell, 2008, 13:48-57.

Gao et al., "Deregulated expression of miR-21, miR-143 and miR-181a in a non small cell lung cancer is related to clinicopathologic characteristics or patient prognosis," Biomedicine & Pharmacotherapy, 64, pp. 399-408 (2010).

Reid et al., "Circulating microRNAs:Association with disease and potential use as biomarkers," Critical Reviews in Oncology/Hematolgy, 80, pp. 193-208 (2011).

Extended European Search Report for EP application No. 12739259.5 dated Dec. 11, 2015 (9 pages).

\* cited by examiner

COMPOSITIONS COMPRISING POLYNUCLEOTIDES FOR DETECTING LUNG CANCER

This application is a continuation of U.S. application Ser. No. 13/359,267, filed Jan. 26, 2012, which claims priority to U.S. Provisional Application Nos. 61/397,729, filed Jan. 26, 2011; 61/436,399, filed Jan. 26, 2011; and 61/525,008, filed Aug. 18, 2011, which are incorporated by reference herein in their entireties for any purpose.

1. BACKGROUND

Lung cancer is the most common cause of cancer death in both men and women. Lung cancer is categorized into two types, small cell lung cancer ("SCLC") and non-small cell lung cancer ("NSCLC"). About 85% of lung cancer cases are categorized as NSCLC, which includes adenocarcinoma, squamous cell carcinoma, and adenosquamous cell carcinoma.

Lung cancer is difficult to diagnose in the early stages because it may manifest no outward symptoms. When symptoms do occur, they can vary depending on the type, location and spreading pattern of the cancer, and therefore, are not readily associated with cancer. Often, lung cancer is only correctly diagnosed when it has already metastasized.

Current techniques for diagnosing lung cancer include chest x-ray and/or computed tomography ("CT") scan. Diagnosis by one of these techniques is usually confirmed by a more invasive procedure, such as transthoracic needle biopsy or transbronchial biopsy, which may still result in misdiagnosis of lung cancer. (Butnor (2008) *Arch. Pathol. Lab. Med.* 132:1118-1132.)

Despite advances in treatment (e.g., by surgery, chemotherapy, radiation or a combination), the prognosis for lung cancer remains poor, with only 15% of patients surviving more than 5 years from the time of diagnosis. Of the most common NSCLCs, adenocarcinoma progresses more rapidly and therefore has a poorer prognosis than squamous-cell carcinoma, which takes several years to develop and is therefore more likely to be diagnosed in an early stage.

One proposal for reducing the mortality and morbidity of lung cancer is to institute regular screening of high-risk individuals, e.g., those who smoke or have smoked heavily for a certain period of time, in order to detect and treat lung cancer in asymptomatic individuals. In this way, early stage lung cancer can be eradicated by surgical resection, which is thought to be the only realistic option for a cure. (Field et al. (2008) *Br. J. Cancer* 99:557-562).

There remains a need for molecular markers in lung cancer, including markers for early stage lung cancer.

2. SUMMARY

In some embodiments, methods for detecting the presence of lung cancer in a subject are provided. In some embodiments, a method comprises detecting the level of at least one RNA selected from small U2, miR-720, miR-451, 13207, and 13750, in a sample from the subject. In some embodiments, a method comprises comparing the level of the at least one RNA selected from small U2, miR-720, miR-451, 13207, and 13750 in the sample to a normal level of the RNA. In some embodiments, detection of a level of small U2 that is greater than a normal level of the respective RNA indicates the presence of lung cancer in a subject. In some embodiments, detection of a level of at least one RNA selected from 13207, miR-720, miR-451, and 13750 that is less than a normal level of the respective RNA indicates the presence of lung cancer in the subject.

In some embodiments, a method of facilitating the diagnosis of lung cancer in a subject is provided. In some embodiments, a method comprises detecting the level of at least one RNA selected from small U2, miR-720, miR-451, 13207, and 13750, in a sample from the subject. In some embodiments, a method comprises communicating the results of the detection to a medical practitioner for the purpose of determining whether the subject has lung cancer.

In some embodiments, a method comprises detecting the level of small U2. In some embodiments, a method comprises detecting the level of 13750. In some embodiments, a method comprises detecting the level of miR-720. In some embodiments, a method comprises detecting the level of miR-451. In some embodiments, a method comprises detecting the levels of at least two RNAs selected from small U2, miR-720, miR-451, 13207, and 13750. In some embodiments, a method comprises detecting the levels of small U2 and 13750. In some embodiments, a method comprises detecting the levels of small U2 and miR-451. In some embodiments, a method comprises detecting the levels of small U2 and miR-720. In some embodiments, a method comprises detecting the levels of 13750 and miR-451. In some embodiments, a method comprises detecting the levels of 13750 and miR-720. In some embodiments, a method comprises detecting the levels of miR-451 and miR-720. In some embodiments, a method comprises detecting the levels of at least three RNAs selected from small U2, miR-720, miR-451, 13207, and 13750. In some embodiments, a method comprises detecting the levels of small U2, miR-720, and 13750. In some embodiments, a method comprises detecting the levels of small U2, miR-720, and miR-451. In some embodiments, a method comprises detecting the levels of small U2, miR-451, and 13750. In some embodiments, a method comprises detecting the levels of miR-720, miR-451, and 13750. In some embodiments, a method comprises detecting the levels of at least four RNAs selected from small U2, miR-720, miR-451, 13207, and 13750. In some embodiments, a method comprises detecting the levels of small U2, miR-720, miR-451, and 13750.

In some embodiments, a method for detecting the presence of lung cancer in a subject comprises detecting the level of small U2 in a sample from the subject, wherein detection of a level of small U2 that is greater than a normal level of small U2 indicates the presence of lung cancer in the subject. In some embodiments, a method further comprises detecting the level of at least one RNA selected from miR-720, miR-451, 13207, and 13750, wherein detection of a level of at least one RNA selected from miR-720, miR-451, 13207, and 13750 that is less than a normal level of the respective RNA, indicates the presence of lung cancer in the subject. In some embodiments, a method for detecting the presence of lung cancer in a subject comprises detecting the level of 13750 in a sample from the subject, wherein detection of a level of 13750 that is less than a normal level of 13750 indicates the presence of lung cancer in the subject. In some embodiments, a method further comprises detecting the level of at least one RNA selected from small U2, miR-720, miR-451, and 13207, wherein detection of a level of small U2 that is greater than a normal level of the respective RNA, or detection of a level of at least one RNA selected from miR-720, miR-451, and 13207 that is less than a normal level of the respective RNA, indicates the presence of lung cancer in the subject.

In some embodiments, a method for detecting the presence of lung cancer in a subject comprises obtaining a sample from the subject and providing the sample to a laboratory for detection of the level of at least one RNA selected from small U2, miR-720, miR-451, 13207, and 13750, in the sample. In some embodiments, a method comprises receiving from the laboratory a communication indicating the level of the at least one RNA. In some embodiments, detection of a level of small U2 that is greater than a normal level of the respective RNA indicates the presence of lung cancer in the subject. In some embodiments, detection of a level of at least one RNA selected from miR-720, miR-451, 13207, and 13750 that is less than a normal level of the respective RNA indicates the presence of lung cancer in the subject.

In some embodiments, detecting comprises hybridizing at least one polynucleotide comprising at least 8 contiguous nucleotides of a sequence selected from SEQ ID NOS: 42 to 51, 81, and 82 to RNA from the sample or cDNA reverse-transcribed from RNA from the sample, and detecting a complex comprising a polynucleotide and an RNA or cDNA selected from small U2, miR-720, miR-451, 13207, and 13750. In some embodiments, small U2 is selected from mature small U2, a mature small U2 isomir, pre-small U2, and combinations thereof. In some embodiments, miR-720 is selected from mature miR-720, a mature miR-720 isomir, pre-miR-720, and combinations thereof. In some embodiments, miR-451 is selected from mature miR-451, a mature miR-451 isomir, pre-miR-451, and combinations thereof. In some embodiments, 13207 is selected from mature 13207, a mature 13207 isomir, pre-13207, and combinations thereof. In some embodiments, 13750 is selected from mature 13750, a mature 13750 isomir, pre-13750, and combinations thereof. In some embodiments, small U2 has a sequence selected from SEQ ID NOS: 2 to 20. In some embodiments, miR-720 has a sequence selected from SEQ ID NOS: 21 and 23. In some embodiments, miR-451 has a sequence selected from SEQ ID NOS: 24 and 28 to 30. In some embodiments, 13207 has the sequence of SEQ ID NO: 34. In some embodiments, 13750 has a sequence selected from SEQ ID NOs: 35 and 38 to 41.

In some embodiments, the sample is selected from a tissue sample and a bodily fluid. In some embodiments, a tissue sample is a lung tissue sample. In some embodiments, the lung tissue sample comprises lung cancer cells. In some embodiments, the bodily fluid is selected from blood, urine, sputum, saliva, mucus, and semen. In some embodiments, the sample is a blood sample. In some embodiments, the blood sample is a serum sample. In some embodiments, the blood sample is a plasma sample. In some embodiments, the lung cancer is early stage lung cancer. In some embodiments, the lung cancer is stage I lung cancer. In some embodiments, the detecting comprises quantitative RT-PCR.

In some embodiments, use of at least one RNA selected from small U2, miR-720, miR-451, 13207, and 13750, for detecting the presence of lung cancer, including small cell lung cancer and non-small cell lung cancer, in a subject is provided. In some embodiments, use of small U2 for detecting the presence of lung cancer in a subject is provided. In some embodiments, use of 13750 for detecting the presence of lung cancer in a subject is provided. In some embodiments, use of small U2 and 13750 for detecting the presence of lung cancer in a subject is provided. In some embodiments, use of small U2, miR-720, miR-451, and 13750 for detecting the presence of lung cancer in a subject is provided.

In some embodiments, use of at least one RNA selected from small U2, miR-720, miR-451, 13207, and 13750, for monitoring the response of a lung cancer patient to therapy is provided. In some embodiments, use of small U2 for monitoring the response of a lung cancer patient to therapy is provided. In some embodiments, use of 13750 for monitoring the response of a lung cancer patient to therapy is provided. In some embodiments, use of small U2 and 13750 for monitoring the response of a lung cancer patient to therapy is provided. In some embodiments, use of small U2, miR-720, and 13750 for monitoring the response of a lung cancer patient to therapy is provided. In some embodiments, use of small U2, miR-720, miR-451, and 13750 for monitoring the response of a lung cancer patient to therapy is provided. In the monitoring to therapy, preferably a blood sample, such as serum, is used. In the monitoring of therapy, the levels of small U2, miR-720, miR-451, 13207, and 13750, measured individually or collectively, are assessed against their baseline levels determined at the initiation of therapy. In some embodiments, changes from the baseline levels indicate response to therapy where the levels for the particular RNA remain the same, or for small U2, the level decreases, or for miR-720, miR-451, 13207, or 13750, the levels increase. In some embodiments, changes from the baseline levels indicate resistance to therapy where for small U2, the level increases, or for miR-720, miR-451, 13207, or 13750, the levels decrease.

In some embodiments, uses of at least one, at least two, at least three, at least four, or at least five RNAs selected from small U2, miR-720, miR-451, 13207, and 13750 for detecting the presence of lung cancer (of any stage), early stage lung cancer, or stage I lung cancer in a subject are provided. In some embodiments, uses of small U2 for detecting the presence of lung cancer, early stage lung cancer, or stage I lung cancer in a subject are provided. In some embodiments, uses of 13750 for detecting the presence of lung cancer, early stage lung cancer, or stage I lung cancer in a subject are provided. In some embodiments, uses of small U2 and 13750 for detecting the presence of lung cancer, early stage lung cancer, or stage I lung cancer in a subject are provided. In some embodiments, uses of small U2 and miR-720 for detecting the presence of lung cancer, early stage lung cancer, or stage I lung cancer in a subject are provided. In some embodiments, uses of small U2 and miR-451 for detecting the presence of lung cancer, early stage lung cancer, or stage I lung cancer in a subject are provided. In some embodiments, uses of 13750 and miR-720 for detecting the presence of lung cancer, early stage lung cancer, or stage I lung cancer in a subject are provided. In some embodiments, uses of 13750 and miR-451 for detecting the presence of lung cancer, early stage lung cancer, or stage I lung cancer in a subject are provided. In some embodiments, uses of small U2, miR-720, miR-451, and 13750 for detecting the presence of lung cancer, early stage lung cancer, or stage I lung cancer in a subject are provided.

In some embodiments, compositions are provided. In some embodiments, a composition comprises at least one target-specific probe. In some embodiments, a composition comprises at least one target-specific primer. In some embodiments, the target is selected from U2, miR-720, miR-451, 13207, and 13750. In some embodiments, a composition comprises at least one, at least two, at least three, or at least four oligonucleotides that comprise at least eight contiguous nucleotides that are complementary to an RNA selected from small U2, miR-720, miR-451, 13207, and 13750. In some embodiments, each oligonucleotide comprises at least eight contiguous nucleotides that are complementary to a different RNA. In some embodiments, a composition comprises at least one, at least two, at least three, or at least four oligonucleotides that comprise at least eight contiguous nucleotides that are complementary to a cDNA reverse-transcribed from an RNA selected from small U2, miR-720, miR-451, 13207, and 13750. In some embodiments, each oligonucleotide comprises at least eight contiguous nucleotides that are complementary to a different cDNA. In some embodiments, the at least one oligonucleotide comprises 8 to 50 nucleotides, 8 to 45, nucleotides, 8 to 40 nucleotides, 8 to 35 nucleotides, 8 to 30 nucleotides, or 8 to 25 nucleotides. In some embodiments, kits are provided. In some embodiments, a kit comprises a composition described herein. In some embodiments, a kit comprises one or more additional components. In some embodiments, a kit comprises at least one additional component selected from an enzyme, dNTPs, and a buffer. In some embodiments, the enzyme is selected from reverse transcriptase and a heat stable polymerase.

In any of the embodiments described herein, miR-720 may be mature miR-720, miR-451 may be mature miR-451, 13207 may be mature 13207, and 13750 may be mature 13750.

Further embodiments and details of the inventions are described below.

3. BRIEF DESCRIPTION OF THE FIGURES

4. DETAILED DESCRIPTION

4.1. Detecting Lung Cancer

4.1.1. General Methods

Figure 1:
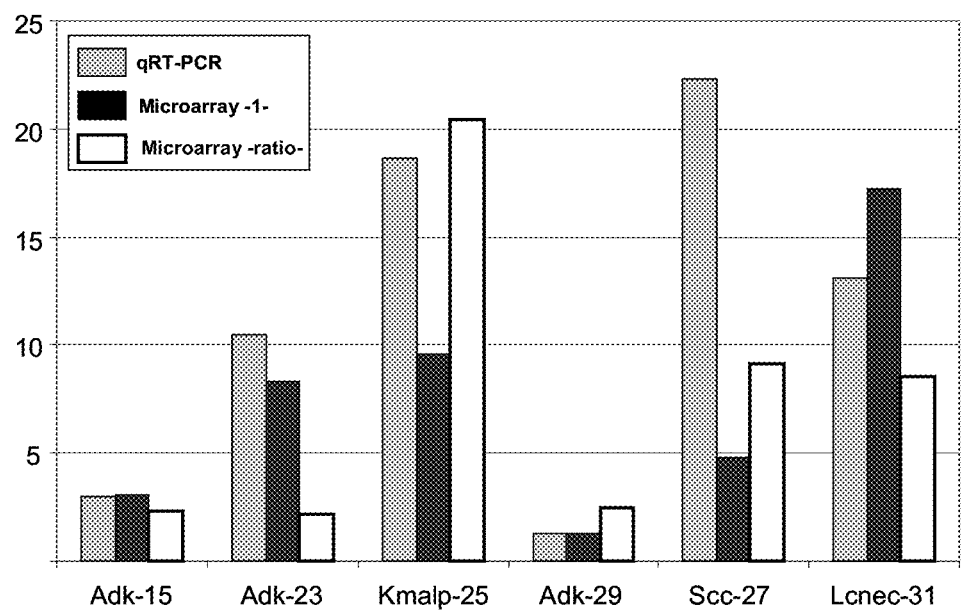
FIG. 1 shows a plot of small U2 levels in various primary lung tumors, determined by qRT-PCR or microarray, as described in Example 2.

Methods for detecting human lung cancer are provided. In some embodiments, methods for detecting early stage lung cancer are provided. In some embodiments, methods of detecting stage I lung cancer are provided. In some embodiments, methods for detecting early stage lung cancer that is likely to progress are provided.

In some embodiments, a method of detecting lung cancer comprises detecting at least one, at least two, at least three, or at least four RNAs selected from small U2, miR-720, miR-451, 13207, and 13750. In some embodiments, a method of detecting lung cancer comprises detecting at least one, at least two, or at least three RNAs selected from small U2, miR-720, miR-451, and 13750. In some embodiments, a method of detecting lung cancer comprises detecting small U2. In some embodiments, a method of detecting lung cancer comprises detecting small U2 and at least one additional RNA selected from miR-720, miR-451, and 13750. In some embodiments, a method of detecting lung cancer comprises detecting small U2 and miR-451. In some embodiments, a method of detecting lung cancer comprises detecting small U2 and miR-720. In some embodiments, a method of detecting lung cancer comprises detecting small U2 and 13750. In some embodiments, a method of detecting lung cancer comprises detecting small U2 and at least two additional RNAs selected from miR-720, miR-451, and 13750. In some embodiments, a method of detecting lung cancer comprises detecting 13750. In some embodiments, a method of detecting lung cancer comprises detecting 13750 and at least one additional RNA selected from miR-720, miR-451, and small U2. In some embodiments, a method of detecting lung cancer comprises detecting 13750 and miR-451. In some embodiments, a method of detecting lung cancer comprises detecting 13750 and miR-720. In some embodiments, a method of detecting lung cancer comprises detecting small 13750 and at least two additional RNAs selected from miR-720, miR-451, and small U2. In some embodiments, a method of detecting lung cancer comprises detecting small U2, miR-720, miR-451, and 13750.

In some embodiments, the method comprises detecting an above-normal level of small U2. In some embodiments, the method comprises detecting an above-normal level of small U2 and a below-normal level of at least one, at least two, at least three, or at least four RNAs selected from miR-720, miR-451, 13207, and 13750. In some embodiments, the method comprises detecting an above-normal level of small U2 and a below-normal level of at least one, at least two, or at least three RNA selected from miR-720, miR-451, and 13750. In some embodiments, the method comprises detecting an above-normal level of small U2 and a below-normal level of miR-720. In some embodiments, the method comprises detecting an above-normal level of small U2 and a below-normal level of miR-451. In some embodiments, the method comprises detecting an above-normal level of small U2 and a below-normal level of 13750. In some embodiments, the method comprises detecting an above-normal level of small U2 and below-normal levels of miR-720 and miR-451. In some embodiments, the method comprises detecting an above-normal level of small U2 and below-normal levels of miR-720 and 13750. In some embodiments, the method comprises detecting an above-normal level of small U2 and below-normal levels of miR-451 and 13750. In some embodiments, the method comprises detecting an above-normal level of small U2 and below-normal levels of miR-720, miR-451, and 13750.

In some embodiments, the method comprises detecting a below-normal level of 13750. In some embodiments, the method comprises detecting a below-normal level of 13750 and a below-normal level of at least one, at least two, or at least three RNAs selected from miR-720, miR-451, and 13207. In some embodiments, the method comprises detecting a below-normal level of 13750 and a below-normal level of at least one or at least two RNAs selected from miR-720 and miR-451. In some embodiments, the method comprises detecting below-normal levels of 13750 and miR-720. In some embodiments, the method comprises detecting below-normal levels of 13750 and miR-451. In some embodiments, the method comprises detecting below-normal levels of 13750, miR-451, and miR-720.

In some embodiments, the level of one or more RNAs is determined in serum. In some embodiments, the method further comprises detecting an above-normal level of at least one additional target RNA. In some embodiments, the method further comprises detecting a below-normal level of at least one additional target RNA. In some embodiments, the method comprises detecting mature microRNA and pre-microRNA. In some embodiments, the method comprises detecting mature microRNA.

In some embodiments, in any of the methods described herein, miR-720 is mature miR-720. In some embodiments, in any of the methods described herein, miR-451 is mature miR-451. In some embodiments, in any of the methods described herein, 13207 is mature 13207. In some embodiments, in any of the methods described herein, 13750 is mature 13750.

The present inventors initially set out to identify microRNAs that are present and higher or lower levels in serum from lung cancer patients, relative to serum from healthy individuals. Upon sequencing small RNAs from serum of lung cancer patients, however, it was found that one of the small RNAs present at higher levels has a sequence identical to a sequence found in U2 snRNA, and differs from microRNA miR-1290 by one nucleotide. For convenience, these small U2 RNAs were included in the definition of "miR-1290 species" in U.S. Provisional Application No. 61/397,729, filed Jan. 26, 2011. In the interest of more accurately identifying the origin of these small RNAs, they have been renamed "small U2 RNAs" in the present filing. Although the small RNAs have been renamed herein, it is evident from U.S. Provisional Application No. 61/397,729 that it was appreciated by the inventors at the time that application was filed that these particular RNAs, which are different from miR-1290, were present at increased levels in serum from lung cancer patients. Further, miR-1290 does not appear to be elevated in either primary lung cancer tissue or serum from lung cancer patients. Thus, miR-1290 does not appear to be a marker for lung cancer.

In the sequences herein, "U" and "T" are used interchangeably, such that both letters indicate a uracil or thymine at that position. One skilled in the art will understand from the context and/or intended use whether a uracil or thymine is intended and/or should be used at that position in the sequence. For example, one skilled in the art would understand that native RNA molecules typically include uracil, while native DNA molecules typically include thymine. Thus, where a microRNA sequence includes "T", one skilled in the art would understand that that position in the native microRNA is a likely uracil.

As used herein, the terms "small U2" and "small U2 RNA" are used interchangeably and mean polynucleotides having between 12 and 40 contiguous nucleotides of the full-length U2 snRNA sequence:

```
                                              (SEQ ID NO: 1)
5'-AUCGCUUCUC GGCCUUUUGG CUAAGAUCAA GUGUAGUAUC

UGUUCUUAUC AGUUUAAUAU CUGAUACGUC CUCUAUCCGA

GGACAAUAUA UUAAAUGGAU UUUUGGAGCA GGGAGAUGGA

AUAGGAGCUU GCUCCGUCCA CUCCACGCAU CGACCUGGUA

UUGCAGUACC UCCAGGAACG GUGCACCC-3'
```

In some embodiments, a small U2 has between 15 and 35 contiguous nucleotides of the full-length U2 snRNA sequence. In some embodiments, a small U2 has between 18 and 30 contiguous nucleotides of the full-length U2 snRNA sequence. In some embodiments, small U2 RNAs are formed through processing of the U2 snRNA polynucleotide. The term "small U2" also includes any small U2 products of U2 snRNA after eventual post-transcriptional modification or editing.

In some embodiments, a small U2 RNA comprises a core sequence:

5'-UGGAUUUUUGGAGCAGGG-3' (SEQ ID NO: 2)

with 0 to 3 additional contiguous nucleotides from the U2 snRNA sequence on the 5' end, and 0 to 9 additional contiguous nucleotides from the U2 snRNA sequence on the 3' end.

Nonlimiting exemplary small U2 RNAs have the sequence:

```
                                              (SEQ ID NO: 3)
        5'-AAAUGGAUUUUUGGAGCAGGGAGAUGGAAU-3'

(SEQ ID NO: 4)
        5'-AAAUGGAUUUUUGGAGCAGGGAGAU-3'

(SEQ ID NO: 5)
        5'-AAAUGGAUUUUUGGAGCAGGGAGA-3'

(SEQ ID NO: 6)
        5'-AAAUGGAUUUUUGGAGCAGGGAG-3'

(SEQ ID NO: 7)
        5'-AAAUGGAUUUUUGGAGCAGGGA-3'
```

-continued

5'-AAAUGGAUUUUUGGAGCAGGG-3' (SEQ ID NO: 8)

5'-AAUGGAUUUUUGGAGCAGGGAGAU-3' (SEQ ID NO: 9)

5'-AAUGGAUUUUUGGAGCAGGGAGA-3' (SEQ ID NO: 10)

5'-AAUGGAUUUUUGGAGCAGGGAG-3' (SEQ ID NO: 11)

5'-AAUGGAUUUUUGGAGCAGGGA-3' (SEQ ID NO: 12)

5'-AUGGAUUUUUGGAGCAGGGAGAU-3' (SEQ ID NO: 13)

5'-AUGGAUUUUUGGAGCAGGGAGA-3' (SEQ ID NO: 14)

5'-AUGGAUUUUUGGAGCAGGGAG-3' (SEQ ID NO: 15)

5'-AUGGAUUUUUGGAGCAGGGA-3' (SEQ ID NO: 16)

5'-AUGGAUUUUUGGAGCAGGG-3' (SEQ ID NO: 17)

5'-UGGAUUUUUGGAGCAGGGAGA-3' (SEQ ID NO: 18)

5'-UGGAUUUUUGGAGCAGGGAG-3' (SEQ ID NO: 19)

5'-UGGAUUUUUGGAGCAGGGA-3' (SEQ ID NO: 20)

As demonstrated in the Examples, small U2 was detected at elevated levels in certain lung cancer patients, using both microarrays and quantitative RT-PCT.

As used herein, the term "miR-720" includes pre-miR-720, mature miR-720, mature miR-720 isomirs, miR-720*, and any other RNAs formed through processing of the pre-miR-720, as well as any of products of pre-miR-720 after eventual post-transcriptional modification or editing. Mature miR-720 has the sequence:

5'-UCUCGCUGGGGCCUCCA-3'. (SEQ ID NO: 21)

Pre-miR-720, which is the pre-microRNA form of miR-720, has the sequence:

(SEQ ID NO: 22)
5'-CCGGAUCUCA CACGGUGGUG UUAAUAUCUC GCUGGGGCCU

CCAAAAUGUU GUGCCCAGGG GUGUUAGAGA AAACACCACA

CUUUGAGAUG AAUUAAGAGU CCUUUAUUAG-3'.

The pre-miR-720 has the following structure, in which the mature miR-720 sequence is shown in bold.

MiR-720* forms are derived from the strand opposite the mature miR-720 on the pre-miR-720. Another exemplary miR-720 has the sequence:

5'-AUCUCGCUGGGGCCUCCA-3'. (SEQ ID NO: 23)

As demonstrated in the Examples, at least mature miR-720 was detected at reduced levels in a large cohort of lung cancer patients, using, e.g., quantitative RT-PCT.

As used herein, the term "miR-451" includes pre-miR-451, mature miR-451, mature miR-451 isomirs, miR-451*, and any other RNAs formed through processing of the pre-miR-451, as well as any of products of pre-miR-451 after eventual post-transcriptional modification or editing. Mature miR-451 has the sequence:

5'-AAACCGUUACCAUUACUGAGUU-3'. (SEQ ID NO: 24)

Pre-miR-451, which is the pre-microRNA form of miR-451, has the sequence:

(SEQ ID NO: 25)
5'-CUUGGGAAUG GCAAGGAAAC CGUUACCAUU ACUGAGUUUA

GUAAUGGUAA UGGUUCUCUU GCUAUACCCA GA-3'.

The pre-miR-451 has the following structure, in which the mature miR-451 sequence is shown in bold.

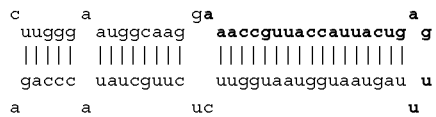

MiR-451* forms are derived from the strand opposite the mature miR-451 on the pre-miR-451, such as:

5'-UAAUGGUAAUGGUUCUCUUG- 3'; (SEQ ID NO: 26)
and

5'-UUUAGUAAUGGUAAUGGUUCU-3'. (SEQ ID NO: 27)

Other exemplary miR-451 RNAs have the sequences:

5'-AAACCGUUACCAUUACUGAGUUU-3'; (SEQ ID NO: 28)

5'-AAACCGUUACCAUUACUGAGU-3'; (SEQ ID NO: 29)
and

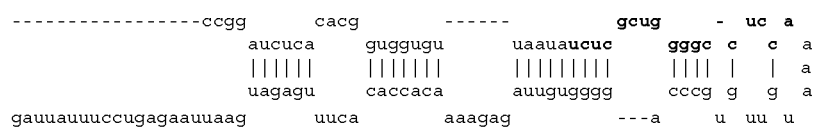

-continued (SEQ ID NO: 30)
5'-AAACCGUUACCAUUACUGAG-3'.

As demonstrated in the Examples, at least mature miR-451 was detected at decreased levels in primary tissue from certain lung cancer patients, and at reduced levels in a large cohort of lung cancer patients, using, e.g., quantitative RT-PCR.

As used herein, the term "13207" includes pre-13207, mature 13207, mature 13207 isomirs, 13207*, and any other RNAs formed through processing of the pre-13207, as well as any of products of pre-13207 after eventual post-transcriptional modification or editing. Mature 13207 (also referred to as "13207-R") has the sequence:

(SEQ ID NO: 31)
5'-UGUCUUUCCUUGUUGGAGCAGG-3'.

Pre-13207, which is the pre-microRNA form of 13207, has the sequence:

(SEQ ID NO: 32)
5'- GCCCCCCAAA AUGCUUCUGU ACCCCUGCCC CAACAAGGAA

GGACAAGAGG UGUGAGCCAC ACACACGCCU GGCCUCCUGU

CUUUCCUUGU UGGAGCAGGG AUGUAGAAGC ACUUGCCGCA G -3'.

13207* forms are derived from the strand opposite the mature 13207 on the pre-13207, such as:

(SEQ ID NO: 33)
5'-TGCCCCAACAAGGAAGGACAAG-3';
and (SEQ ID NO: 34)
5'-TGCCCCAACAAGGAAGGACAAGA-3'.

Another example 13207 has the sequence:

(SEQ ID NO: 80)
5'-UCCUGUCUUUCCUUGUUGGAGC-3'

13207 represented by SEQ ID NO: 80 is deposited in MirBase as miR-5699. As demonstrated in the Examples, at least mature 13207 was detected at reduced levels in certain lung cancer patients, using, e.g., quantitative RT-PCT.

As used herein, the term "13750" includes pre-13750, mature 13750, mature 13750 isomirs, 13750*, and any other RNAs formed through processing of the pre-13750, as well as any of products of pre-13750 after eventual post-transcriptional modification or editing. Mature 13750 (also referred to as "13750-L") has the sequence:

(SEQ ID NO: 35)
5'-TGTAGAGCAGGGAGCAGGAAGCT-3'.

Pre-13750, which is the pre-microRNA form of 13750, has the sequence:

(SEQ ID NO: 36)
5'-GGCCTGCGAGGGAGCTGTAGAGCAGGGAGCAGGAAGCTGTGTGTGTC

CAGCCCTGACCTGTCCTGTTCTGCCCCCAGCCCCTCACAGTGCT- 3'.

13750* forms (also referred to as "13750-R") are derived from the strand opposite the mature 13750 on the pre-13750, such as:

(SEQ ID NO: 37)
5'-GCCCTGACCTGTCCTGTTCTG-3';
and (SEQ ID NO: 79)
5'-GCCCTGACCTGTCCTGTTCT-3'.

Other exemplary mature 13750 RNAs have the sequences:

(SEQ ID NO: 38)
5'-TGTAGAGCAGGGAGCAGGAAGC-3';

(SEQ ID NO: 39)
5'-TGTAGAGCAGGGAGCAGGAAG-3';

(SEQ ID NO: 40)
5'-TGTAGAGCAGGGAGCAGGAA-3';
and (SEQ ID NO: 41)
5'-TGTAGAGCAGGGAGCAGGA-3'.

13750-L represented by SEQ ID NO: 35 is deposited in MirBase as miR-4732-5p and 13750-R represented by SEQ ID NO: 37 is deposited in MirBase as miR-4732-3p. As demonstrated in the Examples, at least mature 13750 was detected at reduced levels in certain lung cancer patients, using, e.g., quantitative RT-PCT.

In the present disclosure, "a sequence selected from" encompasses both "one sequence selected from" and "one or more sequences selected from." Thus, when "a sequence selected from" is used, it is to be understood that one, or more than one, of the listed sequences may be chosen.

As used here, a list such as "at least one RNA selected from small U2, miR-720, miR-451, 13207, and 13750" is intended to encompass "at least one RNA selected from: at least one small U2, at least one miR-720, at least one miR-451, at least one 13207, and at least one 13750," where small U2, miR-720, miR-451, 13207, and 13750 are defined as above. Thus, in some embodiments, at least one RNA selected from small U2, miR-720, miR-451, 13207, and 13750 may include, for example, both mature miR-720 and pre-miR-720; or may include, for example, mature miR-720, pre-miR-720, and mature miR-451, etc.

In the present disclosure, the term "target RNA" is used for convenience to refer to small U2, miR-720, miR-451, 13207, and 13750 and also to other target RNAs. Thus, it is to be understood that when a discussion is presented in terms of a target RNA, that discussion is specifically intended to encompass small U2, miR-720, miR-451, 13207, 13750, and/or other target RNAs.

In some embodiments, detection of a level of target RNA that is greater than a normal level of target RNA indicates the presence of lung cancer in the sample. In some embodiments, detection of a level of target RNA that is less than a normal level of target RNA indicates the presence of lung cancer in the sample. In some embodiments, the detecting is done quantitatively. In other embodiments, the detecting is done qualitatively. In some embodiments, detecting a target RNA comprises forming a complex comprising a polynucleotide and a nucleic acid selected from a target RNA, a DNA amplicon of a target RNA, and a complement of a target RNA. In some embodiments, the level of the complex is then detected and compared to a normal level of the same complex.

"Non-small cell lung cancer" or "NSCLC" is one of two categories of lung cancer found in humans. About 80% of patients diagnosed with lung cancer have non-small cell lung cancer. NSCLC is further broken down into three sub-categories, depending on the cells in which they originate: (i) adenocarcinoma, which originates in the cells that line the alveoli and make substances such as mucus; (ii) squamous cell or epidermoid carcinoma, which originates in the squamous cells; and (iii) large cell carcinoma, which may originate in several different types of large cells. More than 50% of patients with NSCLC have either adenocarcinoma or squamous cell carcinoma. The histology class nonsquamous cell carcinoma includes both adenocarcinoma and large cell carcinoma.

Cancer can be divided into clinical and pathological stages. The clinical stage is based on all available information about a tumor, such as information gathered through physical examination, radiological examination, endoscopy, etc. The pathological stage is based on the microscopic pathology of a tumor.

The TNM (tumor, node, metastasis) system classifies a cancer by three parameters—the size of the tumor and whether it has invaded nearby tissues, involvement of lymph nodes, and metastases. T (tumor) is assigned a number from 1 to 4, according to the size and extent of the primary tumor. N (node) is assigned a number from 0 to 3, in which 0 means no spreading to the lymph nodes, 1 is spreading to the closest lymph nodes, and 3 is spreading to the most distant and greatest number of lymph nodes, and 2 is intermediate between 1 and 3. M (metastasis) is assigned 0 for no distant metastases, or 1 for distant metastases beyond regional lymph nodes.

For lung cancer, Overall Stage Grouping assigns a cancer a roman numeral of 0, I, II, III, and IV, and a letter, A or B, depending on the stage. Stage 0 is carcinoma in situ, which usually does not form a tumor. Stages IA (T1N0M0) and IB (T2N0M0) is cancer that is localized to one part of the body. Stage IIA (T1N1M0) and IIB (T2N1M0 and T3N0M0) is cancer that is localized, but more advanced. Stage IIIA (T1-3N2M0 or T3N1M0) and IIIB (any T4 or any N3M0) cancer is also locally advanced. Stage IV (any M1) is cancer that has metastasized. As used herein, the term "early stage cancer" refers to Stages IA and IB and Stages IIA and IIB cancers.

Mature human microRNAs are typically composed of 17-27 contiguous ribonucleotides, and often are 21 or 22 nucleotides in length. While not intending to be bound by theory, mammalian microRNAs mature as described herein. A gene coding for a microRNA is transcribed, leading to production of a microRNA precursor known as the "pri-microRNA" or "pri-miRNA." The pri-miRNA can be part of a polycistronic RNA comprising multiple pri-miRNAs. In some circumstances, the pri-miRNA forms a hairpin with a stem and loop, which may comprise mismatched bases. The hairpin structure of the pri-miRNA is recognized by Drosha, which is an RNase III endonuclease protein. Drosha can recognize terminal loops in the pri-miRNA and cleave approximately two helical turns into the stem to produce a 60-70 nucleotide precursor known as the "pre-microRNA" or "pre-miRNA." Drosha can cleave the pri-miRNA with a staggered cut typical of RNase III endonucleases yielding a pre-miRNA stem loop with a 5' phosphate and an approximately 2-nucleotide 3' overhang. Approximately one helical turn of the stem (about 10 nucleotides) extending beyond the Drosha cleavage site can be essential for efficient processing. The pre-miRNA is subsequently actively transported from the nucleus to the cytoplasm by Ran-GTP and the export receptor Exportin-5.

The pre-miRNA can be recognized by Dicer, another RNase III endonuclease. In some circumstances, Dicer recognizes the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and an approximately 2-nucleotide 3' overhang. The resulting siRNA-like duplex, which may comprise mismatches, comprises the mature microRNA and a similar-sized fragment known as the microRNA*. The microRNA and microRNA* may be derived from opposing arms of the pri-miRNA and pre-miRNA. The mature microRNA is then loaded into the RNA-induced silencing complex ("RISC"), a ribonucleoprotein complex. In some cases, the microRNA* also has gene silencing or other activity.

Nonlimiting exemplary small cellular RNAs include, in addition to microRNAs, small nuclear RNAs, tRNAs, ribosomal RNAs, snoRNAs, piRNAs, siRNAs, and small RNAs formed by processing any of those RNAs. In some embodiments, a target RNA is a small cellular RNA.

In some embodiments, a target RNA, such as at least one RNA selected from small U2, miR-720, miR-451, 13207, and 13750, can be measured in samples collected at one or more times from a patient to monitor the status or progress of lung cancer in the patient.

In some embodiments, a sample to be tested is obtained using one or more techniques commonly used for collecting lung tissue, e.g., bronchoscopy, bronchial washing, brushing, or transbronchial needle aspiration. In some embodiments, the sample is obtained from a patient without lesions by bronchoalveolar lavage, i.e., washing the airways with saline, to obtain cells. In some embodiments, the sample is obtained by biopsy, such as computed tomography (CT)-aided needle biopsy.

In some embodiments, the sample to be tested is a bodily fluid, such as blood, sputum, mucus, saliva, urine, semen, etc. In some embodiments, a sample to be tested is a blood sample. In some embodiments, the blood sample is whole blood. In some embodiments, the blood sample is a sample of blood cells. In some embodiments, the blood sample is plasma. In some embodiments, the blood sample is serum.

The clinical sample to be tested is, in some embodiments, freshly obtained. In other embodiments, the sample is a fresh frozen specimen. In some embodiments, the sample is a tissue sample, such as a formalin-fixed paraffin embedded sample. In some embodiments, the sample is a liquid cytology sample.

In some embodiments, the methods described herein are used for early detection of lung cancer in a sample of lung cells, such as those obtained by routine bronchoscopy. In some embodiments, the methods described herein are used for early detection of lung cancer in a sample of blood or serum.

In some embodiments, the clinical sample to be tested is obtained from individuals who have one or more of the following risk factors: history of smoking, over 45 years of age, exposure to radon gas, secondhand smoke or occupational carcinogens (e.g., asbestos, radiation, arsenic, chromates, nickel, chloromethyl ethers, mustard gas, or coke-oven emissions), or lungs scarred by prior disease such as tuberculosis. In some embodiments, the clinical sample is obtained from individuals who have diagnostic signs or clinical symptoms that may be associated with lung cancer, such as abnormal chest x-ray and/or computed tomography ("CT") scan, cough, localized chest pain, or hoarseness.

Thus, in some embodiments, methods described herein can be used for routine screening of healthy individuals with no risk factors. In some embodiments, methods described herein are used to screen asymptomatic individuals having one or more of the above-described risk factors.

In some embodiments, the methods described herein can be used to detect early stage lung cancer. In some embodiments, the methods described herein can be used to detect stage I lung cancer. In some embodiments, the methods described herein can be used to detect stage I or stage II lung cancer. In some embodiments, a method of detecting early stage lung cancer comprises detecting at least one, at least two, at least three, or at least four RNAs selected from small U2, miR-720, miR-451, 13207, and 13750. In some embodiments, a method of detecting early stage lung cancer comprises detecting at least one, at least two, or at least three RNAs selected from small U2, miR-720, miR-451, and 13750. In some embodiments, a method of detecting early stage lung cancer comprises detecting small U2. In some embodiments, a method of detecting early stage lung cancer comprises detecting small U2 and at least one additional RNA selected from miR-720, miR-451, and 13750. In some embodiments, a method of detecting early stage lung cancer comprises detecting small U2 and miR-451. In some embodiments, a method of detecting early stage lung cancer comprises detecting small U2 and miR-720. In some embodiments, a method of detecting early stage lung cancer comprises detecting small U2 and 13750. In some embodiments, a method of detecting early stage lung cancer comprises detecting small U2 and at least two additional RNAs selected from miR-720, miR-451, and 13750. In some embodiments, a method of detecting early stage lung cancer comprises detecting 13750. In some embodiments, a method of detecting early stage lung cancer comprises detecting 13750 and at least one additional RNA selected from miR-720, miR-451, and small U2. In some embodiments, a method of detecting early stage lung cancer comprises detecting 13750 and miR-451. In some embodiments, a method of detecting early stage lung cancer comprises detecting 13750 and miR-720. In some embodiments, a method of detecting early stage lung cancer comprises detecting small 13750 and at least two additional RNAs selected from miR-720, miR-451, and small U2. In some embodiments, a method of detecting early stage lung cancer comprises detecting small U2, miR-720, miR-451, and 13750.

In some embodiments, a method of detecting stage I lung cancer comprises detecting at least one, at least two, at least three, or at least four RNAs selected from small U2, miR-720, miR-451, 13207, and 13750. In some embodiments, a method of detecting stage I lung cancer comprises detecting at least one, at least two, or at least three RNAs selected from small U2, miR-720, miR-451, and 13750. In some embodiments, a method of detecting stage I lung cancer comprises detecting small U2. In some embodiments, a method of detecting stage I lung cancer comprises detecting small U2 and at least one additional RNA selected from miR-720, miR-451, and 13750. In some embodiments, a method of detecting stage I lung cancer comprises detecting small U2 and miR-451. In some embodiments, a method of detecting stage I lung cancer comprises detecting small U2 and miR-720. In some embodiments, a method of detecting stage I lung cancer comprises detecting small U2 and 13750. In some embodiments, a method of detecting stage I lung cancer comprises detecting small U2 and at least two additional RNAs selected from miR-720, miR-451, and 13750. In some embodiments, a method of detecting stage I lung cancer comprises detecting 13750. In some embodiments, a method of detecting stage I lung cancer comprises detecting 13750 and at least one additional RNA selected from miR-720, miR-451, and small U2. In some embodiments, a method of detecting stage I lung cancer comprises detecting 13750 and miR-451. In some embodiments, a method of detecting stage I lung cancer comprises detecting 13750 and miR-720. In some embodiments, a method of detecting stage I lung cancer comprises detecting small 13750 and at least two additional RNAs selected from miR-720, miR-451, and small U2. In some embodiments, a method of detecting stage I lung cancer comprises detecting small U2, miR-720, miR-451, and 13750.

In some embodiments, the methods described herein can be used to assess the effectiveness of a treatment for lung cancer in a patient. In some embodiments, target RNA levels, such as at least one RNA selected from small U2, miR-720, miR-451, 13207, and 13750, are determined at various times during the treatment, and are compared to target RNA levels from an archival sample taken from the patient before the manifestation of any signs of lung cancer or before beginning treatment. In some embodiments, target RNA levels are compared to target RNA levels from an archival sample of normal tissue taken from the patient or a sample of tissue taken from a tumor-free part of the patient's lung by biopsy. Ideally, target RNA levels in the normal sample evidence no aberrant changes in target RNA levels. Thus, in such embodiments, the progress of treatment of an individual with lung cancer can be assessed by comparison to a sample from the same individual when he was healthy or prior to beginning treatment, or by comparison to a sample of healthy lung cells from the same individual.

In some embodiments, use of at least one RNA selected from small U2, miR-720, miR-451, 13207, and 13750, for monitoring the response of a lung cancer patient to therapy is provided. In some embodiments, use of small U2 for monitoring the response of a lung cancer patient to therapy is provided. In some embodiments, use of 13750 for monitoring the response of a lung cancer patient to therapy is provided. In some embodiments, use of small U2 and 13750 for monitoring the response of a lung cancer patient to therapy is provided. In some embodiments, use of small U2, miR-720, and 13750 for monitoring the response of a lung cancer patient to therapy is provided. In some embodiments, use of small U2, miR-720, miR-451, and 13750 for monitoring the response of a lung cancer patient to therapy is provided. In the monitoring to therapy, preferably a blood sample, such as serum, is used. In the monitoring of therapy, the levels of small U2, miR-720, miR-451, 13207, and 13750, measured individually or collectively, are assessed against their baseline levels determined at the initiation of therapy. In some embodiments, changes from the baseline levels indicate response to therapy where the levels for the particular RNA remain the same, or for small U2, the level decreases, or for miR-720, miR-451, 13207, or 13750, the levels increase. In some embodiments, changes from the baseline levels indicate resistance to therapy where for small U2, the level increases, or for miR-720, miR-451, 13207, or 13750, the levels decrease.

In some embodiments, a method comprises detecting at least one RNA selected from small U2, miR-720, miR-451, 13207, and 13750. In some embodiments, a method comprises detecting small U2. In some such embodiments, a method further comprises detecting at least one, at least two, at least three, or at least four RNAs selected from miR-720, miR-451, 13207, and 13750, In some embodiments, in combination with detecting at least one, at least two, at least three, or at least four RNAs selected from small U2, miR-720, miR-451, 13207, and 13750, a method further comprises detecting at least one additional target RNA. Such additional target RNAs include, but are not limited to, other microRNAs, small cellular RNAs, and mRNAs.

In embodiments in which the method comprises detecting levels of at least two RNAs, such as at least two RNAs selected from small U2, miR-720, miR-451, 13207, and 13750, the levels of a plurality of RNAs may be detected concurrently or simultaneously in the same assay reaction. In some embodiments, RNA levels are detected concurrently or simultaneously in separate assay reactions. In some embodiments, RNA levels are detected at different times, e.g., in serial assay reactions.

In some embodiments, a method comprises detecting the level of small U2 in a sample from a subject, wherein detection of a level of small U2 that is greater than a normal level of the RNA indicates the presence of lung cancer in the subject. In some embodiments, a method comprises detecting the level of miR-720 in a sample from a subject, wherein detection of a level of miR-720 that is less than a normal level of the RNA indicates the presence of lung cancer in the subject. In some embodiments, a method comprises detecting the level of miR-451 in a sample from a subject, wherein detection of a level of miR-451 that is less than a normal level of the RNA indicates the presence of lung cancer in the subject. In some embodiments, a method comprises detecting the level of 13207 in a sample from a subject, wherein detection of a level of 13207 that is less than a normal level of the RNA indicates the presence of lung cancer in the subject. In some embodiments, a method comprises detecting the level of 13750 in a sample from a subject, wherein detection of a level of 13750 that is less than a normal level of the RNA indicates the presence of lung cancer in the subject. Further, methods of detecting lung cancer in a subject comprising detecting any combination of one, two, three, four, or five of the foregoing RNAs are also contemplated.

In some embodiments, a method of facilitating diagnosis of lung cancer in a subject is provided. Such methods comprise detecting the level of at least one RNA selected from small U2, miR-720, miR-451, 13207, and 13750 in a sample from the subject. In some embodiments, information concerning the level of at least one RNA selected from small U2, miR-720, miR-451, 13207, and 13750 in the sample from the subject is communicated to a medical practitioner. A "medical practitioner," as used herein, refers to an individual or entity that diagnoses and/or treats patients, such as a hospital, a clinic, a physician's office, a physician, a nurse, or an agent of any of the aforementioned entities and individuals. In some embodiments, detecting the level of at least one RNA selected from small U2, miR-720, miR-451, 13207, and 13750 is carried out at a laboratory that has received the subject's sample from the medical practitioner or agent of the medical practitioner. The laboratory carries out the detection by any method, including those described herein, and then communicates the results to the medical practitioner. A result is "communicated," as used herein, when it is provided by any means to the medical practitioner. In some embodiments, such communication may be oral or written, may be by telephone, in person, by e-mail, by mail or other courier, or may be made by directly depositing the information into, e.g., a database accessible by the medical practitioner, including databases not controlled by the medical practitioner. In some embodiments, the information is maintained in electronic form. In some embodiments, the information can be stored in a memory or other computer readable medium, such as RAM, ROM, EEPROM, flash memory, computer chips, digital video discs (DVD), compact discs (CDs), hard disk drives (HDD), magnetic tape, etc.

In some embodiments, methods of detecting the presence lung cancer are provided. In some embodiments, methods of diagnosing lung cancer are provided. In some embodiments, the method comprises obtaining a sample from a subject and providing the sample to a laboratory for detection of levels of at least one RNA selected from small U2, miR-720, miR-451, 13207, and 13750 in the sample. In some embodiments, the method further comprises receiving a communication from the laboratory that indicates the levels of at least one RNA selected from small U2, miR-720, miR-451, 13207, and 13750 in the sample. In some embodiments, lung cancer is present if the level of small U2 in the sample is greater than a normal level of small U2. In some embodiments, lung cancer is present if the level of at least one RNA selected from miR-720, miR-451, 13207, and 13750 in the sample is less than a normal level of the respective RNA. A "laboratory," as used herein, is any facility that detects the level of at least one RNA selected from small U2, miR-720, miR-451, 13207, and 13750 in a sample by any method, including the methods described herein, and communicates the level to a medical practitioner. In some embodiments, a laboratory is under the control of a medical practitioner. In some embodiments, a laboratory is not under the control of the medical practitioner.

When a laboratory communicates the level of at least one RNA selected from small U2, miR-720, miR-451, 13207, and 13750 to a medical practitioner, in some embodiments, the laboratory communicates a numerical value representing the level of at least one RNA selected from small U2, miR-720, miR-451, 13207, and 13750 in the sample, with or without providing a numerical value for a normal level. In some embodiments, the laboratory communicates the level of at least one RNA selected from small U2, miR-720, miR-451, 13207, and 13750 by providing a qualitative value, such as "high," "low," "elevated," "decreased," etc.

As used herein, when a method relates to detecting lung cancer, determining the presence of lung cancer, and/or diagnosing lung cancer, the method includes activities in which the steps of the method are carried out, but the result is negative for the presence of lung cancer. That is, detecting, determining, and diagnosing lung cancer include instances of carrying out the methods that result in either positive or negative results (e.g., whether small U2 level is normal or greater than normal, or whether miR-451, miR-720, 13207, and/or 13750 levels are normal or less than normal).

As used herein, the term "subject" means a human. In some embodiments, the methods described herein may be used on samples from non-human animals.

The common, or coordinate, expression of target RNAs that are physically proximal to one another in the genome permits the informative use of such chromosome-proximal target RNAs in methods herein.

The coding sequence for small U2 is located on chromosome 17 at 17q21.31, and appears to be present in multiple copies. The coding sequence for miR-720 is located on chromosome 3: 164,059,029-164,059,238 (Ensembl release 65—December 2011; chromosome 3q26.1). The coding sequence for miR-451 is located on chromosome 17: 27,188,387-27,188,458 (Ensembl release 65—December 2011; chromosome 17q11.2). The coding sequence for 13207 is located on chromosome 10: 687,614-687,734 (Ensembl release 65—December 2011; chromosome 10p15.3). The coding sequence for 13750 is located on chromosome 17: 27,188,673-27,188,748 (Ensembl release 65—December 2011; chromosome 17q11.2). In some embodiments, the level of expression of one or more target RNAs located within about 1 kilobase (kb), within about 2 kb, within about 5 kb, within about 10 kb, within about 20 kb, within about 30 kb, within about 40 kb, and even within about 50 kb of the chromosomal location of small U2, miR-720, miR-451, or 13207 is detected in lieu of, or in addition to, measurement of expression of the respective target RNA in the methods described herein. See Baskerville, S. and Bartel D. P. (2005) RNA 11:241-247.

In some embodiments, the methods further comprise detecting in a sample the expression of at least one target RNA gene located in close proximity to chromosomal features, such as cancer-associated genomic regions, fragile sites, and human papilloma virus integration sites.

In some embodiments, more than RNA is detected simultaneously in a single reaction. In some embodiments, at least 2, at least 3, at least 5, or at least 10 RNAs are detected simultaneously in a single reaction. In some embodiments, all RNAs are detected simultaneously in a single reaction.

4.1.2. Exemplary Controls

In some embodiments, a normal level (a "control") of a target RNA, such as an RNA selected from small U2, miR-720, miR-451, 13207, and 13750, can be determined as an average level or range that is characteristic of normal lung cells or other reference material, against which the level measured in the sample can be compared. The determined average or range of a target RNA in normal subjects can be used as a benchmark for detecting above-normal levels of the target RNA that are indicative of lung cancer. In some embodiments, normal levels of a target RNA can be determined using individual or pooled RNA-containing samples from one or more individuals, such as from normal lung tissue from patients undergoing surgical resections for stage I, II or IIIA non-small cell lung cancer.

In some embodiments, determining a normal level of a target RNA, such as at least one RNA selected from small U2, miR-720, miR-451, 13207, and 13750, comprises detecting a complex comprising a polynucleotide for detection hybridized to a nucleic acid selected from a target RNA, a DNA amplicon of the target RNA, and a complement of the target RNA. That is, in some embodiments, a normal level can be determined by detecting a DNA amplicon of the target RNA, or a complement of the target RNA rather than the target RNA itself. In some embodiments, a normal level of such a complex is determined and used as a control. The normal level of the complex, in some embodiments, correlates to the normal level of the target RNA. Thus, when a normal level of a target is discussed herein, that level can, in some embodiments, be determined by detecting such a complex.

In some embodiments, a control comprises RNA from cells of a single individual, e.g., from normal tissue of a patient undergoing surgical resection for stage I, II or IIIA lung cancer. In some embodiments, a control comprises RNA from blood, such as whole blood or serum, of a single individual. In some embodiments, a control comprises RNA from a pool of cells from multiple individuals. In some embodiments, a control comprises RNA from a pool of blood, such as whole blood or serum, from multiple individuals. In some embodiments, a control comprises commercially-available human RNA, such as, for example, human lung total RNA (Ambion; AM7968). In some embodiments, a normal level or normal range has already been predetermined prior to testing a sample for an elevated level.

In some embodiments, the normal level of a target RNA, such as at least one RNA selected from small U2, miR-720, miR-451, 13207, and 13750, can be determined from one or more continuous cell lines, typically cell lines previously shown to have levels of RNAs that approximate the levels in normal lung cells.

In some embodiments, a method comprises detecting the level of at least one RNA selected from small U2, miR-720, miR-451, 13207, and 13750. In some embodiment, in addition to detecting the level of at least one RNA selected from small U2, miR-720, miR-451, 13207, and 13750, a method comprises detecting the level of at least one additional target RNA. In some embodiments, a method comprises detecting the level of small U2. In some such embodiments, a method further comprises detecting the level of at least one RNA selected from miR-720, miR-451, 13207, and 13750. In some embodiments, a method comprises detecting the level of 13750. In some such embodiments, a method further comprises detecting the level of at least one RNA selected from miR-720, miR-451, 13207, and small U2. In some embodiments, a method further comprises detecting the level of at least one additional target RNA. In some embodiments, a method further comprises comparing the level of at least one RNA selected from small U2, miR-720, miR-451, 13207, and 13750 to a normal level of the at least one RNA. In some embodiments, a method further comprises comparing the level of at least one target RNA to a control level of the at least one target RNA. A control level of a target RNA is, in some embodiments, the level of the target RNA in a normal cell. A control level of a target RNA is, in some embodiments, the level of the target RNA in a serum from a healthy individual. In some such embodiments, a control level may be referred to as a normal level.

In some embodiments, a greater level of small U2 in a sample relative to the level of small U2 in normal cells or normal serum, and/or a reduced level of at least one, at least two, at least three, or at least four RNAS selected from miR-720, miR-451, 13207, and 13750 relative to the level of the respective RNA in normal cells or normal serum, indicates lung cancer. In some embodiments, a greater level of small U2 in a sample relative to the level of small U2 in normal cells or normal serum indicates lung cancer. In some embodiments, a reduced level of miR-720 in a sample relative to the level of miR-720 in normal cells or normal serum indicates lung cancer. In some embodiments, a reduced level of miR-451 in a sample relative to the level of miR-451 in normal cells or normal serum indicates lung cancer. In some embodiments, a reduced level of 13207 in a sample relative to the level of 13207 in normal cells or normal serum indicates lung cancer. In some embodiments, a reduced level of 13750 in a sample relative to the level of 13750 in normal cells or normal serum indicates lung cancer.

In some embodiments, a greater level of at least one additional target RNA relative to the level of the at least one additional target RNA in a normal cell indicates lung cancer. In some embodiments, a lower level of at least one additional target RNA relative to the level of the at least one additional target RNA in a normal cell indicates lung cancer.

In some embodiments, the level of a target RNA, such as at least one RNA selected from small U2, miR-720, miR-451, 13207, and 13750, is compared to a reference level, e.g., from a confirmed lung cancer. In some such embodiments, a similar level of a target RNA relative to the reference sample indicates lung cancer.

In some embodiments, a level of a target RNA, such as small U2, that is at least about two-fold greater than a normal level of the respective target RNA indicates the presence of lung cancer. In some embodiments, a level of a target RNA, such as small U2, that is at least about two-fold greater than the level of the respective target RNA in a control sample indicates the presence of a lung cancer. In various embodiments, a level of a target RNA, such as small U2, that is at least about 3-fold, at least about 4-fold, at least about 5-fold, at least about 6-fold, at least about 7-fold, at least about 8-fold, at least about 9-fold, or at least about 10-fold greater than the level of the respective target RNA in a control sample indicates the presence of lung cancer. In various embodiments, a level of a target RNA, such as small U2, that is at least about 3-fold, at least about 4-fold, at least about 5-fold, at least about 6-fold, at least about 7-fold, at least about 8-fold, at least about 9-fold, or at least about 10-fold greater than a normal level of the respective target RNA indicates the presence of lung cancer.

In some embodiments, a level of at least one target RNA, such as miR-720, miR-451, 13207, and/or 13750, that is at least about two-fold less than a normal level of the respective target RNA indicates the presence of lung cancer. In some embodiments, a level of at least one target RNA, such as miR-720, miR-451, 13207, and/or 13750, that is at least about two-fold less than the level of the respective target RNA in a control sample indicates the presence of a lung cancer. In various embodiments, a level of at least one target RNA, such as miR-720, miR-451, 13207, and/or 13750, that is at least about 3-fold, at least about 4-fold, at least about 5-fold, at least about 6-fold, at least about 7-fold, at least about 8-fold, at least about 9-fold, or at least about 10-fold less than the level of the respective target RNA in a control sample indicates the presence of lung cancer. In various embodiments, a level of at least one target RNA, such as miR-720, miR-451, 13207, and/or 13750, that is at least about 3-fold, at least about 4-fold, at least about 5-fold, at least about 6-fold, at least about 7-fold, at least about 8-fold, at least about 9-fold, or at least about 10-fold less than a normal level of the respective target RNA indicates the presence of lung cancer.

In some embodiments, a control level of a target RNA, such as at least one RNA selected from small U2, miR-720, miR-451, 13207, and 13750, is determined contemporaneously, such as in the same assay or batch of assays, as the level of the target RNA in a sample. In some embodiments, a control level of a target RNA, such as at least one RNA selected from small U2, miR-720, miR-451, 13207, and 13750, is not determined contemporaneously as the level of the target RNA in a sample. In some such embodiments, the control level has been determined previously.

In some embodiments, the level of a target RNA is not compared to a control level, for example, when it is known that the target RNA is present at very low levels, or not at all, in normal cells. In such embodiments, detection of a high level of the target RNA in a sample is indicative of lung cancer. Similarly, in some embodiments, if a target RNA is present at high levels in normal cells or normal serum, the detection of a very low level in a sample is indicative of lung cancer.

4.1.3. Exemplary Methods of Preparing RNAs

Target RNA can be prepared by any appropriate method. Total RNA can be isolated by any method, including, but not limited to, the protocols set forth in Wilkinson, M. (1988) Nucl. Acids Res. 16(22):10,933; and Wilkinson, M. (1988) Nucl. Acids Res. 16(22): 10934, or by using commercially-available kits or reagents, such as the TRIzol® reagent (Invitrogen™), Total RNA Extraction Kit (iNtRON Biotechnology), Total RNA Purification Kit (Norgen Biotek Corp.), RNAqueous™ (Ambion), MagMAX™ (Ambion), Recover-All™ (Ambion), RNeasy (Qiagen), etc.

In some embodiments, small RNAs are isolated or enriched. In some embodiments "small RNA" refers to RNA molecules smaller than about 200 nucleotides (nt) in length. In some embodiments, "small RNA" refers to RNA molecules smaller than about 100 nt, smaller than about 90 nt, smaller than about 80 nt, smaller than about 70 nt, smaller than about 60 nt, smaller than about 50 nt, or smaller than about 40 nt.

Enrichment of small RNAs can be accomplished by method. Such methods include, but are not limited to, methods involving organic extraction followed by adsorption of nucleic acid molecules on a glass fiber filter using specialized binding and wash solutions, and methods using spin column purification. Enrichment of small RNAs may be accomplished using commercially-available kits, such as mirVana™ Isolation Kit (Ambion), mirPremier™ microRNA Isolation Kit (Sigma-Aldrich), PureLink™ miRNA Isolation Kit (Invitrogen), miRCURY™ RNA isolation kit (Exiqon), microRNA Purification Kit (Norgen Biotek Corp.), miRNeasy kit (Qiagen), etc. In some embodiments, purification can be accomplished by the TRIzol® (Invitrogen) method, which employs a phenol/isothiocyanate solution to which chloroform is added to separate the RNA-containing aqueous phase. Small RNAs are subsequently recovered from the aqueous by precipitation with isopropyl alcohol. In some embodiments, small RNAs can be purified using chromatographic methods, such as gel electrophoresis using the flashPAGE™ Fractionator available from Applied Biosystems.

In some embodiments, small RNA is isolated from other RNA molecules to enrich for target RNAs, such that the small RNA fraction (e.g., containing RNA molecules that are 200 nucleotides or less in length, such as less than 100 nucleotides in length, such as less than 50 nucleotides in length, such as from about 10 to about 40 nucleotides in length) is substantially pure, meaning it is at least about 80%, 85%, 90%, 95% pure or more, but less than 100% pure, with respect to larger RNA molecules. Alternatively, enrichment of small RNA can be expressed in terms of fold-enrichment. In some embodiments, small RNA is enriched by about, at least about, or at most about 5×, 10×, 20×, 30×, 40×, 50×, 60×, 70×, 80×, 90×, 100×, 110×, 120×, 130×, 140×, 150×, 160×, 170×, 180×, 190×, 200×, 210×, 220×, 230×, 240×, 250×, 260×, 270×, 280×, 290×, 300×, 310×, 320×, 330×, 340×, 350×, 360×, 370×, 380×, 390×, 400×, 410×, 420×, 430×, 440×, 450×, 460×, 470×, 480×, 490×, 500×, 600×, 700×, 800×, 900×, 1000×, 1100×, 1200×, 1300×, 1400×, 1500×, 1600×, 1700×, 1800×, 1900×, 2000×, 3000×, 4000×, 5000×, 6000×, 7000×, 8000×, 9000×, 10,000× or more, or any range derivable therein, with respect to the concentration of larger RNAs in an RNA isolate or total RNA in a sample.

In some embodiments, RNA levels are measured in a sample in which RNA has not first been purified from the cells. In some embodiments, RNA levels are measured in a sample in which RNA has been isolated, but not enriched for small RNAs.

In some embodiments, RNA is modified before a target RNA, such as at least one RNA selected from small U2, miR-720, miR-451, 13207, and 13750, is detected. In some embodiments, the modified RNA is total RNA. In other embodiments, the modified RNA is small RNA that has been purified from total RNA or from cell lysates, such as RNA less than 200 nucleotides in length, such as less than 100 nucleotides in length, such as less than 50 nucleotides in length, such as from about 10 to about 40 nucleotides in length. RNA modifications that can be utilized in the methods described herein include, but are not limited to, the addition of a poly-dA or a poly-dT tail, which can be accomplished chemically or enzymatically, and/or the addition of a small molecule, such as biotin.

In some embodiments, a target RNA, such as at least one RNA selected from small U2, miR-720, miR-451, 13207, and 13750, is reverse transcribed. In some embodiments, cDNA is modified when it is reverse transcribed, such as by adding a poly-dA or a poly-dT tail during reverse transcription. In other embodiments, RNA is modified before it is reverse transcribed. In some embodiments, total RNA is reverse transcribed. In other embodiments, small RNAs are isolated or enriched before the RNA is reverse transcribed.

When a target RNA, such as at least one RNA selected from small U2, miR-720, miR-451, 13207, and 13750, is reverse transcribed, a complement of the target RNA is formed. In some embodiments, the complement of a target RNA is detected rather than a target RNA itself (or a DNA copy thereof). Thus, when the methods discussed herein indicate that a target RNA is detected, or the level of a target RNA is determined, such detection or determination may be carried out on a complement of a target RNA instead of, or in addition to, the target RNA itself. In some embodiments, when the complement of a target RNA is detected rather than the target RNA, a polynucleotide for detection is used that is complementary to the complement of the target RNA. In such embodiments, a polynucleotide for detection comprises at least a portion that is identical in sequence to the target RNA, although it may contain thymidine in place of uridine, and/or comprise other modified nucleotides.

In some embodiments, the method of detecting a target RNA, such as at least one RNA selected from small U2, miR-720, miR-451, 13207, and 13750, comprises amplifying cDNA complementary to the target RNA. Such amplification can be accomplished by any method. Exemplary methods include, but are not limited to, real time PCR, endpoint PCR, and amplification using T7 polymerase from a T7 promoter annealed to a cDNA, such as provided by the SenseAmp Plus™ Kit available at Implen, Germany.

When a target RNA or a cDNA complementary to a target RNA is amplified, in some embodiments, a DNA amplicon of the target RNA is formed. A DNA amplicon may be single stranded or double-stranded. In some embodiments, when a DNA amplicon is single-stranded, the sequence of the DNA amplicon is related to the target RNA in either the sense or antisense orientation. In some embodiments, a DNA amplicon of a target RNA is detected rather than the target RNA itself. Thus, when the methods discussed herein indicate that a target RNA is detected, or the level of a target RNA is determined, such detection or determination may be carried out on a DNA amplicon of the target RNA instead of, or in addition to, the target RNA itself. In some embodiments, when the DNA amplicon of the target RNA is detected rather than the target RNA, a polynucleotide for detection is used that is complementary to the complement of the target RNA. In some embodiments, when the DNA amplicon of the target RNA is detected rather than the target RNA, a polynucleotide for detection is used that is complementary to the target RNA. Further, in some embodiments, multiple polynucleotides for detection may be used, and some polynucleotides may be complementary to the target RNA and some polynucleotides may be complementary to the complement of the target RNA.

In some embodiments, the method of detecting one or more target RNAs, including small U2, miR-720, miR-451, 13207, and/or 13750 comprises RT-PCR, as described below. In some embodiments, detecting one or more target RNAs comprises real-time monitoring of an RT-PCR reaction, which can be accomplished by any method. Such methods include, but are not limited to, the use of TaqMan®, Molecular beacon, or Scorpion probes (i.e., FRET probes) and the use of intercalating dyes, such as SYBR green, EvaGreen, thiazole orange, YO-PRO, TO-PRO, etc.

4.1.4. Exemplary Analytical Methods

As described above, methods are presented for detecting lung cancer. In some embodiments, the method comprises detecting a level of at least one RNA selected from small U2, miR-720, miR-451, 13207, and 13750. In some embodiments, the method further comprises detecting a level of at least one additional target RNA.

In some embodiments, a method comprises detecting the level of small U2. In some embodiments, a method comprises detecting the level of 13750. In some embodiments, a method comprises detecting the level of miR-720. In some embodiments, a method comprises detecting the level of miR-451. In some embodiments, a method comprises detecting the levels of at least two RNAs selected from small U2, miR-720, miR-451, 13207, and 13750. In some embodiments, a method comprises detecting the levels of small U2 and 13750. In some embodiments, a method comprises detecting the levels of small U2 and miR-451. In some embodiments, a method comprises detecting the levels of small U2 and miR-720. In some embodiments, a method comprises detecting the levels of 13750 and miR-451. In some embodiments, a method comprises detecting the levels of 13750 and miR-720. In some embodiments, a method comprises detecting the levels of miR-451 and miR-720. In some embodiments, a method comprises detecting the levels of at least three RNAs selected from small U2, miR-720, miR-451, 13207, and 13750. In some embodiments, a method comprises detecting the levels of small U2, miR-720, and 13750. In some embodiments, a method comprises detecting the levels of small U2, miR-720, and miR-451. In some embodiments, a method comprises detecting the levels of small U2, miR-451, and 13750. In some embodiments, a method comprises detecting the levels of miR-720, miR-451, and 13750. In some embodiments, a method comprises detecting the levels of at least four RNAs selected from small U2, miR-720, miR-451, 13207, and 13750. In some embodiments, a method comprises detecting the levels of small U2, miR-720, miR-451, and 13750.

In some embodiments, a method comprises detecting a level of a target RNA, such as small U2, that is greater in the sample than a normal level of the target RNA in a control sample, such as a sample derived from normal lung cells or a sample of normal serum. In some embodiments, a method comprises detecting a level of a target RNA, such as miR-720, miR-451, 13207 and/or 13750, that is lower in the sample than a normal level of the target RNA in a control sample, such as a sample derived from normal lung cells or normal serum.

In some embodiments, miR-720 is mature miR-720. In some embodiments, miR-451 is mature miR-451. In some embodiments, 13207 is mature 13207. In some embodiments, 13750 is mature 13750. In some embodiments, a target RNA, in its mature form, comprises fewer than 30 nucleotides. In some embodiments, a target RNA is a microRNA. In some embodiments, a target RNA is a small cellular RNA.

In some embodiments, in addition to detecting a level of at least one RNA selected from small U2, miR-720, miR-451, 13207, and 13750, a method further comprises detecting a level of at least one target RNA of the human miRNome. As used herein, the term "human miRNome" refers to all microRNA genes in a human cell and the mature microRNAs produced therefrom.

Any analytical procedure capable of permitting specific and quantifiable (or semi-quantifiable) detection of a target RNA, such as at least one RNA selected from small U2, miR-720, miR-451, 13207, and 13750, may be used in the methods herein presented. Such analytical procedures include, but are not limited to, the microarray methods and the RT-PCR methods set forth in the Examples, and methods known to those skilled in the art.

In some embodiments, detection of a target RNA, such as at least one RNA selected from small U2, miR-720, miR-451, 13207, and 13750, comprises forming a complex comprising a polynucleotide that is complementary to a target RNA or to a complement thereof, and a nucleic acid selected from the target RNA, a DNA amplicon of the target RNA, and a complement of the target RNA. Thus, in some embodiments, the polynucleotide forms a complex with a target RNA. In some embodiments, the polynucleotide forms a complex with a complement of the target RNA, such as a cDNA that has been reverse transcribed from the target RNA. In some embodiments, the polynucleotide forms a complex with a DNA amplicon of the target RNA. When a double-stranded DNA amplicon is part of a complex, as used herein, the complex may comprise one or both strands of the DNA amplicon. Thus, in some embodiments, a complex comprises only one strand of the DNA amplicon. In some embodiments, a complex is a triplex and comprises the polynucleotide and both strands of the DNA amplicon. In some embodiments, the complex is formed by hybridization between the polynucleotide and the target RNA, complement of the target RNA, or DNA amplicon of the target RNA. The polynucleotide, in some embodiments, is a primer or probe.

In some embodiments, a method comprises detecting the complex. In some embodiments, the complex does not have to be associated at the time of detection. That is, in some embodiments, a complex is formed, the complex is then dissociated or destroyed in some manner, and components from the complex are detected. An example of such a system is a TaqMan® assay. In some embodiments, when the polynucleotide is a primer, detection of the complex may comprise amplification of the target RNA, a complement of the target RNA, or a DNA amplicon of a target RNA.

In some embodiments the analytical method used for detecting at least one target RNA, including at least one RNA selected from small U2, miR-720, miR-451, 13207, and 13750, in the methods set forth herein includes real-time quantitative RT-PCR. See Chen, C. et al. (2005) *Nucl. Acids Res.* 33:e179 and PCT Publication No. WO 2007/117256, which are incorporated herein by reference in its entirety. In some embodiments, the analytical method used for detecting at least one target RNA includes the method described in U.S. Publication No. US2009/0123912 A1, which is incorporated herein by reference in its entirety. In an exemplary method described in that publication, an extension primer comprising a first portion and second portion, wherein the first portion selectively hybridizes to the 3' end of a particular small RNA and the second portion comprises a sequence for universal primer, is used to reverse transcribe the small RNA to make a cDNA. A reverse primer that selectively hybridizes to the 5' end of the small RNA and a universal primer are then used to amplify the cDNA in a quantitative PCR reaction.

In some embodiments, the analytical method used for detecting at least one target RNA, including at least one RNA selected from small U2, miR-720, miR-451, 13207, and 13750, includes the use of a TaqMan® probe. In some embodiments, the analytical method used for detecting at least one target RNA includes a TaqMan® assay, such as the TaqMan® MicroRNA Assays sold by Applied Biosystems, Inc. In an exemplary TaqMan® assay, total RNA is isolated from the sample. In some embodiments, the assay can be used to analyze about 10 ng of total RNA input sample, such as about 9 ng of input sample, such as about 8 ng of input sample, such as about 7 ng of input sample, such as about 6 ng of input sample, such as about 5 ng of input sample, such as about 4 ng of input sample, such as about 3 ng of input sample, such as about 2 ng of input sample, and even as little as about 1 ng of input sample containing small RNAs.

The TaqMan® assay utilizes a stem-loop primer that is specifically complementary to the 3'-end of a target RNA. In an exemplary TaqMan® assay, hybridizing the stem-loop primer to the target RNA is followed by reverse transcription of the target RNA template, resulting in extension of the 3' end of the primer. The result of the reverse transcription is a chimeric (DNA) amplicon with the step-loop primer sequence at the 5' end of the amplicon and the cDNA of the target RNA at the 3' end. Quantitation of the target RNA is achieved by real time RT-PCR using a universal reverse primer having a sequence that is complementary to a sequence at the 5' end of all stem-loop target RNA primers, a target RNA-specific forward primer, and a target RNA sequence-specific TaqMan® probe.

The assay uses fluorescence resonance energy transfer ("FRET") to detect and quantitate the synthesized PCR product. Typically, the TaqMan® probe comprises a fluorescent dye molecule coupled to the 5'-end and a quencher molecule coupled to the 3'-end, such that the dye and the quencher are in close proximity, allowing the quencher to suppress the fluorescence signal of the dye via FRET. When the polymerase replicates the chimeric amplicon template to which the TaqMan® probe is bound, the 5'-nuclease of the polymerase cleaves the probe, decoupling the dye and the quencher so that FRET is abolished and a fluorescence signal is generated. Fluorescence increases with each RT-PCR cycle proportionally to the amount of probe that is cleaved.

Additional exemplary methods for RNA detection and/or quantification are described, e.g., in U.S. Publication No. US 2007/0077570 (Lao et al.), PCT Publication No. WO 2007/025281 (Tan et al.), U.S. Publication No. US2007/0054287 (Bloch), PCT Publication No. WO2006/0130761 (Bloch), and PCT Publication No. WO 2007/011903 (Lao et al.), which are incorporated by reference herein in their entireties for any purpose.

In some embodiments, quantitation of the results of real-time RT-PCR assays is done by constructing a standard curve from a nucleic acid of known concentration and then extrapolating quantitative information for target RNAs of unknown concentration. In some embodiments, the nucleic acid used for generating a standard curve is an RNA (e.g., a microRNA or other small RNA) of known concentration. In some embodiments, the nucleic acid used for generating a standard curve is a purified double-stranded plasmid DNA or a single-stranded DNA generated in vitro.

In some embodiments, where the amplification efficiencies of the target nucleic acids and the endogenous reference are approximately equal, quantitation is accomplished by the comparative Ct (cycle threshold, e.g., the number of PCR cycles required for the fluorescence signal to rise above background) method. Ct values are inversely proportional to the amount of nucleic acid target in a sample. In some embodiments, Ct values of a target RNA, such as at least one RNA selected from small U2, miR-720, miR-451, 13207, and 13750, can be compared with a control or calibrator, such as RNA (e.g., a microRNAs or other small RNA) from normal tissue. In some embodiments, the Ct values of the calibrator and the target RNA are normalized to an appropriate endogenous housekeeping gene. In some embodiments, a threshold Ct (or a "cutoff Ct") value for a target RNA, such as at least one RNA selected from small U2, miR-720, miR-451, 13207, and 13750, below which lung cancer is indicated, has previously been determined. In such embodiments, a control sample may not be assayed concurrently with the test sample.

In addition to the TaqMan® assays, other real-time RT-PCR chemistries useful for detecting and quantitating PCR products in the methods presented herein include, but are not limited to, Molecular Beacons, Scorpion probes and intercalating dyes, such as SYBR Green, EvaGreen, thiazole orange, YO-PRO, TO-PRO, etc., which are discussed below.

In some embodiments, real-time RT-PCR detection is performed specifically to detect and quantify the level of a single target RNA. The target RNA, in some embodiments, is an RNA selected from small U2, miR-720, miR-451, 13207, and 13750.

As described above, in some embodiments, in addition to detecting the level of at least one RNA selected from small U2, miR-720, miR-451, 13207, and 13750, the level of at least one additional target RNA is detected.

In various other embodiments, real-time RT-PCR detection is utilized to detect, in a single multiplex reaction, at least 2, at least 3, at least 4, at least 5, at least 6, at least 7, or at least 8 target RNAs, including at least one RNA selected from small U2, miR-720, miR-451, 13207, and 13750.

In some multiplex embodiments, a plurality of probes, such as TaqMan® probes, each specific for a different RNA target, is used. In some embodiments, each target RNA-specific probe is spectrally distinguishable from the other probes used in the same multiplex reaction.

In some embodiments, quantitation of real-time RT PCR products is accomplished using a dye that binds to double-stranded DNA products, such as SYBR Green, EvaGreen, thiazole orange, YO-PRO, TO-PRO, etc. In some embodiments, the assay is the QuantiTect SYBR Green PCR assay from Qiagen. In this assay, total RNA is first isolated from a sample. Total RNA is subsequently poly-adenylated at the 3'-end and reverse transcribed using a universal primer with poly-dT at the 5'-end. In some embodiments, a single reverse transcription reaction is sufficient to assay multiple target RNAs. Real-time RT-PCR is then accomplished using target RNA-specific primers and an miScript Universal Primer, which comprises a poly-dT sequence at the 5'-end. SYBR Green dye binds non-specifically to double-stranded DNA and upon excitation, emits light. In some embodiments, buffer conditions that promote highly-specific annealing of primers to the PCR template (e.g., available in the QuantiTect SYBR Green PCR Kit from Qiagen) can be used to avoid the formation of non-specific DNA duplexes and primer dimers that will bind SYBR Green and negatively affect quantitation. Thus, as PCR product accumulates, the signal from SYBR Green increases, allowing quantitation of specific products.

Real-time RT-PCR is performed using any RT-PCR instrumentation available in the art. Typically, instrumentation used in real-time RT-PCR data collection and analysis comprises a thermal cycler, optics for fluorescence excitation and emission collection, and optionally a computer and data acquisition and analysis software.

In some embodiments, the analytical method used in the methods described herein is a DASL® (cDNA-mediated Annealing, Selection, Extension, and Ligation) Assay, such as the MicroRNA Expression Profiling Assay available from Illumina, Inc. (See illumina.com/downloadds/MicroRNAAssayWorkflow.pdf). In some embodiments, total RNA is isolated from a sample to be analyzed by any method. Additionally, in some embodiments, small RNAs are isolated from a sample to be analyzed by any method. Total RNA or isolated small RNAs may then be polyadenylated (>18A residues are added to the 3'-ends of the RNAs in the reaction mixture). The RNA is reverse transcribed using a biotin-labeled DNA primer that comprises from the 5' to the 3' end, a sequence that includes a PCR primer site and a poly-dT region that binds to the poly-dA tail of the sample RNA. The resulting biotinylated cDNA transcripts are then hybridized to a solid support via a biotin-streptavidin interaction and contacted with one or more target RNA-specific polynucleotides. The target RNA-specific polynucleotides comprise, from the 5'-end to the 3'-end, a region comprising a PCR primer site, region comprising an address sequence, and a target RNA-specific sequence.

In some DASL® embodiments, the target RNA-specific sequence comprises at least 8, at least 9, at least 10, at least 11, at least 12, at least 13, at least 14, at least 15, at least 16, at least 17, at least 18, at least 19 contiguous nucleotides having a sequence that is complementary to at least 8, at least 9, at least 10, at least 11, at least 12, at least 13, at least 14, at least 15, at least 16, at least 17, at least 18, at least 19 contiguous nucleotides of at least one RNA selected from small U2, miR-720, miR-451, 13207, and 13750. In some DASL® embodiments, the target RNA-specific sequence comprises at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides having a sequence that is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of another target RNA.

After hybridization, the target RNA-specific polynucleotide is extended, and the extended products are then eluted from the immobilized cDNA array. A second PCR reaction using a fluorescently-labeled universal primer generates a fluorescently-labeled DNA comprising the target RNA-specific sequence. The labeled PCR products are then hybridized to a microbead array for detection and quantitation.

In some embodiments, the analytical method used for detecting and quantifying the levels of the at least one target RNA, including at least one RNA selected from small U2, miR-720, miR-451, 13207, and 13750, in the methods described herein is a bead-based flow cytometric assay. See Lu J. et al. (2005) Nature 435:834-838, which is incorporated herein by reference in its entirety. An example of a bead-based flow cytometric assay is the xMAP® technology of Luminex, Inc. (See luminexcorp.com/technology/index.html). In some embodiments, total RNA is isolated from a sample and is then labeled with biotin. The labeled RNA is then hybridized to target RNA-specific capture probes (e.g., FlexmiR™ products sold by Luminex, Inc. at luminexcorp.com/products/assays/index.html) that are covalently bound to microbeads, each of which is labeled with 2 dyes having different fluorescence intensities. A streptavidin-bound reporter molecule (e.g., streptavidin-phycoerythrin, also known as "SAPE") is attached to the captured target RNA and the unique signal of each bead is read using flow cytometry. In some embodiments, the RNA sample (total RNA or enriched small RNAs) is first polyadenylated, and is subsequently labeled with a biotinylated 3DNA™ dendrimer (i.e., a multiple-arm DNA with numerous biotin molecules bound thereto), such as those sold by Marligen Biosciences as the Vantage™ microRNA Labeling Kit, using a bridging polynucleotide that is complementary to the 3'-end of the poly-dA tail of the sample RNA and to the 5'-end of the polynucleotide attached to the biotinylated dendrimer. The streptavidin-bound reporter molecule is then attached to the biotinylated dendrimer before analysis by flow cytometry. See marligen.com/vantage-microrna-labeling-kit.html. In some embodiments, biotin-labeled RNA is first exposed to SAPE, and the RNA/SAPE complex is subsequently exposed to an anti-phycoerythrin antibody attached to a DNA dendrimer, which can be bound to as many as 900 biotin molecules. This allows multiple SAPE molecules to bind to the biotinylated dendrimer through the biotin-streptavidin interaction, thus increasing the signal from the assay.

In some embodiments, the analytical method used for detecting and quantifying the levels of the at least one target RNA, including at least one RNA selected from small U2, miR-720, miR-451, 13207, and 13750, in the methods described herein is by gel electrophoresis and detection with labeled probes (e.g., probes labeled with a radioactive or chemiluminescent label), such as by Northern blotting. In some embodiments, total RNA is isolated from the sample, and then is size-separated by SDS polyacrylamide gel electrophoresis. The separated RNA is then blotted onto a membrane and hybridized to radiolabeled complementary probes. In some embodiments, exemplary probes contain one or more affinity-enhancing nucleotide analogs as discussed below, such as locked nucleic acid ("LNA") analogs, which contain a bicyclic sugar moiety instead of deoxyribose or ribose sugars. See, e.g., Várallyay, E. et al. (2008) Nature Protocols 3(2):190-196, which is incorporated herein by reference in its entirety. In some embodiments, the total RNA sample can be further purified to enrich for small RNAs. In some embodiments, target RNAs can be amplified by, e.g., rolling circle amplification using a long probe that is complementary to both ends of a target RNA ("padlocked probes"), ligation to circularize the probe followed by rolling circle replication using the target RNA hybridized to the circularized probe as a primer. See, e.g., Jonstrup, S. P. et al. (2006) RNA 12:1-6, which is incorporated herein by reference in its entirety. The amplified product can then be detected and quantified using, e.g., gel electrophoresis and Northern blotting.

In alternative embodiments, labeled probes are hybridized to isolated total RNA in solution, after which the RNA is subjected to rapid ribonuclease digestion of single-stranded RNA, e.g., unhybridized portions of the probes or unhybridized target RNAs. In these embodiments, the ribonuclease treated sample is then analyzed by SDS-PAGE and detection of the radiolabeled probes by, e.g., Northern blotting. See mirVana™ miRNA Detection Kit sold by Applied Biosystems, Inc. product literature at ambion.com/catalog/CatNum.php?1552.

In some embodiments, the analytical method used for detecting and quantifying the at least one target RNA, including at least one RNA selected from small U2, miR-720, miR-451, 13207, and 13750, in the methods described herein is by hybridization to a microarray. See, e.g., Liu, C. G. et al. (2004) Proc. Nat'l Acad. Sci. USA 101:9740-9744; Lim, L. P. et al. (2005) Nature 433:769-773, each of which is incorporated herein by reference in its entirety, and Example 1.

In some embodiments, detection and quantification of a target RNA using a microarray is accomplished by surface plasmon resonance. See, e.g., Nanotech News (2006), available at nano.cancer.gov/news_center/nanotech_news_2006-10-30b.asp. In these embodiments, total RNA is isolated from a sample being tested. Optionally, the RNA sample is further purified to enrich the population of small RNAs. After purification, the RNA sample is bound to an addressable microarray containing probes at defined locations on the microarray. In some embodiments, the RNA is reverse transcribed to cDNA, and the cDNA is bound to an addressable microarray. In some such embodiments the microarray comprises probes that have regions that are complementary to the cDNA sequence (i.e., the probes comprise regions that have the same sequence as the RNA to be detected). Nonlimiting exemplary capture probes comprise a region comprising a sequence selected from (for each probe, it is indicated whether the probe hybridizes to the "sense" mature RNA, or the "antisense" of the mature RNA (i.e., hybridizes to a cDNA reverse-transcribed from the RNA)):

```
for small U2, sense
                                    (SEQ ID NO: 42)
5'-CCCTGCTCCAAAAATCCA-3';

for small U2, antisense
                                    (SEQ ID NO: 43)
5'-TGGATTTTTGGAGCAGGG-3';

for miR-720, sense
                                    (SEQ ID NO: 44)
5'-TGGAGGCCCCAGCGAGA-3';

for miR-720, antisense
                                    (SEQ ID NO: 45)
5'-TCTCGCTGGGGCCTCCA-3';

for miR-451, sense
                                    (SEQ ID NO: 46)
5'-AACTCAGTAATGGTAACGGTTT-3';

for miR-451, antisense
                                    (SEQ ID NO: 47)
5'-AAACCGTTACCATTACTGAGTT-3';

for 13207, sense
                                    (SEQ ID NO: 48)
5'-CCTGCTCCAACAAGGAAAGACA-3';

for 13207, antisense
                                    (SEQ ID NO: 49)
5'-TGTCTTTCCTTGTTGGAGCAGG-3';

for 13207, sense
                                    (SEQ ID NO: 81)
5'-GCTCCAACAAGGAAAGACAGGA-3';

for 13207, antisense
                                    (SEQ ID NO: 82)
5'-TCCTGTCTTTCCTTGTTGGAGC-3';

for 13750, sense
                                    (SEQ ID NO: 50)
5'-AGCTTCCTGCTCCCTGCTCTACA-3';
and for 13750, antisense
                                    (SEQ ID NO: 51)
5'-TGTAGAGCAGGGAGCAGGAAGCT-3'.
```

Further nonlimiting exemplary probes comprise a region having at least 8, at least 9, at least 10, at least 11, at least 12, at least 13, at least 14, at least 15, at least 16, at least 17, or at least 18 contiguous nucleotides of a sequence selected from SEQ ID NOs: 42 to 51, 81, and 82. A probe may further comprise at least a second region that does not comprise a sequence that is identical to at least 8 contiguous nucleotides of a sequence selected from SEQ ID NOs: 42 to 51, 81, and 82.

Nonlimiting exemplary probes comprise a region having at least 8, at least 9, at least 10, at least 11, at least 12, at least 13, at least 14, at least 15, at least 16, at least 17, or at least 18, at least 19, at least 20, at least 25, at least 30, at least 40, at least 50, at least 60, or at least 70 contiguous nucleotides of a sequence selected from (for each probe, it is indicated whether the probe hybridizes to the "sense" RNA, or the "antisense" of the RNA (i.e., hybridizes to a cDNA reverse-transcribed from the RNA))::

```
for small U2, sense
                                    (SEQ ID NO: 52)
5'-GGGTGCACCG TTCCTGGAGG TACTGCAATA CCAGGTCGAT

GCGTGGAGTG GACGGAGCAA GCTCCTATTC CATCTCCCTG

CTCCAAAAAT CCATTTAATA TATTGTCCTC GGATAGAGGA
```

-continued

CGTATCAGAT ATTAAACTGA TAAGAACAGA TACTACACTT

GATCTTAGCC AAAAGGCCGA GAAGCGAT-3';

for small U2, antisense
(SEQ ID NO: 53)
5'-ATCGCTTCTC GGCCTTTTGG CTAAGATCAA GTGTAGTATC

TGTTCTTATC AGTTTAATAT CTGATACGTC CTCTATCCGA

GGACAATATA TTAAATGGAT TTTTGGAGCA GGGAGATGGA

ATAGGAGCTT GCTCCGTCCA CTCCACGCAT CGACCTGGTA

TTGCAGTACC TCCAGGAACG GTGCACCC-3';

for miR-720, sense
(SEQ ID NO: 54)
5'-CTAATAAAGG ACTCTTAATT CATCTCAAAG TGTGGTGTTT

TCTCTAACAC CCCTGGGCAC AACATTTTGG AGGCCCCAGC

GAGATATTAA CACCACCGTG TGAGATCCGG-3';

for miR-720, antisense
(SEQ ID NO: 55)
5'-CCGGATCTCA CACGGTGGTG TTAATATCTC GCTGGGGCCT

CCAAAATGTT GTGCCCAGGG GTGTTAGAGA AAACACCACA

CTTTGAGATG AATTAAGAGT CCTTTATTAG-3';

for miR-451, sense
(SEQ ID NO: 56)
5'-TCTGGGTATA GCAAGAGAAC CATTACCATT ACTAAACTCA

GTAATGGTAA CGGTTTCCTT GCCATTCCCA AG-3';

for miR-451, antisense
(SEQ ID NO: 57)
5'-CTTGGGAATG GCAAGGAAAC CGTTACCATT ACTGAGTTTA

GTAATGGTAA TGGTTCTCTT GCTATACCCA GA-3';

for 13207, sense
(SEQ ID NO: 58)
5'-CTGCGGCAAG TGCTTCTACA TCCCTGCTCC AACAAGGAAA

GACAGGAGGC CAGGCGTGTG TGTGGCTCAC ACCTCTTGTC

CTTCCTTGTT GGGGCAGGGG TACAGAAGCA TTTTGGGGGG C-3';

for 13207, antisense
(SEQ ID NO: 59)
5'-GCCCCCCAAA ATGCTTCTGT ACCCCTGCCC CAACAAGGAA

GGACAAGAGG TGTGAGCCAC ACACACGCCT GGCCTCCTGT

CTTTCCTTGT TGGAGCAGGG ATGTAGAAGC ACTTGCCGCA G-3';

for 13750, sense
(SEQ ID NO: 60)
5'-AGCACTGTGA GGGGCTGGGG GCAGAACAGG ACAGGTCAGG

GCTGGACACA CACAGCTTCC TGCTCCCTGC TCTACAGCTC

CCTCGCAGGC C-3';
and for 13750, antisense
(SEQ ID NO: 61)
5'-GGCCTGCGAG GGAGCTGTAG AGCAGGGAGC AGGAAGCTGT

GTGTGTCCAG CCCTGACCTG TCCTGTTCTG CCCCCAGCCC

CTCACAGTGC T-3'.

In some embodiments, the probes contain one or more affinity-enhancing nucleotide analogs as discussed below, such as locked nucleic acid ("LNA") nucleotide analogs.

After hybridization to the microarray, the RNA that is hybridized to the array is first polyadenylated, and the array is then exposed to gold particles having poly-dT bound to them. The amount of bound target RNA is quantitated using surface plasmon resonance.

In some embodiments, microarrays are utilized in a RNA-primed, Array-based Klenow Enzyme ("RAKE") assay. See Nelson, P. T. et al. (2004) Nature Methods 1(2):1-7; Nelson, P. T. et al. (2006) RNA 12(2):1-5, each of which is incorporated herein by reference in its entirety. In some embodiments, total RNA is isolated from a sample. In some embodiments, small RNAs are isolated from a sample. The RNA sample is then hybridized to DNA probes immobilized at the 5'-end on an addressable array. The DNA probes comprise, in some embodiments, from the 5'-end to the 3'-end, a first region comprising a "spacer" sequence which is the same for all probes, a second region comprising three thymidine-containing nucleosides, and a third region comprising a sequence that is complementary to a target RNA of interest, such as at least one RNA selected from small U2, miR-720, miR-451, 13207, and 13750.

After the sample is hybridized to the array, it is exposed to exonuclease I to digest any unhybridized probes. The Klenow fragment of DNA polymerase I is then applied along with biotinylated dATP, allowing the hybridized target RNAs to act as primers for the enzyme with the DNA probe as template. The slide is then washed and a streptavidin-conjugated fluorophore is applied to detect and quantitate the spots on the array containing hybridized and Klenow-extended target RNAs from the sample.

In some embodiments, the RNA sample is reverse transcribed. In some embodiments, the RNA sample is reverse transcribed using a biotin/poly-dA random octamer primer. When than primer is used, the RNA template is digested and the biotin-containing cDNA is hybridized to an addressable microarray with bound probes that permit specific detection of target RNAs. In typical embodiments, the microarray includes at least one probe comprising at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides identically present in, or complementary to a region of, a target RNA, such as at least one RNA selected from small U2, miR-720, miR-451, 13207, and 13750. After hybridization of the cDNA to the microarray, the microarray is exposed to a streptavidin-bound detectable marker, such as a fluorescent dye, and the bound cDNA is detected. See Liu C. G. et al. (2008) Methods 44:22-30, which is incorporated herein by reference in its entirety.

In some embodiments, target RNAs, including small U2, miR-720, miR-451, 13207, and 13750, are detected and quantified in an ELISA-like assay using probes bound in the wells of microtiter plates. See Mora J. R. and Getts R. C. (2006) BioTechniques 41:420-424 and supplementary material in BioTechniques 41(4):1-5; U.S. Patent Publication No. 2006/0094025 to Getts et al., each of which is incorporated by reference herein in its entirety. In these embodiments, a sample of RNA that is enriched in small RNAs is either polyadenylated, or is reverse transcribed and the cDNA is polyadenylated. The RNA or cDNA is hybridized to probes immobilized in the wells of a microtiter plates, wherein each of the probes comprises a sequence that is identically present in, or complementary to a region of, a target RNA, such as at least one RNA selected from small U2, miR-720, miR-451, 13207, and 13750. In some embodiments, the hybridized RNAs are labeled using a capture sequence, such as a DNA dendrimer (such as those available from Genisphere, Inc., genisphere.com/about_3dna.html) that is labeled with a plurality of biotin molecules or with a plurality of horseradish peroxidase molecules, and a bridging polynucleotide that contains a poly-dT sequence at the 5'-end that binds to the poly-dA tail of the captured nucleic acid, and a sequence at the 3'-end that is complementary to a region of the capture sequence. If the capture sequence is biotinylated, the microarray is then exposed to streptavidin-bound horseradish peroxidase. Hybridization of target RNAs is detected by the addition of a horseradish peroxidase substrate such as tetramethylbenzidine (TMB) and measurement of the absorbance of the solution at 450 nM.

In still other embodiments, an addressable microarray is used to detect a target RNA using quantum dots. See Liang, R. Q. et al. (2005) Nucl. Acids Res. 33(2):e17, available at pubmedcentral.nih.gov/articlerender.fcgi?artid=548377, which is incorporated herein by reference in its entirety. In some embodiments, total RNA is isolated from a sample. In some embodiments, small RNAs are isolated from the sample. The 3'-ends of the target RNAs are biotinylated using biotin-X-hydrazide. The biotinylated target RNAs are captured on a microarray comprising immobilized probes comprising sequences that are identically present in, or complementary to a region of, target RNAs, including small U2, miR-720, miR-451, 13207, and 13750. The hybridized target RNAs are then labeled with quantum dots via a biotin-streptavidin binding. A confocal laser causes the quantum dots to fluoresce and the signal can be quantified. In alternative embodiments, small RNAs can be detected using a colorimetric assay. In these embodiments, small RNAs are labeled with streptavidin-conjugated gold followed by silver enhancement. The gold nanoparticles bound to the hybridized target RNAs catalyze the reduction of silver ions to metallic silver, which can then be detected colorimetrically with a CCD camera.

In some embodiments, detection and quantification of one or more target RNAs is accomplished using microfluidic devices and single-molecule detection. In some embodiments, target RNAs in a sample of isolated total RNA are hybridized to two probes, one which is complementary to nucleic acids at the 5'-end of the target RNA and the second which is complementary to the 3'-end of the target RNA. Each probe comprises, in some embodiments, one or more affinity-enhancing nucleotide analogs, such as LNA nucleotide analogs and each is labeled with a different fluorescent dye having different fluorescence emission spectra. The sample is then flowed through a microfluidic capillary in which multiple lasers excite the fluorescent probes, such that a unique coincident burst of photons identifies a particular target RNA, and the number of particular unique coincident bursts of photons can be counted to quantify the amount of the target RNA in the sample. See U.S. Patent Publication No. 2006/0292616 to Neely et al., which is hereby incorporated by reference in its entirety. In some alternative embodiments, a target RNA-specific probe can be labeled with 3 or more distinct labels selected from, e.g., fluorophores, electron spin labels, etc., and then hybridized to an RNA sample, such as total RNA, or a sample that is enriched in small RNAs. Non-limiting exemplary target RNA-specific probes include probes comprising sequences selected from SEQ ID NOs: 42 to 61, 81, and 82; sequences having at least 8, at least 9, at least 10, at least 11, at least 12, at least 13, at least 14, at least 15, at least 16, at least 17, or at least 18 contiguous nucleotides of a sequence selected from SEQ ID NOs: 42 to 51, 81, and 82; and sequences having at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, or at least 70 contiguous nucleotides of a sequence selected from SEQ ID NOs: 52 to 61.

Optionally, the sample RNA is modified before hybridization. The target RNA/probe duplex is then passed through channels in a microfluidic device and that comprise detectors that record the unique signal of the 3 labels. In this way, individual molecules are detected by their unique signal and counted. See U.S. Pat. Nos. 7,402,422 and 7,351,538 to Fuchs et al., U.S. Genomics, Inc., each of which is incorporated herein by reference in its entirety.

In some embodiments, the detection and quantification of one or more target RNAs is accomplished by a solution-based assay, such as a modified Invader assay. See Allawi H. T. et al. (2004) RNA 10:1153-1161, which is incorporated herein by reference in its entirety. In some embodiments, the modified invader assay can be performed on unfractionated detergent lysates of cervical cells. In other embodiments, the modified invader assay can be performed on total RNA isolated from cells or on a sample enriched in small RNAs. The target RNAs in a sample are annealed to two probes which form hairpin structures. A first probe has a hairpin structure at the 5' end and a region at the 3'-end that has a sequence that is complementary to the sequence of a region at the 5'-end of a target RNA. The 3'-end of the first probe is the "invasive polynucleotide". A second probe has, from the 5' end to the 3'-end a first "flap" region that is not complementary to the target RNA, a second region that has a sequence that is complementary to the 3'-end of the target RNA, and a third region that forms a hairpin structure. When the two probes are bound to a target RNA target, they create an overlapping configuration of the probes on the target RNA template, which is recognized by the Cleavase enzyme, which releases the flap of the second probe into solution. The flap region then binds to a complementary region at the 3'-end of a secondary reaction template ("SRT"). A FRET polynucleotide (having a fluorescent dye bound to the 5'-end and a quencher that quenches the dye bound closer to the 3' end) binds to a complementary region at the 5'-end of the SRT, with the result that an overlapping configuration of the 3'-end of the flap and the 5'-end of the FRET polynucleotide is created. Cleavase recognizes the overlapping configuration and cleaves the 5'-end of the FRET polynucleotide, generates a fluorescent signal when the dye is released into solution.

4.1.5. Exemplary Polynucleotides

In some embodiments, polynucleotides are provided. In some embodiments, synthetic polynucleotides are provided. Synthetic polynucleotides, as used herein, refer to polynucleotides that have been synthesized in vitro either chemically or enzymatically. Chemical synthesis of polynucleotides includes, but is not limited to, synthesis using polynucleotide synthesizers, such as OligoPilot (GE Healthcare), ABI 3900 DNA Synthesizer (Applied Biosystems), and the like. Enzymatic synthesis includes, but is not limited to, producing polynucleotides by enzymatic amplification, e.g., PCR.

In some embodiments, a polynucleotide is provided that comprises at least 8, at least 9, at least 10, at least 11, at least 12, at least 13, at least 14, at least 15, at least 16, at least 17, or at least 18 contiguous nucleotides of a sequence selected from SEQ ID NOs: 42 to 51, 81, and 82. In some embodiments, a polynucleotide is provided that comprises at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, or at least 70 contiguous nucleotides of a sequence selected from SEQ ID NOs: 52 to 61.

In various embodiments, a polynucleotide comprises fewer than 500, fewer than 300, fewer than 200, fewer than 150, fewer than 100, fewer than 75, fewer than 50, fewer than 40, or fewer than 30 nucleotides. In various embodiments, a polynucleotide is between 8 and 200, between 8 and 150, between 8 and 100, between 8 and 75, between 8 and 50, between 8 and 40, or between 8 and 30 nucleotides long.

In some embodiments, the polynucleotide is a primer. In some embodiments, the primer is labeled with a detectable moiety. In some embodiments, a primer is not labeled. A primer, as used herein, is a polynucleotide that is capable of specifically hybridizing to a target RNA or to a cDNA reverse transcribed from the target RNA or to an amplicon that has been amplified from a target RNA or a cDNA (collectively referred to as "template"), and, in the presence of the template, a polymerase and suitable buffers and reagents, can be extended to form a primer extension product.

In some embodiments, the polynucleotide is a probe. In some embodiments, the probe is labeled with a detectable moiety. A detectable moiety, as used herein, includes both directly detectable moieties, such as fluorescent dyes, and indirectly detectable moieties, such as members of binding pairs. When the detectable moiety is a member of a binding pair, in some embodiments, the probe can be detectable by incubating the probe with a detectable label bound to the second member of the binding pair. In some embodiments, a probe is not labeled, such as when a probe is a capture probe, e.g., on a microarray or bead. In some embodiments, a probe is not extendable, e.g., by a polymerase. In other embodiments, a probe is extendable.

In some embodiments, the polynucleotide is a FRET probe that in some embodiments is labeled at the 5'-end with a fluorescent dye (donor) and at the 3'-end with a quencher (acceptor), a chemical group that absorbs (i.e., suppresses) fluorescence emission from the dye when the groups are in close proximity (i.e., attached to the same probe). In other embodiments, the donor and acceptor are not at the ends of the FRET probe. Thus, in some embodiments, the emission spectrum of the donor moiety should overlap considerably with the absorption spectrum of the acceptor moiety.

4.1.5.1. Exemplary Polynucleotide Modifications

In some embodiments, the methods of detecting at least one target RNA described herein employ one or more polynucleotides that have been modified, such as polynucleotides comprising one or more affinity-enhancing nucleotide analogs. Modified polynucleotides useful in the methods described herein include primers for reverse transcription, PCR amplification primers, and probes. In some embodiments, the incorporation of affinity-enhancing nucleotides increases the binding affinity and specificity of a polynucleotide for its target nucleic acid as compared to polynucleotides that contain only deoxyribonucleotides, and allows for the use of shorter polynucleotides or for shorter regions of complementarity between the polynucleotide and the target nucleic acid.

In some embodiments, affinity-enhancing nucleotide analogs include nucleotides comprising one or more base modifications, sugar modifications and/or backbone modifications.

In some embodiments, modified bases for use in affinity-enhancing nucleotide analogs include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In some embodiments, affinity-enhancing nucleotide analogs include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In some embodiments, affinity-enhancing nucleotide analogs include backbone modifications such as the use of peptide nucleic acids (PNA; e.g., an oligomer including nucleobases linked together by an amino acid backbone). Other backbone modifications include phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, a polynucleotide includes at least one affinity-enhancing nucleotide analog that has a modified base, at least nucleotide (which may be the same nucleotide) that has a modified sugar, and/or at least one internucleotide linkage that is non-naturally occurring.

In some embodiments, an affinity-enhancing nucleotide analog contains a locked nucleic acid ("LNA") sugar, which is a bicyclic sugar. In some embodiments, a polynucleotide for use in the methods described herein comprises one or more nucleotides having an LNA sugar. In some embodiments, a polynucleotide contains one or more regions consisting of nucleotides with LNA sugars. In other embodiments, a polynucleotide contains nucleotides with LNA sugars interspersed with deoxyribonucleotides. See, e.g., Frieden, M. et al. (2008) Curr. Pharm. Des. 14(11):1138-1142.

4.1.5.2. Exemplary Primers

In some embodiments, a primer is provided. In some embodiments, a primer is identical or complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of a target RNA, such as small U2, miR-720, miR-451, 13207, or 13750. In some embodiments, a primer may also comprise portions or regions that are not identical or complementary to the target RNA. In some embodiments, a region of a primer that is identical or complementary to a target RNA is contiguous, such that any region of a primer that is not identical or complementary to the target RNA does not disrupt the identical or complementary region.

In some embodiments, a primer comprises a portion that is identically present in a target RNA, such as at least one RNA selected from small U2, miR-720, miR-451, 13207, and 13750. In some such embodiments, a primer that comprises a region that is identically present in the target RNA is capable of selectively hybridizing to a cDNA that has been reverse transcribed from the RNA, or to an amplicon that has been produced by amplification of the target RNA or cDNA. In some embodiments, the primer is complementary to a sufficient portion of the cDNA or amplicon such that it selectively hybridizes to the cDNA or amplicon under the conditions of the particular assay being used.

As used herein, "selectively hybridize" means that a polynucleotide, such as a primer or probe, will hybridize to a particular nucleic acid in a sample with at least 5-fold greater affinity than it will hybridize to another nucleic acid present in the same sample that has a different nucleotide sequence in the hybridizing region. Exemplary hybridization conditions are discussed, e.g., in Example 1. In some embodiments, a polynucleotide will hybridize to a particular nucleic acid in a sample with at least 10-fold greater affinity than it will hybridize to another nucleic acid present in the same sample that has a different nucleotide sequence in the hybridizing region.

Nonlimiting exemplary primers include primers comprising sequences that are identically present in, or complementary to a region of, at least one RNA selected from small U2, miR-720, miR-451, 13207, and 13750, or another target RNA. Nonlimiting exemplary primers include polynucleotides comprising sequences selected from SEQ ID NOs: 42 to 61, 81, and 82; sequences having at least 8, at least 9, at least 10, at least 11, at least 12, at least 13, at least 14, at least 15, at least 16, at least 17, or at least 18 contiguous nucleotides of a sequence selected from SEQ ID NOs: 42 to 51, 81, and 82; and sequences having at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, or at least 70 contiguous nucleotides of a sequence selected from SEQ ID NOs: 52 to 61.

In some embodiments, a primer is used to reverse transcribe a target RNA, for example, as discussed herein. In some embodiments, a primer is used to amplify a target RNA or a cDNA reverse transcribed therefrom. Such amplification, in some embodiments, is quantitative PCR, for example, as discussed herein. In some embodiments, a primer comprises a detectable moiety.

4.1.5.3. Exemplary Probes

In various embodiments, methods of detecting the presence of a lung cancer comprise hybridizing nucleic acids of a sample with a probe. In some embodiments, the probe comprises a portion that is complementary to a target RNA, such as small U2, miR-720, miR-451, 13207, and 13750. In some embodiments, the probe comprises a portion that is identically present in the target RNA, such as small U2, miR-720, miR-451, 13207, and 13750. In some such embodiments, a probe that is complementary to a target RNA is complementary to a sufficient portion of the target RNA such that it selectively hybridizes to the target RNA under the conditions of the particular assay being used. In some embodiments, a probe that is complementary to a target RNA is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the target RNA. In some embodiments, a probe that is complementary to a target RNA comprises a region that is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the target RNA. That is, a probe that is complementary to a target RNA may also comprise portions or regions that are not complementary to the target RNA. In some embodiments, a region of a probe that is complementary to a target RNA is contiguous, such that any region of a probe that is not complementary to the target RNA does not disrupt the complementary region.

In some embodiments, the probe comprises a portion that is identically present in the target RNA, such as small U2, miR-720, miR-451, 13207, and 13750. In some such embodiments, a probe that comprises a region that is identically present in the target RNA is capable of selectively hybridizing to a cDNA that has been reverse transcribed from the RNA, or to an amplicon that has been produced by amplification of the target RNA or cDNA. In some embodiments, the probe is complementary to a sufficient portion of the cDNA or amplicon such that it selectively hybridizes to the cDNA or amplicon under the conditions of the particular assay being used. In some embodiments, a probe that is complementary to a cDNA or amplicon is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the cDNA or amplicon. In some embodiments, a probe that is complementary to a target RNA comprises a region that is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the cDNA or amplicon. That is, a probe that is complementary to a cDNA or amplicon may also comprise portions or regions that are not complementary to the cDNA or amplicon. In some embodiments, a region of a probe that is complementary to a cDNA or amplicon is contiguous, such that any region of a probe that is not complementary to the cDNA or amplicon does not disrupt the complementary region.

Nonlimiting exemplary probes include probes comprising sequences set forth in SEQ ID NOS: 42 to 61, and probes comprising at least 8, at least 9, at least 10, at least 11, at least 12, at least 13, at least 14, at least 15, at least 16, at least 17, or at least 18 contiguous nucleotides of a sequence selected from SEQ ID NOs: 42 to 51, 81, and 82. Nonlimiting exemplary probes include probes comprising sequences set forth in SEQ ID NOS: 52 to 61, and probes comprising at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, or at least 70 contiguous nucleotides of a sequence selected from SEQ ID NOs: 52 to 61.

In some embodiments, the method of detectably quantifying one or more target RNAs comprises: (a) isolating total RNA; (b) reverse transcribing a target RNA to produce a cDNA that is complementary to the target RNA; (c) amplifying the cDNA from (b); and (d) detecting the amount of a target RNA using real time RT-PCR and a detection probe.

As described above, in some embodiments, the real time RT-PCR detection is performed using a FRET probe, which includes, but is not limited to, a TaqMan® probe, a Molecular beacon probe and a Scorpion probe. In some embodiments, the real time RT-PCR detection and quantification is performed with a TaqMan® probe, i.e., a linear probe that typically has a fluorescent dye covalently bound at one end of the DNA and a quencher molecule covalently bound at the other end of the DNA. The FRET probe comprises a sequence that is complementary to a region of the cDNA such that, when the FRET probe is hybridized to the cDNA, the dye fluorescence is quenched, and when the probe is digested during amplification of the cDNA, the dye is released from the probe and produces a fluorescence signal. In such embodiments, the amount of target RNA in the sample is proportional to the amount of fluorescence measured during cDNA amplification.

The TaqMan® probe typically comprises a region of contiguous nucleotides having a sequence that is complementary to a region of a target RNA or its complementary cDNA that is reverse transcribed from the target RNA template (i.e., the sequence of the probe region is complementary to or identically present in the target RNA to be detected) such that the probe is specifically hybridizable to the resulting PCR amplicon. In some embodiments, the probe comprises a region of at least 6 contiguous nucleotides having a sequence that is fully complementary to or identically present in a region of a cDNA that has been reverse transcribed from a target RNA template, such as comprising a region of at least 8 contiguous nucleotides, at least 10 contiguous nucleotides, at least 12 contiguous nucleotides, at least 14 contiguous nucleotides, or at least 16 contiguous nucleotides having a sequence that is complementary to or identically present in a region of a cDNA reverse transcribed from a target RNA to be detected.

In some embodiments, the region of the cDNA that has a sequence that is complementary to the TaqMan® probe sequence is at or near the center of the cDNA molecule. In some embodiments, there are independently at least 2 nucleotides, such as at least 3 nucleotides, such as at least 4 nucleotides, such as at least 5 nucleotides of the cDNA at the 5'-end and at the 3'-end of the region of complementarity.

In some embodiments, Molecular Beacons can be used to detect and quantitate PCR products. Like TaqMan® probes, Molecular Beacons use FRET to detect and quantitate a PCR product via a probe having a fluorescent dye and a quencher attached at the ends of the probe. Unlike TaqMan® probes, Molecular Beacons remain intact during the PCR cycles. Molecular Beacon probes form a stem-loop structure when free in solution, thereby allowing the dye and quencher to be in close enough proximity to cause fluorescence quenching. When the Molecular Beacon hybridizes to a target, the stem-loop structure is abolished so that the dye and the quencher become separated in space and the dye fluoresces. Molecular Beacons are available, e.g., from Gene Link™ (see genelink.com/newsite/products/mbintro.asp).

In some embodiments, Scorpion probes can be used as both sequence-specific primers and for PCR product detection and quantitation. Like Molecular Beacons, Scorpion probes form a stem-loop structure when not hybridized to a target nucleic acid. However, unlike Molecular Beacons, a Scorpion probe achieves both sequence-specific priming and PCR product detection. A fluorescent dye molecule is attached to the 5'-end of the Scorpion probe, and a quencher is attached to the 3'-end. The 3' portion of the probe is complementary to the extension product of the PCR primer, and this complementary portion is linked to the 5'-end of the probe by a non-amplifiable moiety. After the Scorpion primer is extended, the target-specific sequence of the probe binds to its complement within the extended amplicon, thus opening up the stem-loop structure and allowing the dye on the 5'-end to fluoresce and generate a signal. Scorpion probes are available from, e.g., Premier Biosoft International (see premierbiosoft.com/tech_notes/Scorpion.html).

In some embodiments, labels that can be used on the FRET probes include colorimetric and fluorescent labels such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides useful in the preparation of RT-PCR probes for use in some embodiments of the methods described herein are available from Molecular Probes (Invitrogen), and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences (GE Healthcare), such as Cy3-UTP and Cy5-UTP.

Examples of fluorescently labeled deoxyribonucleotides useful in the preparation of RT-PCR probes for use in the methods described herein include Dinitrophenyl (DNP)-1'-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. Fluorescently labeled nucleotides are commercially available and can be purchased from, e.g., Invitrogen.

In some embodiments, dyes and other moieties, such as quenchers, are introduced into polynucleotide used in the methods described herein, such as FRET probes, via modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into a polynucleotide, for example, by way of solid phase synthesis of the polynucleotide. In other embodiments, the modified nucleotide includes one or more reactive groups that can react with a dye or quencher before, during, or after incorporation of the modified nucleotide into the nucleic acid. In specific embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In specific embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink.

Exemplary detectable moieties also include, but are not limited to, members of binding pairs. In some such embodiments, a first member of a binding pair is linked to a polynucleotide. The second member of the binding pair is linked to a detectable label, such as a fluorescent label. When the polynucleotide linked to the first member of the binding pair is incubated with the second member of the binding pair linked to the detectable label, the first and second members of the binding pair associate and the polynucleotide can be detected. Exemplary binding pairs include, but are not limited to, biotin and streptavidin, antibodies and antigens, etc.

In some embodiments, multiple target RNAs are detected in a single multiplex reaction. In some such embodiments, each probe that is targeted to a unique cDNA is spectrally distinguishable when released from the probe. Thus, each target RNA is detected by a unique fluorescence signal.

One skilled in the art can select a suitable detection method for a selected assay, e.g., a real-time RT-PCR assay. The selected detection method need not be a method described above, and may be any method.

4.2. Exemplary Compositions and Kits

In another aspect, compositions are provided. In some embodiments, compositions are provided for use in the methods described herein.

In some embodiments, a composition comprises at least one polynucleotide. In some embodiments, a composition comprises at least one primer. In some embodiments, a composition comprises at least one probe. In some embodiments, a composition comprises at least one primer and at least one probe.

In some embodiments, compositions are provided that comprise at least one target RNA-specific primer. The term "target RNA-specific primer" encompasses primers that have a region of contiguous nucleotides having a sequence that is (i) identically present in a target RNA, such as small U2, miR-720, miR-451, 13207, or 13750, or (ii) complementary to the sequence of a region of contiguous nucleotides found in a target RNA, such as small U2, miR-720, miR-451, 13207, or 13750.

In some embodiments, compositions are provided that comprise at least one target RNA-specific probe. The term "target RNA-specific probe" encompasses probes that have a region of contiguous nucleotides having a sequence that is (i) identically present in a target RNA, such as small U2, miR-720, miR-451, 13207, or 13750, or (ii) complementary to the sequence of a region of contiguous nucleotides found in a target RNA, such as small U2, miR-720, miR-451, 13207, or 13750.

In some embodiments, target RNA-specific primers and probes comprise deoxyribonucleotides. In other embodiments, target RNA-specific primers and probes comprise at least one nucleotide analog. Nonlimiting exemplary nucleotide analogs include, but are not limited to, analogs described herein, including LNA analogs and peptide nucleic acid (PNA) analogs. In some embodiments, target RNA-specific primers and probes comprise at least one nucleotide analog which increases the hybridization binding energy (e.g., an affinity-enhancing nucleotide analog, discussed above). In some embodiments, a target RNA-specific primer or probe in the compositions described herein binds to one target RNA in the sample. In some embodiments, a single primer or probe binds to multiple target RNAs, such as multiple isomirs.

In some embodiments, more than one primer or probe specific for a single target RNA is present in the compositions, the primers or probes capable of binding to overlapping or spatially separated regions of the target RNA.

It will be understood, even if not explicitly stated hereinafter, that in some embodiments in which the compositions described herein are designed to hybridize to cDNAs reverse transcribed from target RNAs, the composition comprises at least one target RNA-specific primer or probe (or region thereof) having a sequence that is identically present in a target RNA (or region thereof).

In some embodiments, a composition comprises a target RNA-specific primer. In some embodiments, the target RNA-specific primer is specific for small U2, miR-720, miR-451, 13207, or 13750. In some embodiments, a composition comprises a plurality of target RNA-specific primers for each of at least 2, at least 3, at least 4, at least 5, at least 6, at least 7, or at least 8 target RNAs.

In some embodiments, a composition comprises a target RNA-specific probe. In some embodiments, the target RNA-specific probe is specific for small U2, miR-720, miR-451, 13207, or 13750. In some embodiments, a composition comprises a plurality of target RNA-specific probes for each of at least 2, at least 3, at least 4, at least 5, at least 6, at least 7, or at least 8 target RNAs.

In some embodiments, a composition is an aqueous composition. In some embodiments, the aqueous composition comprises a buffering component, such as phosphate, tris, HEPES, etc., and/or additional components, as discussed below. In some embodiments, a composition is dry, for example, lyophilized, and suitable for reconstitution by addition of fluid. A dry composition may include a buffering component and/or additional components.

In some embodiments, a composition comprises one or more additional components. Additional components include, but are not limited to, salts, such as NaCl, KCl, and $MgCl_2$; polymerases, including thermostable polymerases; dNTPs; RNase inhibitors; bovine serum albumin (BSA) and the like; reducing agents, such as β-mercaptoethanol; EDTA and the like; etc. One skilled in the art can select suitable composition components depending on the intended use of the composition.

In some embodiments, an addressable microarray component is provided that comprises target RNA-specific probes attached to a substrate.

Microarrays for use in the methods described herein comprise a solid substrate onto which the probes are covalently or non-covalently attached. In some embodiments, probes capable of hybridizing to one or more target RNAs or cDNAs are attached to the substrate at a defined location ("addressable array"). Probes can be attached to the substrate in a wide variety of ways, as will be appreciated by those in the art. In some embodiments, the probes are synthesized first and subsequently attached to the substrate. In other embodiments, the probes are synthesized on the substrate. In some embodiments, probes are synthesized on the substrate surface using techniques such as photopolymerization and photolithography.

In some embodiments, the solid substrate is a material that is modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. In some embodiments, the substrates allow optical detection without appreciably fluorescing.

In some embodiments, the substrate is planar. In other embodiments, probes are placed on the inside surface of a tube, such as for flow-through sample analysis to minimize sample volume. In other embodiments, probes can be in the wells of multi-well plates. In still other embodiments, probes can be attached to an addressable microbead array. In yet other embodiments, the probes can be attached to a flexible substrate, such as a flexible foam, including closed cell foams made of particular plastics.

The substrate and the probe can each be derivatized with functional groups for subsequent attachment of the two. For example, in some embodiments, the substrate is derivatized with one or more chemical functional groups including, but not limited to, amino groups, carboxyl groups, oxo groups and thiol groups. In some embodiments, probes are attached directly to the substrate through one or more functional groups. In some embodiments, probes are attached to the substrate indirectly through a linker (i.e., a region of contiguous nucleotides that space the probe regions involved in hybridization and detection away from the substrate surface). In some embodiments, probes are attached to the solid support through the 5' terminus. In other embodiments, probes are attached through the 3' terminus. In still other embodiments, probes are attached to the substrate through an internal nucleotide. In some embodiments the probe is attached to the solid support non-covalently, e.g., via a biotin-streptavidin interaction, wherein the probe biotinylated and the substrate surface is covalently coated with streptavidin.

In some embodiments, the compositions comprise a microarray having probes attached to a substrate, wherein at least one of the probes (or a region thereof) comprises a sequence that is identically present in, or complementary to a region of, small U2, miR-720, miR-451, miR-13207, or 13750. In some embodiments, in addition to a probe comprising a sequence that is identically present in, or complementary to a region of, at least one of those RNAs, a microarray further comprises at least one probe comprising a sequence that is identically present in, or complementary to a region of, another target RNA. In some embodiments, in addition to a probe comprising a sequence that is identically present in, or complementary to a region of, at least one of those RNAs, a microarray further comprises at least two, at least five, at least 10, at least 15, at least 20, at least 30, at least 50, or at least 100 probes comprising sequences that are identically present in, or complementary to regions of, other target RNAs. In some embodiments, the microarray comprises each target RNA-specific probe at only one location on the microarray. In some embodiments, the microarray comprises at least one target RNA-specific probe at multiple locations on the microarray.

As used herein, the terms "complementary" or "partially complementary" to a target RNA (or target region thereof), and the percentage of "complementarity" of the probe sequence to that of the target RNA sequence is the percentage "identity" to the reverse complement of the sequence of the target RNA. In determining the degree of "complementarity" between probes used in the compositions described herein (or regions thereof) and a target RNA, such as those disclosed herein, the degree of "complementarity" is expressed as the percentage identity between the sequence of the probe (or region thereof) and the reverse complement of the sequence of the target RNA that best aligns therewith. The percentage is calculated by counting the number of aligned bases that are identical as between the 2 sequences, dividing by the total number of contiguous nucleotides in the probe, and multiplying by 100.

In some embodiments, the microarray comprises at least one probe having a region with a sequence that is fully complementary to a target region of a target RNA. In other embodiments, the microarray comprises at least one probe having a region with a sequence that comprises one or more base mismatches when compared to the sequence of the best-aligned target region of a target RNA.

In some embodiments, the microarray comprises at least one probe having a region of at least 10, at least 11, at least 13, at least 14, at least 15, at least 16, at least 17, at least 18 contiguous nucleotides identically present in, or complementary to, small U2, miR-720, miR-451, 13207, or 13750. In some embodiments, the microarray comprises at least one probe having a region of at least 10, at least 11, at least 13, at least 14, at least 15, at least 16, at least 17, at least 18, at least 19, at least 20, at least 21, at least 22, at least 23, at least 24, or at least 25 contiguous nucleotides with a sequence that is identically present in, or complementary to a region of, another target RNA.

In some embodiments, the microarrays comprise probes having a region with a sequence that is complementary to target RNAs that comprise a substantial portion of the human miRNome (i.e. the publicly known microRNAs that have been accessioned by others into miRBase (microrna.sanger.ac.uk/ at the time the microarray is fabricated), such as at least about 60%, at least about 70%, at least about 80%, at least about 90%, even at least about 95% of the human miRNome. In some embodiments, the microarrays comprise probes that have a region with a sequence that is identically present in target RNAs that comprise a substantial portion of the human miRNome, such as at least about 60%, at least about 70%, at least about 80%, at least about 90%, even at least about 95% of the human miRNome.

In some embodiments, components are provided that comprise probes attached to microbeads, such as those sold by Luminex, each of which is internally dyed with red and infrared fluorophores at different intensities to create a unique signal for each bead. In some embodiments, the compositions useful for carrying out the methods described herein include a plurality of microbeads, each with a unique spectral signature. Each uniquely labeled microbead is attached to a unique target RNA-specific probe such that the unique spectral signature from the dyes in the bead is associated with a particular probe sequence. Nonlimiting exemplary probe sequences include SEQ ID NOs: 42 to 61, 81, and 82. Nonlimiting exemplary probe sequences include sequences having at least 8, at least 9, at least 10, at least 11, at least 12, at least 13, at least 14, at least 15, at least 16, at least 17, at least 18 contiguous nucleotides of a sequence selected from SEQ ID NOs: 42 to 51, 81, and 82. Nonlimiting exemplary probe sequences include sequences having at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, or at least 70 contiguous nucleotides of a sequence selected from SEQ ID NOs: 52 to 61. Nonlimiting exemplary probe sequences also include probes comprising a region that is identically present in, or complementary to, small U2, miR-720, miR-451, 13207, or 13750. Nonlimiting exemplary probe sequences also include probes comprising a region that is identically present in, or complementary to, other target RNAs.

In some embodiments, a uniquely labeled microbead has attached thereto a probe having a region with a sequence that is identically present in, or complementary to a region of, small U2, miR-720, miR-451, 13207, or 13750. In some embodiments, a uniquely labeled microbead has attached thereto a probe comprising a sequence selected from SEQ ID NOs: 42 to 61, 81, and 82. In some embodiments, a uniquely labeled microbead has attached thereto a probe having a region with a sequence having at least 8, at least 9, at least 10, at least 11, at least 12, at least 13, at least 14, at least 15, at least 16, at least 17, at least 18 contiguous nucleotides of a sequence selected from SEQ ID NOs: 42 to 51, 81, and 82. In some embodiments, a uniquely labeled microbead has attached thereto a probe having a region with a sequence having at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, or at least 70 contiguous nucleotides of a sequence selected from SEQ ID NOs: 52 to 61. In some embodiments, a uniquely labeled microbead has attached thereto a probe having a region with a sequence that is identically present in, or complementary to a region of, another target RNA.

In some embodiments, a composition is provided that comprises a plurality of uniquely labeled microbeads, wherein at least one microbead has attached thereto a probe having a region with a sequence that is identically present in, or complementary to a region of, small U2, miR-720, miR-451, 13207, or 13750. In some embodiments, a composition is provided that comprises a plurality of uniquely labeled microbeads, wherein at least one microbead has attached thereto a probe comprising a sequence selected from SEQ ID NOs: 42 to 61, 81, and 82. In some embodiments, a composition is provided that comprises a plurality of uniquely labeled microbeads, wherein at least one microbead has attached thereto a probe having a region with a sequence having at least 8, at least 9, at least 10, at least 11, at least 12, at least 13, at least 14, at least 15, at least 16, at least 17, at least 18 contiguous nucleotides of a sequence selected from SEQ ID NOs: 42 to 51, 81, and 82. In some embodiments, a composition is provided that comprises a plurality of uniquely labeled microbeads, wherein at least one microbead has attached thereto a probe having a region with a sequence having at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, or at least 70 contiguous nucleotides of a sequence selected from SEQ ID NOs: 52 to 61. In some embodiments, a composition is provided that comprises a plurality of uniquely labeled microbeads, wherein at least one microbead has attached thereto a probe having a region with a sequence that is identically present in, or complementary to a region of, small U2, miR-720, miR-451, 13207, or 13750, and at least one microbead has attached thereto a probe having a region with a sequence that is identically present in, or complementary to a region of, another target RNA.

In some embodiments, the compositions comprise a plurality of uniquely labeled microbeads, each of which has attached thereto a unique probe having a region that is complementary to target RNAs that comprise a substantial portion of the human miRNome, such as at least about 60%, at least about 70%, at least about 80%, at least about 90%, or at least about 95% of the human miRNome. In some embodiments, the compositions comprise a plurality of uniquely labeled microbeads having attached thereto a unique probe having a region with a sequence that is identically present in target RNAs that comprise a substantial portion of the human miRNome, such as at least about 60%, at least about 70%, at least about 80%, at least about 90%, or at least about 95% of the human miRNome.

In some embodiments, compositions are provided that comprise at least one polynucleotide for detecting at least one target RNA. In some embodiments, the polynucleotide is used as a primer for a reverse transcriptase reaction. In some embodiments, the polynucleotide is used as a primer for amplification. In some embodiments, the polynucleotide is used as a primer for RT-PCR. In some embodiments, the polynucleotide is used as a probe for detecting at least one target RNA. In some embodiments, the polynucleotide is detectably labeled. In some embodiments, the polynucleotide is a FRET probe. In some embodiments, the polynucleotide is a TaqMan® probe, a Molecular Beacon, or a Scorpion probe.

In some embodiments, a composition comprises at least one FRET probe having a sequence that is identically present in, or complementary to a region of, small U2, miR-720, miR-451, 13207, or 13750. In some embodiments, a composition comprises at least one FRET probe having a sequence selected from SEQ ID NOs: 42 to 61, 81, and 82. In some embodiments, a composition comprises at least one FRET probe having a region with a sequence having at least 8, at least 9, at least 10, at least 11, at least 12, at least 13, at least 14, at least 15, at least 16, at least 17, at least 18 contiguous nucleotides of a sequence selected from SEQ ID NOs: 42 to 51, 81, and 82. In some embodiments, a composition comprises at least one FRET probe having a region with a sequence having at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, or at least 70 contiguous nucleotides of a sequence selected from SEQ ID NOs: 52 to 61. In some embodiments, a composition comprises at least one FRET probe having a region with a sequence that is identically present in, or complementary to a region of, small U2, miR-720, miR-451, 13207, or 13750, and at least one FRET probe having a region with a sequence that is identically present in, or complementary to a region of, another target RNA.

In some embodiments, a FRET probe is labeled with a donor/acceptor pair such that when the probe is digested during the PCR reaction, it produces a unique fluorescence emission that is associated with a specific target RNA. In some embodiments, when a composition comprises multiple FRET probes, each probe is labeled with a different donor/acceptor pair such that when the probe is digested during the PCR reaction, each one produces a unique fluorescence emission that is associated with a specific probe sequence and/or target RNA. In some embodiments, the sequence of the FRET probe is complementary to a target region of a target RNA. In other embodiments, the FRET probe has a sequence that comprises one or more base mismatches when compared to the sequence of the best-aligned target region of a target RNA.

In some embodiments, a composition comprises a FRET probe consisting of at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides, wherein at least a portion of the sequence is identically present in, or complementary to a region of, small U2, miR-720, miR-451, 13207, or 13750. In some embodiments, at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides of the FRET probe are identically present in, or complementary to a region of, small U2, miR-720, miR-451, 13207, or 13750. In some embodiments, the FRET probe has a sequence with one, two or three base mismatches when compared to the sequence or complement of small U2, miR-720, miR-451, 13207, or 13750.

In some embodiments, the compositions further comprise a FRET probe consisting of at least 10, at least 11, at least 13, at least 14, at least 15, at least 16, at least 17, at least 18, at least 19, at least 20, at least 21, at least 22, at least 23, at least 24, or at least 25 contiguous nucleotides, wherein the FRET probe comprises a sequence that is identically present in, or complementary to a region of, a region of another target RNA. In some embodiments, the FRET probe is identically present in, or complementary to a region of, at least at least 10, at least 11, at least 13, at least 14, at least 15, at least 16, at least 17, at least 18, at least 19, at least 20, at least 21, at least 22, at least 23, or at least 24 contiguous nucleotides of another target RNA.

In some embodiments, a kit comprises a polynucleotide discussed above. In some embodiments, a kit comprises at least one primer and/or probe discussed above. In some embodiments, a kit comprises at least one polymerase, such as a thermostable polymerase. In some embodiments, a kit comprises dNTPs. In some embodiments, kits for use in the real time RT-PCR methods described herein comprise one or more target RNA-specific FRET probes and/or one or more primers for reverse transcription of target RNAs and/or one or more primers for amplification of target RNAs or cDNAs reverse transcribed therefrom.

In some embodiments, one or more of the primers and/or probes is "linear". A "linear" primer refers to a polynucleotide that is a single stranded molecule, and typically does not comprise a short region of, for example, at least 3, 4 or 5 contiguous nucleotides, which are complementary to another region within the same polynucleotide such that the primer forms an internal duplex. In some embodiments, the primers for use in reverse transcription comprise a region of at least 4, such as at least 5, such as at least 6, such as at least 7 or more contiguous nucleotides at the 3'-end that has a sequence that is complementary to region of at least 4, such as at least 5, such as at least 6, such as at least 7 or more contiguous nucleotides at the 5'-end of a target RNA.

In some embodiments, a kit comprises one or more pairs of linear primers (a "forward primer" and a "reverse primer") for amplification of a cDNA reverse transcribed from a target RNA, such as small U2, miR-720, miR-451, 13207, or 13750. Accordingly, in some embodiments, a first primer comprises a region of at least 4, at least 5, at least 6, at least 7, at least 8, at least 9, or at least 10 contiguous nucleotides having a sequence that is identical to the sequence of a region of at least 4, at least 5, at least 6, at least 7, at least 8, at least 9, or at least 10 contiguous nucleotides at the 5'-end of a target RNA. Furthermore, in some embodiments, a second primer comprises a region of at least 4, at least 5, at least 6, at least 7, at least 8, at least 9, or at least 10 contiguous nucleotides having a sequence that is complementary to the sequence of a region of at least 4, at least 5, at least 6, at least 7, at least 8, at least 9, or at least 10 contiguous nucleotides at the 3'-end of a target RNA. In some embodiments, the kit comprises at least a first set of primers for amplification of a cDNA that is reverse transcribed from small U2, miR-720, miR-451, 13207, or 13750. In some embodiments, the kit further comprises at least a second set of primers for amplification of a cDNA that is reverse transcribed from another target RNA.

In some embodiments, the kit comprises at least two, at least five, at least 10, at least 15, at least 20, at least 25, at least 30, at least 40, at least 50, at least 60, at least 75, or at least 100 sets of primers, each of which is for amplification of a cDNA that is reverse transcribed from a different target RNA, including small U2, miR-720, miR-451, 13207, and 13750. In some embodiments, the kit comprises at least one set of primers that is capable of amplifying more than one cDNA reverse transcribed from a target RNA in a sample.

In some embodiments, probes and/or primers for use in the compositions described herein comprise deoxyribonucleotides. In some embodiments, probes and/or primers for use in the compositions described herein comprise deoxyribonucleotides and one or more nucleotide analogs, such as LNA analogs or other duplex-stabilizing nucleotide analogs described above. In some embodiments, probes and/or primers for use in the compositions described herein comprise all nucleotide analogs. In some embodiments, the probes and/or primers comprise one or more duplex-stabilizing nucleotide analogs, such as LNA analogs, in the region of complementarity.

In some embodiments, the compositions described herein also comprise probes, and in the case of RT-PCR, primers, that are specific to one or more housekeeping genes for use in normalizing the quantities of target RNAs. Such probes (and primers) include those that are specific for one or more products of housekeeping genes selected from U6 snRNA, ACTB, B2M, GAPDH, GUSB, HPRT1, PPIA, RPLP, RRN18S, TBP, TUBB, UBC, YWHA (TATAA), PGK1, and RPL4.

In some embodiments, the kits for use in real time RT-PCR methods described herein further comprise reagents for use in the reverse transcription and amplification reactions. In some embodiments, the kits comprise enzymes such as reverse transcriptase, and a heat stable DNA polymerase, such as Taq polymerase. In some embodiments, the kits further comprise deoxyribonucleotide triphosphates (dNTP) for use in reverse transcription and amplification. In further embodiments, the kits comprise buffers optimized for specific hybridization of the probes and primers.

4.2.1. Exemplary Normalization of RNA Levels

In some embodiments, quantitation of target RNA levels requires assumptions to be made about the total RNA per cell and the extent of sample loss during sample preparation. In order to correct for differences between different samples or between samples that are prepared under different conditions, the quantities of target RNAs in some embodiments are normalized to the levels of at least one endogenous housekeeping gene.

Appropriate genes for use as reference genes in the methods described herein include those as to which the quantity of the product does not vary between normal and cancerous lung cells, or between different cell lines or under different growth and sample preparation conditions. In some embodiments, endogenous housekeeping genes useful as normalization controls in the methods described herein include, but are not limited to, U6 snRNA, RNU44, RNU 48, and U47. In typical embodiments, the at least one endogenous housekeeping gene for use in normalizing the measured quantity of RNAs is selected from U6 snRNA, U6 snRNA, RNU44, RNU 48, and U47. In some embodiments, one housekeeping gene is used for normalization. In some embodiments, more than one housekeeping gene is used for normalization.

In some embodiments, a spike-in control polynucleotide is added to a patient sample, such as a serum sample, as a control. A nonlimiting exemplary spike-in control is CelmiR-39. In some embodiments, a spike-in control is used to correct for variations in RNA purification from the sample, such as serum. In some embodiments, the spike-in control is detected in the same, or a similar, assay as the target RNA(s). One skilled in the art can select a suitable spike-in control depending on the application.

4.2.2. Exemplary Qualitative Methods

In some embodiments, methods comprise detecting a qualitative change in a target RNA profile generated from a clinical sample as compared to a normal target RNA profile (in some exemplary embodiments, a target RNA profile of a control sample). Some qualitative changes in the RNA profile are indicative of the presence of lung cancer in the subject from which the clinical sample was taken. Various qualitative changes in the RNA profile are indicative of the propensity to proceed to lung cancer. The term "target RNA profile" refers to a set of data regarding the concurrent levels of a plurality of target RNAs in the same sample.

In some embodiments, at least one of the target RNAs of the plurality of target RNAs is at least one RNA selected from small U2, miR-720, miR-451, 13207, or 13750. In some embodiments, at least one, at least two, at least three, at least four, or at least five of the target RNAs of the plurality of target RNAs are selected from small U2, miR-720, miR-451, 13207, or 13750. In some embodiments, the plurality of target RNAs comprises at least one, at least two, at least five, at least 10, at least 15, at least 20, at least 25, at least 30, at least 40, at least 50, at least 60, at least 75, or at least 100 additional target RNAs. In some embodiments, a target RNA, in its mature form, comprises fewer than 30 nucleotides. In some embodiments, a target RNA is a microRNA. In some embodiments, a target RNA is a small cellular RNA.

Qualitative data for use in preparing target RNA profiles is obtained using any suitable analytical method, including the analytical methods presented herein.

In some embodiments, for example, concurrent RNA profile data are obtained using, e.g., a microarray, as described above. Thus, in addition to use for quantitatively determining the levels of specific target RNAs as described above, a microarray comprising probes having sequences that are complementary to a substantial portion of the miRNome may be employed to carry out target RNA profiling, for analysis of target RNA expression patterns.

According to the RNA profiling method, in some embodiments, total RNA from a sample from a subject suspected of having lung cancer is quantitatively reverse transcribed to provide a set of labeled polynucleotides complementary to the RNA in the sample. The polynucleotides are then hybridized to a microarray comprising target RNA-specific probes to provide a hybridization profile for the sample. The result is a hybridization profile for the sample representing the target RNA profile of the sample. The hybridization profile comprises the signal from the binding of the polynucleotides reverse transcribed from the sample to the target RNA-specific probes in the microarray. In some embodiments, the profile is recorded as the presence or absence of binding (signal vs. zero signal). In some embodiments, the profile recorded includes the intensity of the signal from each hybridization. The profile is compared to the hybridization profile generated from a normal, i.e., noncancerous, or in some embodiments, a control sample. An alteration in the signal is indicative of the presence of lung cancer in the subject.

4.3. Exemplary Additional Target RNAs

In some embodiments, in combination with detecting at least one RNA selected from small U2, miR-720, miR-451, 13207, and 13750, a method comprises detecting one or more additional target RNAs. Additional target RNAs include, but are not limited to, microRNAs, other small cellular RNAs, and mRNAs. In some embodiments, one or more additional target RNAs that have been shown to correlate with lung cancer in general, or a particular type or stage of lung cancer, are selected.

In some embodiments, the methods described herein further comprise detecting chromosomal codependents, i.e., target RNAs clustered near each other in the human genome which tend to be regulated together. Accordingly, in further embodiments, the methods comprise detecting the expression of one or more target RNAs, each situated within the chromosome no more than 50,000 bp from the chromosomal location of an RNA selected from small U2, miR-720, miR-451, 13207, and 13750.

4.4. Pharmaceutical Compositions and Methods of Treatment

In some embodiments, the disclosure relates to methods of treating lung cancer in which expression of a target RNA is deregulated, e.g., either down-regulated or up-regulated in the lung cancer cells of an individual. In some embodiments, the disclosure relates to methods of treating lung cancer in which levels of a target RNA are altered relative to normal cells or serum, e.g., either lower or higher in the lung cancer cells of an individual. When at least one isolated target RNA is up-regulated in the cancer cells, such as small U2, the method comprises administering to the individual an effective amount of at least one compound that inhibits the expression of the at least one target RNA, such that proliferation of lung cancer cells is inhibited. Alternatively, in some embodiments, when at least one target RNA is up-regulated in the cancer cells, the method comprises administering to the individual an effective amount of at least one compound that inhibits the activity of the at least one target RNA, such that proliferation of lung cancer cells is inhibited. Such a compound may be, in some embodiments, a polynucleotide, including a polynucleotide comprising modified nucleotides.

When at least one target RNA is down-regulated in the lung cancer cells, such as miR-451, miR-720, 13207, and/or 13750, the method comprises administering an effective amount of an isolated target RNA (i.e., in some embodiments, a target RNA that is chemically synthesized, recombinantly expressed or purified from its natural environment), or an isolated variant or biologically-active fragment thereof, such that proliferation of cancer cells in the individual is inhibited.

The disclosure further provides pharmaceutical compositions for treating lung cancer. In some embodiments, the pharmaceutical composition comprises a compound that inhibits the expression of, or the activity of, small U2. In some embodiments, the pharmaceutical compositions comprise at least one isolated target RNA, or an isolated variant or biologically-active fragment thereof, and a pharmaceutically-acceptable carrier. In some embodiments, the at least one isolated target RNA corresponds to a target RNA, such as miR-720, miR-451, 13207, and/or 13750, that is present at decreased levels in lung cancer cells relative to normal levels (in some exemplary embodiments, relative to the level of the target RNA in a control sample).

In some embodiments the isolated target RNA is identical to an endogenous wild-type target RNA gene product that is down-regulated in the cancer cell. In some embodiments, the isolated target RNA is a variant target RNA or biologically active fragment thereof. As used herein, a "variant" refers to a target RNA gene product that has less than 100% sequence identity to the corresponding wild-type target RNA, but still possesses one or more biological activities of the wild-type target RNA (e.g., ability to inhibit expression of a target RNA molecule and cellular processes associated with lung cancer). A "biologically active fragment" of a target RNA is a fragment of the target RNA gene product that possesses one or more biological activities of the wild-type target RNA. In some embodiments, the isolated target RNA can be administered with one or more additional anti-cancer treatments including, but not limited to, chemotherapy, radiation therapy and combinations thereof. In some embodiments, the isolated target RNA is administered concurrently with additional anti-cancer treatments. In some embodiments, the isolated target RNA is administered sequentially to additional anti-cancer treatments.

In some embodiments, the pharmaceutical compositions comprise at least one compound that inhibits the expression or activity of a target RNA. In some embodiments, the compound is specific for one or more target RNAs, the levels of which are increased in lung cancer cells relative to normal levels (in some exemplary embodiments, relative to the level of the target RNA in a control sample). In some embodiments, the target RNA inhibitor is specific for a particular target RNA, such as small U2. In some embodiments, the target RNA inhibitor comprises a nucleotide sequence that is complementary to at least a portion of small U2 and/or other target RNA.

In some embodiments, the target RNA inhibitor is selected from double-stranded RNA, antisense nucleic acids and enzymatic RNA molecules. In some embodiments, the target RNA inhibitor is a small molecule inhibitor. In some embodiments, the target RNA inhibitor can be administered in combination with other anti-cancer treatments, including but not limited to, chemotherapy, radiation therapy and combinations thereof. In some embodiments, the target RNA inhibitor is administered concurrently with other anti-cancer treatments. In some embodiments, the target RNA inhibitor is administered sequentially to other anti-cancer treatments.

In some embodiments, a pharmaceutical composition is formulated and administered according to Semple et al., Nature Biotechnology advance online publication, 17 Jan. 2010 (doi:10.1038/nbt.1602)), which is incorporated by reference herein in its entirety for any purpose.

The terms "treat," "treating" and "treatment" as used herein refer to ameliorating symptoms associated with lung cancer, including preventing or delaying the onset of symptoms and/or lessening the severity or frequency of symptoms of the lung cancer.

The term "effective amount" of a target RNA or an inhibitor of target RNA expression or activity is an amount sufficient to inhibit proliferation of cancer cells in an individual suffering from lung cancer. An effective amount of a compound for use in the pharmaceutical compositions disclosed herein is readily determined by a person skilled in the art, e.g., by taking into account factors such as the size and weight of the individual to be treated, the stage of the disease, the age, health and gender of the individual, the route of administration and whether administration is localized or systemic.

In addition to an isolated target RNA or a target RNA inhibitor, or a pharmaceutically acceptable salt thereof, the pharmaceutical compositions disclosed herein further comprise a pharmaceutically acceptable carrier, including but not limited to, water, buffered water, normal saline, 0.4% saline, 0.3% glycine, and hyaluronic acid.

In some embodiments, the pharmaceutical compositions comprise an isolated target RNA or a target RNA inhibitor that is encapsulated, e.g., in liposomes. In some embodiments, the pharmaceutical compositions comprise an isolated target RNA or a target RNA inhibitor that is resistant to nucleases, e.g., by modification of the nucleic acid backbone as described above in Section 4.1.5. In some embodiments, the pharmaceutical compositions further comprise pharmaceutically acceptable excipients such as stabilizers, antioxidants, osmolality adjusting agents and buffers. In some embodiments, the pharmaceutical compositions further comprise at least one chemotherapeutic agent, including but not limited to, alkylating agents, anti-metabolites, epipodophyllotoxins, anthracyclines, vinca alkaloids, plant alkaloids and terpenoids, monoclonal antibodies, taxanes, topoisomerase inhibitors, platinum compounds, protein kinase inhibitors, and antisense nucleic acids.

Pharmaceutical compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. Methods of administration include, but are not limited to, oral, parenteral, intravenous, oral, and by inhalation.

The following examples are for illustration purposes only, and are not meant to be limiting in any way.

5. EXAMPLES

5.1 Example 1

Small RNA Levels in Lung Primary Tumors Determined by Microarray

Selected Cohort

Thirteen patients diagnosed with lung cancer were included in the cohort, nine men and four women. Seven of the patients had never been smokers, and six had a history of heavy smoking. Because squamous cell lung cancer and non-squamous cell lung cancer are two of the most frequent lung cancer types (more than 70% of all lung cancers), three patients diagnosed with squamous cell carcinoma (Epi-4, Kmalp-21, Kmalp-25) and six patients diagnosed with non-squamous cell carcinoma (Adk-2, Adk-9, Adk-10, Adk-15, Adk-23 and Adk-29) were included. In addition, one patient diagnosed with a carcinoid (Car-13), one diagnosed with a carcinoma sarcomatoide (Ksarc-19), one diagnosed with a small cell lung cancer (Scc-27), and one diagnosed with a large cell neuroendocrine cancer (Lcnec-31) were also selected. Table 1 shows a list of the patients in the cohort and various clinical characteristics of each patient.

TABLE 1

| | | | | | | | |
|---|---|---|---|---|---|---|---|
| Clinical characteristics of patients in cohort | | | | | | | |
| Patient ID | histology | Tissue collected | gender | Birth year | Smoking history | TNM staging | Stage group |
| Adk-2 | adenocarcinoma | PT | Male | 1941 | 20 smokes/day | T2N0M0 | IB |
| Adk-9 | adenocarcinoma | PT | Male | 1953 | 40 smokes/day | T1N0M0 | IA |

TABLE 1-continued

Clinical characteristics of patients in cohort

| Patient ID | histology | Tissue collected | gender | Birth year | Smoking history | TNM staging | Stage group |
|---|---|---|---|---|---|---|---|
| Adk-10 | adenocarcinoma | PT | Male | 1959 | 25 smokes/day | T3N0M0 | IIB |
| Epi-4 | sqamous | PT | Male | 1930 | 30 smokes/day | T2NxM0 | IIIA |
| Adk-29 | adenocarcinoma | PT & ANT | Male | 1932 | ? smokes/day | T4N2M1 | IV |
| Adk-15 | adenocarcinoma | PT & ANT | Male | 1947 | ? smokes/day | T2N0M0 | IB |
| Adk-23 | adenocarcinome | PT & ANT | Female | 1971 | 0 | T3N0M0 | IIB |
| Ksarc-19 | carcinome sarcomatoide | PT & ANT | Male | 1949 | 0 | T4N1M0 | IIIB |
| Kmalp-25 | epidermoide | PT & ANT | Male | 1928 | 0 | T2N0M0 | IB |
| Kmalp-21 | epidermoide | PT & ANT | Female | 1942 | 0 | T3N1M0 | IIIA |
| Car-13 | carcinoide | PT & ANT | Female | 1952 | 0 | T3N1M0 | IIIA |
| Lcnec-31 | neuroendocrine GC | PT & ANT | Male | 1946 | 0 | T3N2M0 | IIIA |
| Scc-27 | petites cellules | PT & ANT | Female | 1943 | 0 | T2N0M0 | IB |

PT = Primary Tumor
ANT = Adjacent Normal Tissue

Four of the patients had very aggressive forms of lung cancer, Ksarc-19 (carcinoma sarcomatoide), Adk-10 and Adk-29 (both non-squamous cell carcinoma), and Lcnec-31. Patient Ksarc-19 relapsed one month after surgery and died six months later. Patient Car-13 (carcinoide) had a slow growing form of lung cancer.

The primary tumors only were collected from four of the patients, while the primary tumor and adjacent normal tissue were collected from the remaining nine. The relative amount of tumor cells versus normal cells in primary tumors was determined to be between 90% and 100% for all patients. The adjacent normal tissue was collected from a location as far as possible from the primary tumor, and did not contain detectable tumor cells.

Tissue Samples

Archived or freshly snap-frozen specimens from lung primary tumors were used. Tissue samples were homogenized by mortar and pestle in TRIzol® Reagent (Invitrogen; Carlsbad, Calif.) and RNA was extracted according to manufacturer's protocol. RNA samples were diluted in RNase-free water and stored in −80° C. (−112° F.).

Small RNA Preparation

All samples were enriched for the small RNA fraction using a Flash PAGE Fractionator (Ambion). Briefly, a total RNA sample was loaded onto a pre-cast gel using the Flash PAGE Fractionator. The total RNA fraction smaller than 40 nt (the "small RNA fraction") was recovered after gel migration and resuspended into nuclease free water.

Microarray Analysis

Probe Design and Spotting

The polynucleotide probes used for microarray preparation had the configuration 5'—NH$_2$—(C)$_6$-(spacer)-(oligomer probe sequence)-3'. The 5'-amino group allowed chemical bonding onto the array support. Each also included an identical spacer sequence of 15 nt, as shown below, to prevent non-specific interactions of the polynucleotide probes with the array support:

(SEQ ID NO: 62)
5'AminoC6-TTGTAATACGACTCA - Oligo probe sequence.

The probe sequences herein omit the linker. Because the microarray was originally designed to detect microRNA levels, the probe that appears to have hybridized with small U2 RNAs was the probe for miR-1290, which had the sequence:

(SEQ ID NO: 63)
5'-TCCCTGATCCAAAAATCCA-3'

That sequence differs from a complement of a small U2 sequence by just one nucleotide, which is shown in bold.

The probes were synthesized according to standard protocols by Eurofins MWG Operon (Ebersberg, Germany). Nexterion (Schott) microarray glass slides were used as the solid support for the microarray.

The polynucleotide probe concentration used for the spotting was 25 µmol. The probes were spotted in duplicate using the Nexterion spotting buffer provided with the array glass support by Schott with 1% SDS (sodium dodecyl sulfate) added to allow larger spot sizes (e.g., 100-150 microns compared to 70-100 microns without SDS). The spotter used was the QArray mini (Genetix) equipped with Stealth SMP3 pins (Telechem). After deposition of one series of spots, the spotting needle was washed 5 times with 60 mM NaOH before spotting the next series of probes. Each slide is designed with 48 blocks of spotted probes, with each block being a 20×18 square of spotted probes. Each probe was spotted in duplicate. Spotted glass slides were stored at 4° C. until use.

Small RNA Labelling

The labelling of the small RNA fraction was adapted from a published protocol developed at EMBL (Heidelberg, Germany) by the European Molecular Biology Group (Castoldi et al., RNA 2006 May; 12(5):913-20, incorporated herein by reference in its entirety). Briefly, the small RNA fraction was incubated for 6 hours at 4° C. with a mixture containing 10 µM of dye-labelled tetra-nucleotide (5'-rUrUrUrU-Cy5-3') (or alternatively, 5'-rUrUrUrU-Cy3-3') (Biospring, Germany) in Ambion buffer diluted to 1× with RNase free water, 8% polyethylene glycol (PEG), 2 mM adenosine triphosphate (ATP), and T4 RNA ligase (0.7 U/µl). The labelling reaction was run by heating the mixture for 15 minutes at 65° C. This procedure ligated the poly-U dye-labelled tail to the 3' end of all the small RNAs. Labelled samples were stored at 4° C. before hybridization.

Array Hybridization

The labelled small RNA fraction was hybridized to the spotted arrays using a Discovery hybridization station (Ventana, Tucson, Ariz.). Briefly, 2 mL of a mixture of 1% BSA, 2×SSC, and 0.2% SDS was incubated with the chips for 30 min at 42° C. Then the chips were washed once using EZ Prep buffer (Ventana) and then three more times with Ribowash (Ventana). Next, 20 µl of the labelled small RNA mixture and 180 µl of ChipHybe Reagent (Ventana) were added to the array. The arrays were heated for 6 minutes at 37° C., then were incubated at 42° C. for 8 hours, after which the heating was stopped. The chips were washed once with Ribowash (Ventana) and then heated for 2 minutes at 37° C. The chips were washed again with Ribowash (Ventana) with one drop of CheapClean (Ventana) added, and incubated for 2 minutes at 37° C. The chips were washed two more times using Ribowash (Ventana). Chips were stored dry overnight. On the following day, the final washes were done according to Ventana's instructions for the Discovery hybridization station. The slides were washed twice with 2×SSC+0.2×SDS buffer and then one more time with 0.1×SSC. All the slides were dried using a speed centrifuge from Arrayit (TeleChem International, Sunnyvale, Calif.) at room temperature and kept in the dark before scanning.

Array Image Acquisition

The arrays were scanned using an Axon™ scanner (Molecular Devices, Sunnyvale, Calif.) and their Genepix™ software. The image was formatted in tif format, defined by an image color depth of 16 bits/pixel (1600*1600). At such setting, pixels can assume intensity values ranging from 0 to 65,535. Pixels exhibiting the maximum intensity value are "saturated" and were assigned the value of 65,535. The resolution of the array scan was set at 10 μm/pixel. For hybridization experiments using different fluorescent dyes (e.g., Cy5 and Cy3) the photomultiplier tube (PMT) was adjusted to the higher intensity spot (Cy3 is scanned at lower PMT settings than Cy5).

Array Image Analysis

The PMT of the laser scanner digitized the captured fluorescence intensity for each given "point" of a slide and stored the numerical value as a pixel corresponding to that point. A picture composed of such pixels was then analyzed. The first task for image analysis was to detect the spot position, using a process called segmentation. Spots were segmented by circles of adaptable or fixed radius. To be reliably segmented and quantified, the spot diameter was required to be more than 5-6 pixels. Before segmentation an indexing grid was provided giving the approximate positions of the spots. The segmentation itself detected the limits of spots near the grid circles. Briefly, the Genepix software assigns a circle to each spot on the array (segmentation). The segmentation had to be conducted in a somewhat flexible way due to spotting imperfections and/or support deformation, as the spots were almost never on a perfectly rectangular grid.

After segmentation by the software, the circles were modified manually and adjusted onto the spots until all the spots on the array were clearly identified. At this stage, if the array presented high background noise preventing real spots from being distinguished from the background, the array was rejected for further analysis.

The second task of image analysis was to quantify spots and export the data into a result file. This was a relatively easy and well-defined task once the spots were located on the image. The statistical approach used most frequently to quantify spot intensity was the mean or median of pixels belonging to a spot. The median approach was more robust than the mean value in the presence of outlier pixels. In practice, however, there was little difference in the results obtained using mean or median.

Array Data Analysis

All the array data were analysed using the R bioconductor package ("Bioconductor: open software development for computational biology and bioinformatics," *Genome Biol.* 2004; 5(10):R80. Epub 2004 Sep. 15, which is incorporated herein by reference in its entirety).

Array data were first tested for quality by comparing the spot intensities for the internal controls. One internal control (SEQ ID NO: 64; Table 2) was used as a labelling control (this synthetic RNA is added to the purified small RNA fraction before labelling), and 6 other internal controls (SEQ ID NOS: 65 to 70; Table 2) were used for the normalization of the data (these synthetic RNA controls are added to the total RNA fraction before hybridization at 520 fmol each/array). The probe sequences that bind to the synthetic RNAs, and a mutant probe sequence, are also shown in Table 2 (SEQ ID NOS: 71 to 78).

TABLE 2

Control Sequences used in microarray experiments

| Sequence (5'-3') | Sequence identification number |
|---|---|
| CGCGCGUCGCUUUAUCUACUGU | SEQ ID NO: 64; CTL30_COMP |
| UUAUCGUUCGAUAAGUCGCGUU | SEQ ID NO: 65; CTL11_COMP |
| GAAGUUACUAUGUAGGCAACCU | SEQ ID NO: 66; CTL23_COMP |
| CGCGGGACUAAUUGUUACCGGG | SEQ ID NO: 67; CTL26_COMP |
| UCGCGUCGAACUCCGCAACCGA | SEQ ID NO: 68; CTL29_COMP |
| ACCGAACGCCGUACCCAUCGGG | SEQ ID NO: 69; CTL31_COMP |
| CGAGGGUAACGACUCUCGUGUC | SEQ ID NO: 70; CTL36_COMP |
| TTGTAATACGACTCAACAGTAGATAAAGCGACGCGCG | SEQ ID NO: 71; CTL30 |
| TTGTAATACGACTCAAACGCGACTTATCGAACGATAA | SEQ ID NO: 72; CTL11 |
| TTGTAATACGACTCAAGGTTGCCTACATAGTAACTTC | SEQ ID NO: 73; CTL23 |
| TTGTAATACGACTCACCCGGTAACAATTAGTCCCGCG | SEQ ID NO: 74; CTL26 |
| TTGTAATACGACTCATCGGTTGCGGAGTTCGACGCGA | SEQ ID NO: 75; CTL29 |
| TTGTAATACGACTCACCCGATGGGTACGGCGTTCGGT | SEQ ID NO: 76; CTL31 |
| TTGTAATACGACTCAGACACGAGAGTCGTTACCCTCG | SEQ ID NO: 77; CTL36 |
| TTGTAATACGACTCACCCGGTAACAATTAGACCCGCG | SEQ ID NO: 78; CTL26_MUT |

All sequences for which the intensity of the spot was higher than the mean local background intensity plus 1.5 times its standard deviation were categorized as expressed small RNAs. The following criteria were required to be met in order consider the array intensity data valid for further analysis:
1. Specificity of the hybridization controls had to be within acceptance criteria (e.g. CTL26 vs. its corresponding single base mutant, CTL26_MUT).
2. Approximate equality of the signal intensity of the replicates of the positive controls
3. Approximate equality between median block signal intensities based on the positive controls for each block
4. Approximate equality between median array signals based on all sequences detected
5. Signal intensity for the purification and labelling control (CTL30).

Statistical normalization of the data was done by computing the Log 2ratio where the Log 2ratio equals average intensity signal of the duplicated spots/median intensity of all positives controls for the block. The normalization was done per block to avoid non-homogenous labelling of all blocks of the array. This block-by-block normalization has been shown to be more efficient then when using overall normalization of the slide. The obtained values are Log 2 values.

The intensities of the spots for each polynucleotide probe were compared in the sample from the lung cancer primary tumors versus normal lung tissue, resulting in an evaluation of the relative levels for each small RNA, such as microRNAs.

The fold-change in RNA levels corresponds to $2^{(Log\ 2ratio)}$. The Log 2ratio is the ratio between the two conditions compared, or log 2(Xprimary-tumor/Xnormal), which is the same as (log 2Xprimary-tumor−log 2Xnormal), where X is the measured intensity value. In cases where there was no signal from the "normal" condition, the lowest measured intensity value in the experiment was used as the baseline from which a fold-change value was calculated. A fold-change value of less than zero corresponds to a down-regulation of (1/fold-change) times.

Results

Increased levels of small U2 were observed for most of the primary tumors analyzed. While this RNA was initially identified as miR-1290, which differs in sequence by one nucleotide, it became clear upon sequencing serum samples, discussed below, that small U2 was being detected in this assay, and other assays, and that small U2 is present at higher levels in serum from lung cancer patients than in serum from healthy individuals.

Table 3 shows the normalized signal values for small U2 for each of the tissues. Table 3 also shows the fold-change in small U2 levels, calculated in two different ways. First, the level of small U2 in primary tumor samples compared to the level of small U2 in adjacent normal tissue from the same patient was calculated for the nine patients from which adjacent normal tissue was collected ("fold changes/same individual"). By that measure, levels of small U2 are significantly higher in seven of the nine patients. The fold-change ranged from 3.11 (Adk-15) to 33.74 (Kmal-21). The level of small U2 appeared to be similar in primary tumor samples and adjacent normal tissue in patient Adk-29, while the level of small U2 was lower in the primary tumor sample, as compared to the adjacent normal tissue, of patient Car-13, who had a very slow growing form of lung cancer.

In the second fold-change calculation, the fold-change of small U2 levels were calculated based on the levels in primary tumors from each patient and the average (6.08) of small U2 levels in the nine adjacent normal tissues.

TABLE 3

Fold-changes observed in small U2 levels in primary tumor samples

| Patient ID | Primary tumor | Adjacent normal tissue (NT) | Fold change/ same individual | Fold change/ ratio of all NT |
|---|---|---|---|---|
| Ksarc-19 | −0.84 | −5.77 | 30.49 | 37.86 |
| LCNEC-31 | −2.99 | −7.10 | 17.22 | 8.50 |
| scc-27 | −2.89 | −5.17 | 4.84 | 9.11 |
| EPI-4 | −0.62 | na | na | 43.83 |
| Kmalp21 | 0.19 | −4.89 | 33.74 | 77.03 |
| Kmalp25 | −1.72 | −4.98 | 9.57 | 20.45 |
| Car13 | −9.00 | −7.40 | −3.04 | −7.58 |
| adk15 | −4.83 | −6.47 | 3.11 | 2.37 |
| adk23 | −4.96 | −8.00 | 8.23 | 2.17 |
| ADK9 | −5.09 | na | na | 1.99 |
| ADK10 | −5.72 | na | na | 1.28 |
| adk29 | −4.76 | −5.06 | 1.23 | 2.49 |
| ADK2 | −9.00 | na | na | −7.59 |

Small U2 levels were found to be increased in most primary tumor samples using both methods of calculating the fold-change.

Increased levels of miR-720 and 13207, and decreased levels of miR-451 were also observed for most of the primary tumors analyzed in this small cohort. Table 4 shows the fold-change in miR-720, miR-451, and 13207 levels, calculated using the ratio of the level of each microRNAs in the primary tumor and the average of the microRNA levels in the normal tissue samples, as described above. Levels of miR-720, miR-451, and 13207 were not determined for patient ADK2.

TABLE 4

Fold-changes observed in miR-720, miR-451, and 13207 levels in primary tumor samples

| Patient ID | miR-720 | miR-451 | 13207 |
|---|---|---|---|
| Ksarc-19 | 2.72 | −10.15 | 60.35 |
| LCNEC-31 | Nd | −2.86 | 10.31 |
| scc-27 | 1.35 | −7.90 | 11.85 |
| EPI-4 | Nd | −9.47 | 43.85 |
| Kmalp21 | 1.99 | −7.99 | 18.94 |
| Kmalp25 | 1.95 | −3.72 | 22.74 |
| Car13 | Nd | −3.23 | nd |
| Adk15 | 2.73 | −4.68 | 2.98 |
| Adk23 | 5.03 | −16.47 | 2.45 |
| ADK9 | 9.81 | −5.28 | 2.02 |
| ADK10 | 4.77 | −7.77 | 1.32 |
| adk29 | 3.06 | −12.78 | 1.52 |

5.2 Example 2

Small RNA Levels in Lung Primary Tumors Determined by qRT-PCR

A TaqMan® quantitative RT-PCR (qRT-PCR; Applied Biosystems) assay was used to measure small U2 in the same small RNA samples used for the microarray experiment in Example 1. The small RNA RNU44 was used as an endogenous control (Amaral F C et al. J Clin Endocrinol Metab 94: 320-323 (2009)). Small RNA from primary tumors of six patients (Adk-15, Adk-23, Kmalp-25, Adk-29, Scc-27 and Lcnec-31) and from the adjacent normal tissue from three of those patients (Adk-15, Adk-23 and Scc-27) were used in the analysis.

The fold changes in the levels of small U2 in primary tumors were calculated using the $2^{-\Delta\Delta Ct}$ method (Livak and Schmittgen, Methods, 25: 402-408 (2001)), and using the average of small U2 levels in the 3 adjacent normal tissues as a reference. The results are shown in Table 5.

TABLE 5 qRT-PCR quantification of small U2 in tissue samples

| ID | SAMPLE DESCRIP. | U2 Ct | RNU44 Ct | ΔCt = U2 Ct − RNU44 Ct | ΔΔCt = U2 ΔCt − RNU44 ΔCt | $2^{-\Delta\Delta Ct}$ |
|---|---|---|---|---|---|---|
| Adk-15 | Normal tissue | 35.53 | 28.71 | 6.82 | | |
| Adk-23 | Normal tissue | 35.99 | 29.77 | 6.22 | | |
| Scc-27 | Normal tissue | 33.48 | 27.23 | 6.25 | | |
| Adk-15 | Primary tumor | 30.42 | 25.57 | 4.85 | −1.58 | 2.99 |
| Adk-23 | Primary tumor | 30.28 | 27.24 | 3.04 | −3.39 | 10.48 |
| Kmalp-25 | Primary tumor | 27.89 | 25.68 | 2.21 | −4.22 | 18.64 |
| Adk-29 | Primary tumor | 31.91 | 25.83 | 6.08 | −0.35 | 1.27 |
| Scc-27 | Primary tumor | 28.47 | 26.52 | 1.95 | −4.48 | 22.32 |
| Lcnec-31 | Primary tumor | 28.52 | 25.8 | 2.72 | −3.71 | 13.09 |

The qRT-PCR data correlated well with the results of the microarray experiment discussed above. FIG. 1 shows the results for the six samples assayed in the qRT-PCR experiment. In that figure, qRT-PCR is the $2^{-\Delta\Delta Ct}$ data shown in Table 5. "microarray—1—" is the fold-changes calculated by comparing the levels of small U2 in primary tumor samples to the levels in adjacent normal tissue of the same patient. "Microarray—ratio—" is the fold-changes calculated by comparing the levels of small U2 in primary tumor samples and the average of adjacent normal tissue of all patients. Overall, the qRT-PCR results are consistent with the microarray data for small U2.

The results of the microarray and qRT-PCR experiments demonstrate that small U2 levels are higher in most primary lung tumors assayed (10 out of 13) and that the increased levels of small U2 are not lung tumor subtype-specific.

A similar TaqMan® quantitative RT-PCR (qRT-PCR) assay was used to measure levels of miR-720, miR-451, and 13207 in the same small RNA samples used for the microarray experiment in Example 1. In this case, however, the small RNA RNU48 was used as an endogenous control (Zhu et al. *BMC Res. Notes* 2:89 (2009); Collino et al. *PLoS ONE* 5:1 (2010); Chiyomaru et al. *J. Canc.* 102:883 (2010)). Small RNA from primary tumors of six patients (Adk-15, Adk-23, Kmalp-25, Adk-29, Scc-27 and Lcnec-31) and from the adjacent normal tissue from three of those patients (Adk-15, Adk-23 and Scc-27) were used in the analysis.

The fold changes in the levels of miR-720, miR-451, and 13207 in primary tumors were calculated using the $2^{-\Delta\Delta Ct}$ method (Livak and Schmittgen, Methods, 25: 402-408 (2001)), and using the average of the microRNA levels in the 3 adjacent normal tissues as a reference. For down-regulated RNAs, the fold changes were calculated as $-\frac{1}{2}^{-\Delta\Delta Ct}$. The results are shown in Table 6.

TABLE 6 qRT-PCR quantification of miR-720, miR-451, and 13207 in tissue samples

| ID | Sample Description | $-\frac{1}{2}^{-\Delta\Delta Ct}=$ ΔmiR-13207 Ct − ΔRNU48 Ct | $2^{-\Delta\Delta Ct}=$ ΔmiR-720 Ct − ΔRNU48 Ct | $-\frac{1}{2}^{-\Delta\Delta Ct}=$ ΔmiR-451 Ct − ΔRNU48 Ct |
|---|---|---|---|---|
| adk-15 | Primary tumor | −2.20 | 5.35 | −3.43 |
| adk-23 | Primary tumor | −1.83 | 10.56 | −17.27 |
| Kmalp-25 | Primary tumor | −10.13 | 3.43 | na |
| adk-29 | Primary tumor | −11.79 | −1.12** | −81.57 |
| scc-27 | Primary tumor | 1.01* | 2.66 | −4.41 |
| Lcnec-31 | Primary tumor | −4.47 | −2.22** | −4.96 |

*This number is $2^{-\Delta\Delta Ct}$.
**These numbers are $-\frac{1}{2}^{-\Delta\Delta Ct}$.

Those results show that miR-451 and 13207 levels are generally lower in primary tumor tissue than in normal tissue.

5.3 Example 3

Small RNA Levels Determined by qRT-PCR in Larger Cohort

Selected Cohort

Thirty-six individuals were selected, 24 of which had been diagnosed with lung cancer, and 12 of which were healthy. This study demonstrates that small U2 can be used as an early detection marker for lung cancer using a minimally invasive assay.

The 24 lung cancer patients had early-stage lung cancer: six were diagnosed with stage IA lung cancer, 14 with stage IB, and four with stage IIB. The cohort included 16 men and eight women. Sixteen of the patients were smokers, one was a former smoker, and seven had never been smokers. None of the patients had been diagnosed with diabetes, infectious disease, other cancers, obesity, or cardiac problems. None of the patients were taking medication at the time the tissue was collected. Table 7 shows 24 patients with lung cancer in the cohort and various clinical characteristics of each patient.

TABLE 7

Clinical characteristics of lung cancer patients in cohort

| ID | Age at Excision | Gender | Smoking Status | Clinical Diagnosis | Stage | Stage Group |
|---|---|---|---|---|---|---|
| 47031 | 51 | Female | Never Used | Papillary adenocarcinoma | T1NXM0 | IA |
| 48716 | 54 | Female | 30 smokes/Day | Squamous cell carcinoma | T2N1M0 | IIB |
| 41379 | 48 | Female | Never Used | Adenocarcinoma | T1NXM0 | IA |
| 48708 | 55 | Male | 25 smokes/Day | Squamous cell carcinoma | T1N0M0 | IA |
| 48712 | 50 | Male | Never Used | Squamous cell carcinoma | T2N0M0 | IB |
| 49129 | 69 | Male | 20 smokes/Day | Adenocarcinoma | T2N0M0 | IB |
| 47044 | 65 | Male | 20 smokes/Day | Squamous cell carcinoma | T2NXM0 | IB |
| 47042 | 60 | Male | 20 smoke(s) | Squamous cell carcinoma | T2NXM0 | IB |
| 48714 | 57 | Female | Never Used | Adenocarcinoma | T2N0M0 | IB |
| 45417 | 34 | Female | 40 smokes/Day | Adenocarcinoma | T2N0MX | IB |
| 47322 | 57 | Male | 15 smokes/Day | Squamous cell carcinoma | T2NXM0 | IB |
| 47033 | 54 | Male | 30 smokes/Day | Adenocarcinoma | T1NXM0 | IA |
| 45937 | 59 | Male | 15 smokes/Day | Adenocarcinoma | T2N1MX | IIB |
| 45926 | 50 | Male | 20 smokes/Day | Adenocarcinoma | T2N0M0 | IB |
| 49137 | 70 | Female | Never Used | Adenocarcinoma | T1N0M0 | IA |
| 45694 | 57 | Female | Never Used | Bronchiolo-alveolar carcinoma | T1NXM0 | IA |
| 45424 | 50 | Male | 40 smokes/Day | Squamous cell carcinoma | T2N1MX | IIB |
| 45419 | 52 | Male | 20 smokes/Day | Adenocarcinoma | T2N0MX | IB |
| 41537 | 56 | Male | 20 smokes/Day | Adenocarcinoma | T2N1MX | IIB |
| 44664 | 63 | Male | 60 cig(s)/Day | Squamous cell carcinoma | T2N0M0 | IB |
| 45407 | 55 | Male | 30 smokes/Day | Squamous cell carcinoma | T2N0MX | IB |
| 49136 | 63 | Male | Previous Use | Squamous cell carcinoma | T2NXM0 | IB |
| 48710 | 53 | Male | 30 smokes/Day | Adenocarcinoma | T2N0M0 | IB |
| 48711 | 61 | Female | Never Used | Squamous cell carcinoma | T2N0M0 | IB |

The 12 healthy individuals in the cohort did not have any of diabetes, infectious disease, cancer, obesity, or cardiac problems. None of the healthy individuals were taking medication at the time tissue was collected. Table 8 shows 12 healthy individuals in the cohort and various clinical characteristics of each individual.

TABLE 8

Clinical characteristics of healthy individuals in cohort

| ID | Age at Sampling | Gender | Smoking Status |
|---|---|---|---|
| 50437 | 47 | Male | Previous use |
| 42199 | 21 | Male | 3 smokes/day |
| 49508 | 37 | Male | Never Used |
| 50444 | 40 | Female | 10 smokes/day |
| 49511 | 40 | Male | Never Used |
| 42214 | 22 | Female | Previous use |
| 50448 | 38 | Female | Previous use |
| 46816 | 39 | Female | Never Used |
| 49509 | 35 | Female | Never Used |
| 43517 | 37 | Male | 20 smokes/day |
| 46810 | 38 | Female | Never Used |
| 50446 | 35 | Male | 4 smokes/day |

For each individual in the cohort, 1 ml of serum was used to extract RNA for use in a TaqMan® quantitative RT-PCR assay for small U2 levels.

Isolation of Total RNA from Serum Samples

Three volumes (3 ml) of Trizol LS was added to each serum sample, and the samples were then incubated for five minutes at room temperature. 0.8 ml chloroform (0.2 ml chloroform per 0.75 ml Trizol LS) was added to each sample, and the samples were then vortexed vigorously for 15 seconds. The samples were incubated for 3 minutes at room temperature. The samples were then centrifuged for 15 minutes at 12,000×g (9,600 rpm) at 4° C., and the aqueous phase (4 ml) was collected.

One volume of acidified phenol/chloroform (5 parts phenol to 1 part chloroform, pH 4.5) was added to the aqueous phase. The phases were gently vortexing and allowed to sit at room temperature for 2 to 3 minutes. The samples were then centrifuged for 10 minutes at 12,000×g (9,600 rpm) at 4° C., and the aqueous phase was collected. The phenol/chloroform extraction was then repeated.

Following the second phenol/chloroform extraction, 1.25 volumes of 100% EtOH was added to each sample and the samples were vortexed. 700 µl of each sample was loaded onto a mirVana™ miRNA isolation column (Ambion) and the column was centrifuged for 15 seconds at 8,000×g at room temperature. The filtrate was discarded, and another 700 µl of sample was loaded onto the columns and centrifuged. The filtrate was again discarded. The process was repeated until all of the sample had been run through the mirVana™ column.

700 µl of miRNA wash solution 1 was then loaded on the mirVana™ columns. The columns were centrifuged for 10 seconds at 8,000×g at room temperature, and the filtrate discarded. 500 µl of miRNA wash solution 2/3 was then loaded on the mirVana™ columns. The columns were centrifuged for 10 seconds at 8,000×g at room temperature, and the filtrate discarded. 500 µl of miRNA wash solution 2/3 was again loaded on the mirVana™ columns. The columns were centrifuged for 10 seconds at 8,000×g at room temperature, and the filtrate discarded.

The columns were centrifuged for 1 minute at 8,000×g at room temperature to remove residual wash buffer. The columns were transferred to clean tubes and 100 µl of RNase-free water was added to the columns and they were centrifuged for 20 seconds at maximum speed (12,000×g; 9,600 rpm) at room temperature.

Detection of Small U2 in Serum by qRT-PCR

TaqMan® quantitative RT-PCR (qRT-PCR; Applied Biosystems) assays were used to measure small U2 levels in the total RNA samples isolated from the serum of the individuals in the cohort. The average Ct from three reactions is shown in Table 9 for each individual in the cohort, along with certain characteristics from Tables 7 and 8.

TABLE 9

Average Ct values for qRT-PCR of small U2

| ID | Smoking Status | Clinical Diagnosis | Stage | Stage Group | Average Ct |
|---|---|---|---|---|---|
| 47031 | Never Used | Papillary adenocarcinoma | T1NXM0 | IA | 35.17 |
| 48716 | 30 smokes/Day | Squamous cell carcinoma | T2N1M0 | IIB | 34.71 |
| 41379 | Never Used | Adenocarcinoma | T1NXM0 | IA | 32.28 |
| 48708 | 25 smokes/Day | Squamous cell carcinoma | T1N0M0 | IA | 32.22 |
| 48712 | Never Used | Squamous cell carcinoma | T2N0M0 | IB | 32.15 |
| 49129 | 20 smokes/Day | Adenocarcinoma | T2N0M0 | IB | 32.06 |
| 47044 | 20 smokes/Day | Squamous cell carcinoma | T2NXM0 | IB | 31.91 |
| 47042 | 20 smoke(s) | Squamous cell carcinoma | T2NXM0 | IB | 31.86 |
| 48714 | Never Used | Adenocarcinoma | T2N0M0 | IB | 31.84 |
| 45417 | 40 smokes/Day | Adenocarcinoma | T2N0MX | IB | 31.77 |
| 47322 | 15 smokes/Day | Squamous cell carcinoma | T2NXM0 | IB | 31.77 |
| 47033 | 30 smokes/Day | Adenocarcinoma | T1NXM0 | IA | 31.76 |
| 45937 | 15 smokes/Day | Adenocarcinoma | T2N1MX | IIB | 31.62 |
| 45926 | 20 smokes/Day | Adenocarcinoma | T2N0M0 | IB | 31.35 |
| 49137 | Never Used | Adenocarcinoma | T1N0M0 | IA | 31.31 |
| 45694 | Never Used | Bronchiolo-alveolar carcinoma | T1NXM0 | IA | 30.85 |
| 45424 | 40 smokes/Day | Squamous cell carcinoma | T2N1MX | IIB | 30.56 |
| 45419 | 20 smokes/Day | Adenocarcinoma | T2N0MX | IB | 30.54 |
| 41537 | 20 smokes/Day | Adenocarcinoma | T2N1MX | IIB | 30.25 |
| 44664 | 60 cig(s)/Day | Squamous cell carcinoma | T2N0M0 | IB | 30.18 |
| 45407 | 30 smokes/Day | Squamous cell carcinoma | T2N0MX | IB | 30.17 |
| 49136 | Previous Use | Squamous cell carcinoma | T2NXM0 | IB | 29.63 |
| 48710 | 30 smokes/Day | Adenocarcinoma | T2N0M0 | IB | 28.88 |
| 48711 | Never Used | Squamous cell carcinoma | T2N0M0 | IB | 28.78 |
| 50437 | Previous use | Healthy | | | 38.69 |
| 42199 | 3 smokes/day | Healthy | | | 35.48 |
| 49508 | Never Used | Healthy | | | 35.09 |
| 50444 | 10 smokes/day | Healthy | | | 34.91 |
| 49511 | Never Used | Healthy | | | 34.2 |
| 42214 | Previous use | Healthy | | | 34.17 |
| 50448 | Previous use | Healthy | | | 34.02 |
| 46816 | Never Used | Healthy | | | 34 |
| 49509 | Never Used | Healthy | | | 33.98 |
| 43517 | 20 smokes/day | Healthy | | | 33.66 |
| 46810 | Never Used | Healthy | | | 33.07 |
| 50446 | 4 smokes/day | Healthy | | | 32.34 |

Figure 2:
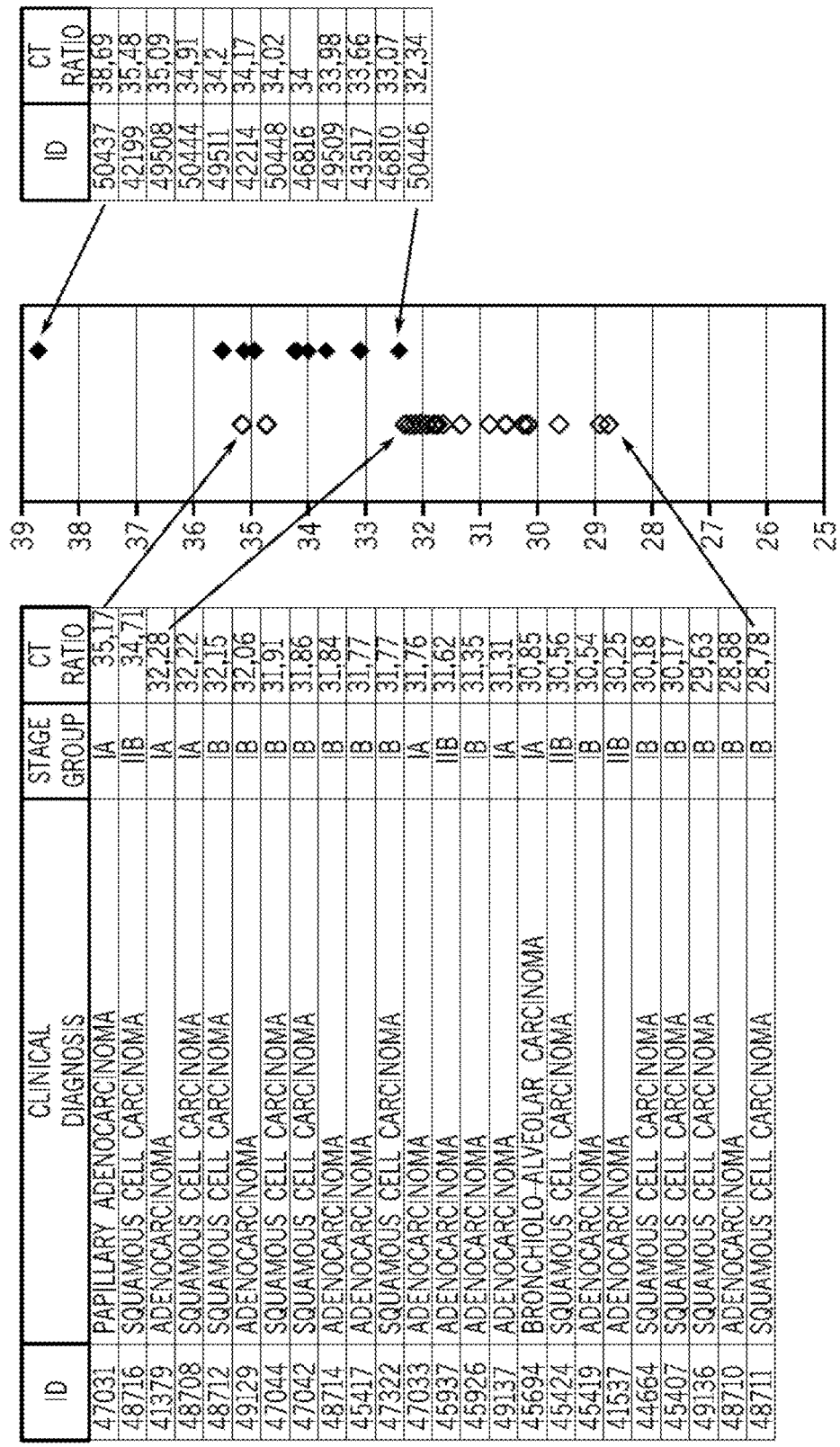
FIG. 2 shows a plot of the qRT-PCR Ct values for small U2 in serum samples from lung cancer patients and healthy individuals, as described in Example 3.

FIG. 2 shows a plot of the Ct values shown in Table 9. The data in FIG. 2 labeled "CT Ratio" is the average Ct shown in Table 9, which is the average of three reactions. There was good separation between the lung cancer and healthy groups of the cohort. Only two of the lung cancer patients had Ct values that were higher than healthy individuals. In this experiment, about 90% of the lung cancer patients had elevated levels of small U2 compared to healthy individuals. At a Ct cut-off of 32.3, the sensitivity was 83.3% and the specificity was 100%.

Figure 6:
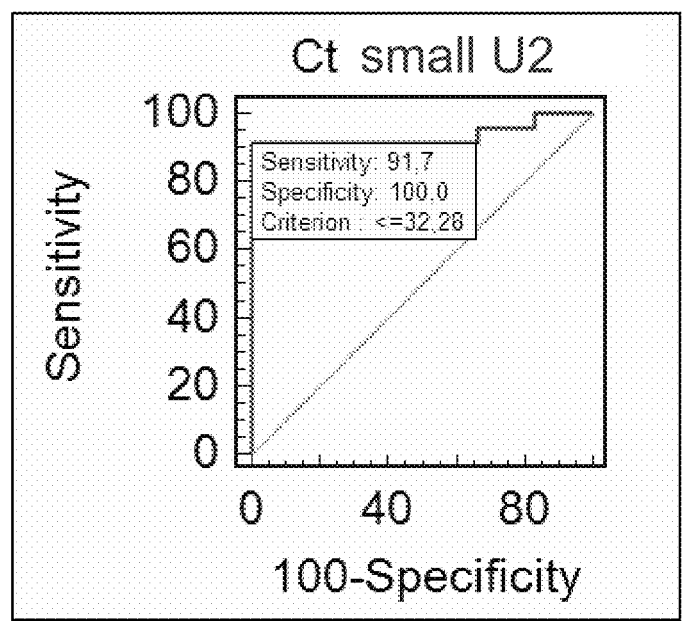
FIG. 6 shows a Received Operating Characteristic (ROC) plot of the data shown in FIG. 2, as described in Example 3.

A Receiver Operating Characteristic (ROC) plot of the data is shown in FIG. 6. The ROC plot shows good separation between lung cancer patients and healthy individuals. Measurement of serum levels of small U2 is able to identify individuals with lung cancer with 91.7% sensitivity at 100% specificity using a criterion of Ct≤32.28.

In this experiment, the level of small U2 in serum is a very good marker for lung cancer, and in addition, small U2 is suitable for detecting early-stage lung cancer using a minimally invasive assay.

TaqMan® quantitative RT-PCR (qRT-PCR; Applied Biosystems) assays were also used to measure levels of miR-720, miR-451, and 13207 in the total RNA samples isolated from the serum of the individuals in the cohort shown in Tables 7 and 8. The average Ct from three reactions is shown in Table 10 for each individual in the cohort, for each RNA, along with certain characteristics from Tables 7 and 8.

TABLE 10

Average Ct values for miR-720, miR-451 and 13207

| ID | Smoking Status | Clinical Diagnosis | Stage | Stage Group | CT miR-720 | CT miR-451 | CT 13207 |
|---|---|---|---|---|---|---|---|
| 47031 | Never Used | Papillary adenocarc. | T1NXM0 | IA | 31.52 | 26.83 | 33.97 |
| 48716 | 30 smokes/Day | Squamous cell carcinoma | T2N1M0 | IIB | 30.62 | 28.25 | 33.24 |
| 41379 | Never Used | Adenocarc. | T1NXM0 | IA | 29.26 | 23.84 | 34.04 |
| 48708 | 25 smokes/Day | Squamous cell carcinoma | T1N0M0 | IA | 28.63 | 25.36 | 33.18 |
| 48712 | Never Used | Squamous cell carcinoma | T2N0M0 | IB | 27.93 | 27.04 | 33.22 |
| 49129 | 20 smokes/Day | Adenocarc. | T2N0M0 | IB | 28.7 | 28.71 | 32.91 |
| 47044 | 20 smokes/Day | Squamous cell carcinoma | T2NXM0 | IB | 28.69 | na | 31.37 |
| 47042 | 20 smoke(s) | Squamous cell carcinoma | T2NXM0 | IB | 29.37 | na | 31.55 |
| 48714 | Never Used | Adenocarc. | T2N0M0 | IB | 28.25 | 25.88 | 32.13 |
| 45417 | 40 smokes/Day | Adenocarc. | T2N0MX | IB | 29.29 | 26.94 | 33.08 |
| 47322 | 15 smokes/Day | Squamous cell carcinoma | T2NXM0 | IB | 28.99 | 26.92 | 33.31 |
| 47033 | 30 smokes/Day | Adenocarc. | T1NXM0 | IA | 29.27 | 24.78 | 33.84 |
| 45937 | 15 smokes/Day | Adenocarc. | T2N1MX | IIB | 29.59 | 25.46 | 32.57 |
| 45926 | 20 smokes/Day | Adenocarc. | T2N0M0 | IB | 29.26 | 25.23 | 33.25 |
| 49137 | Never Used | Adenocarc. | T1N0M0 | IA | 28.98 | 26.96 | 32.7 |

TABLE 10-continued

Average Ct values for miR-720, miR-451 and 13207

| ID | Smoking Status | Clinical Diagnosis | Stage | Stage Group | CT miR-720 | CT miR-451 | CT 13207 |
|---|---|---|---|---|---|---|---|
| 45694 | Never Used | Bronchiolo-alveolar carcinoma | T1NXM0 | IA | 27.8 | na | 31.65 |
| 45424 | 40 smokes/Day | Squamous cell carcinoma | T2N1MX | IIB | 33.07 | 27.44 | 37.99 |
| 45419 | 20 smokes/Day | Adenocarc. | T2N0MX | IB | 28.49 | 22.48 | 33.38 |
| 41537 | 20 smokes/Day | Adenocarc. | T2N1MX | IIB | 29.17 | 24.5 | 33.02 |
| 44664 | 60 cig(s)/Day | Squamous cell carcinoma | T2N0M0 | IB | 28.42 | na | 31.55 |
| 45407 | 30 smokes/Day | Squamous cell carcinoma | T2N0MX | IB | 29.17 | 26.81 | 32.96 |
| 49136 | Previous Use | Squamous cell carcinoma | T2NXM0 | IB | 27.97 | 27.04 | 32.33 |
| 48710 | 30 smokes/Day | Adenocarc. | T2N0M0 | IB | 26.36 | 22.46 | 33.03 |
| 48711 | Never Used | Squamous cell carcinoma | T2N0M0 | IB | 28.02 | 25.56 | 32.65 |
| 50437 | Previous use | Healthy | | | 30.4 | 28.96 | 31.93 |
| 42199 | 3 smokes/day | Healthy | | | 31.73 | 30.11 | 32.68 |
| 49508 | Never Used | Healthy | | | 30.43 | 27.14 | 31.6 |
| 50444 | 10 smokes/day | Healthy | | | 31.58 | 28.8 | 31.91 |
| 49511 | Never Used | Healthy | | | 31.67 | 29.29 | 31.92 |
| 42214 | Previous use | Healthy | | | 31.47 | 29.44 | 32.19 |
| 50448 | Previous use | Healthy | | | 30.22 | 27.86 | 32.01 |
| 46816 | Never Used | Healthy | | | 31.4 | 28.29 | 31.83 |
| 49509 | Never Used | Healthy | | | 31.18 | 28.33 | 32.07 |
| 43517 | 20 smokes/day | Healthy | | | 31.25 | 29.34 | 31.93 |
| 46810 | Never Used | Healthy | | | 30 | 26.62 | 32.09 |
| 50446 | 4 smokes/day | Healthy | | | 29.59 | 25.76 | 31.8 |

Figure 3:
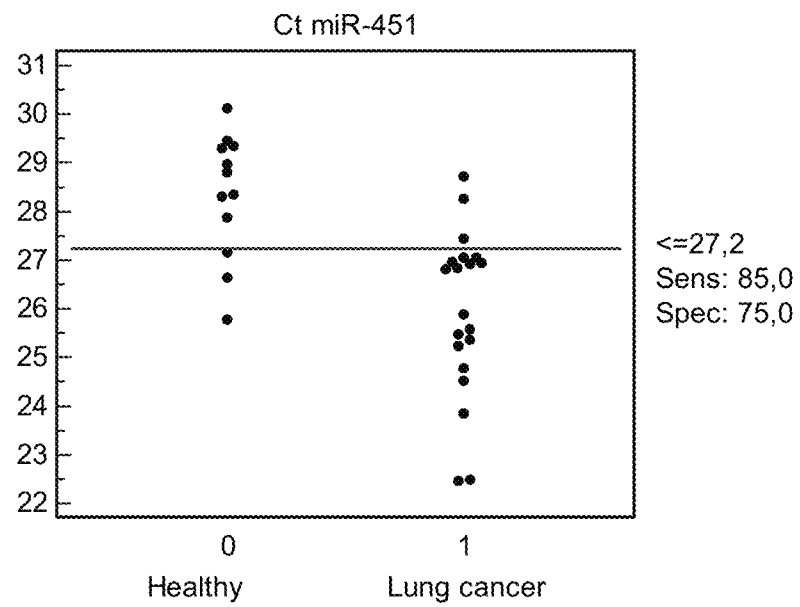
FIG. 3 shows a plot of the qRT-PCR Ct values for miR-451 in serum from lung cancer patients and healthy individuals, as described in Example 3.
Figure 4:
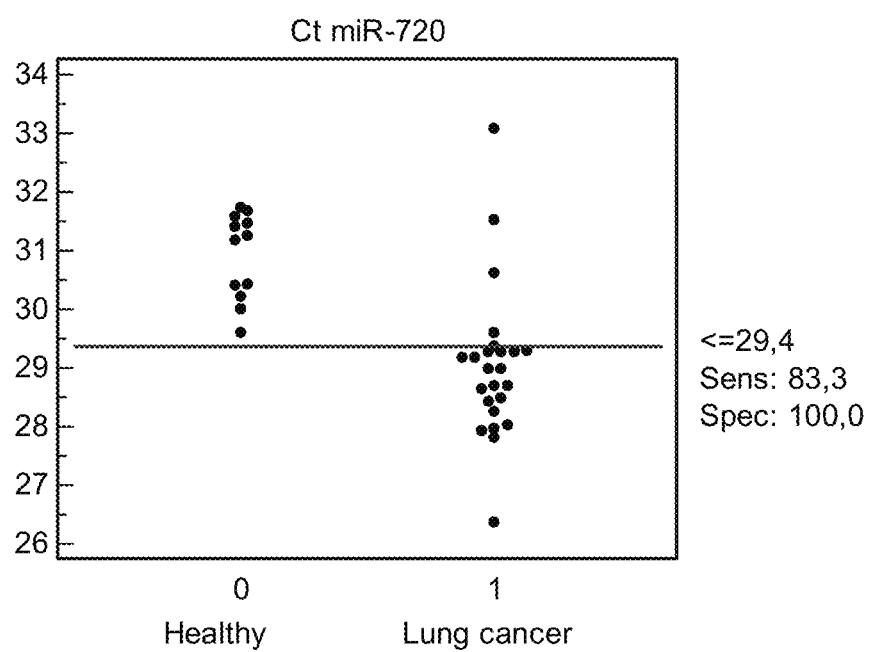
FIG. 4 shows a plot of the qRT-PCR Ct values for miR-720 in serum from lung cancer patients and healthy individuals, as described in Example 3.
Figure 5:
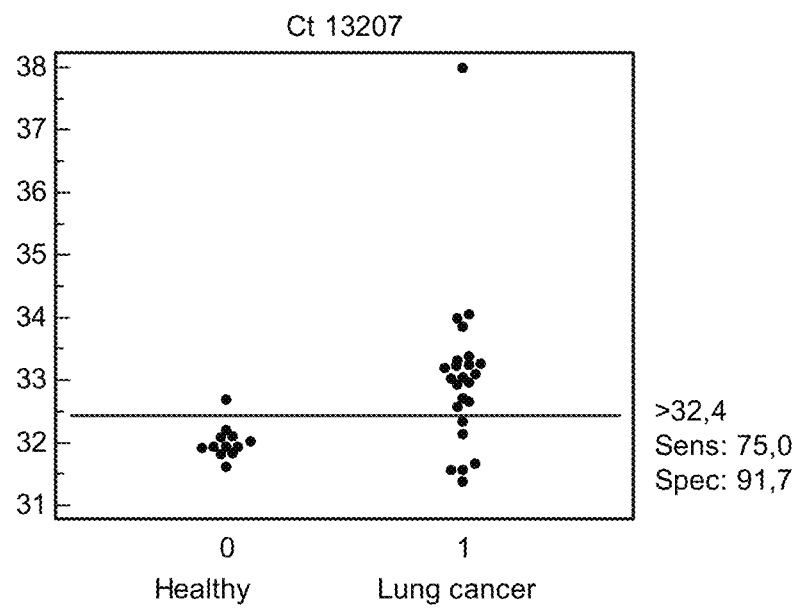
FIG. 5 shows a plot of the qRT-PCR Ct values for 13207 in serum from lung cancer patients and healthy individuals, as described in Example 3.

FIGS. 3 to 5 show plots of the Ct values for miR-451, miR-720, and 13207, respectively, from Table 10. As shown in FIG. 3, the sensitivity and specificity for the presence of lung cancer based on miR-451 levels were 85% and 75%, respectively. Further, while miR-451 appeared to be present at lower levels in primary tumor cells relative to normal cells, it was found to be present at increased levels in serum from a small cohort of lung cancer patients in this experiment. As shown in FIG. 4, the sensitivity and specificity for the presence of lung cancer based on miR-720 levels were 83.3% and 100%, respectively. Finally, as shown in FIG. 5, the sensitivity and specificity for the presence of lung cancer based on miR-13207 levels, which are lower in serum samples, were 75% and 91.7%, respectively.

5.4 Example 4

High Small U2 Levels are Associated with Lung Cancers

Selected Cohort

Twenty-eight patients diagnosed with non-lung cancers were selected for this cohort to determine if mature small U2 is specifically associated with lung cancer. Eight of the patients were diagnosed with colorectal cancer, five with bladder cancer, nine with breast cancer, and six with prostate cancer. Patients were included with a range of early to late stage cancers. In total, there were four patients at stage I, 14 patients at stage II, eight patients at stage III, and one patient at stage IV. None of the patients had been diagnosed with diabetes, infectious disease, other cancers, obesity, or cardiac problems. None of the patients were taking medication at the time of serum collection. Finally, 13 of the patients had a history of smoking. Table 11 lists all of the patients within the cohort and various clinical characteristics of each patient. Table 11 also shows the Ct value from the small U2 qRT-PCR assays discussed below.

TABLE 11

Clinical characteristics of non-lung cancer patients in cohort.

| ID | Age at Excision | Cancer Type | Gender | Smoking Status | Clinical Diagnosis | Stage | Stage Group | Average Ct |
|---|---|---|---|---|---|---|---|---|
| 30532 | 51 | | Male | 20 smokes/Day | Transitional cell carcinoma | T2bN0M0 | II | 35.8 |
| 39318 | 59 | | Male | 30 smokes/Day | Transitional cell carcinoma | T3aN0MX | III | 35.46 |
| 43019 | 59 | Colorectal | Male | never | Mucinous Adenocarcinoma of the colon | T3N0M0 | IIA | 34.55 |
| 30531 | 58 | | Male | 20 smokes/Day | Transitional cell carcinoma | T2NXMX | II | 34.27 |
| 43031 | 67 | Colorectal | Male | never | Adenocarcinoma of the colon | T2N0M0 | I | 34.26 |
| 47460 | 49 | Colorectal | Female | never | Adenocarcinoma of the colon | T3N0M0 | IIA | 34.07 |
| 20322 | 62 | prostate | Male | previous (41) | Adenocarcinoma | T3aNXMX | III | 34.02 |
| 21193 | 67 | | Male | never | Papillary transitional cell carcinoma | TXN0MX | II | 33.83 |
| 43571 | 65 | Colorectal | Female | 2 smokes/Day | Adenocarcinoma of the rectum | TXNXM0 | IB | 33.83 |
| 49870 | 42 | Breast | Female | never | Infiltrating ductal carcinoma | T1cNXMX | I | 33.81 |
| 13293 | 60 | | Female | previous (10) | Transitional cell carcinoma | T4N2MX | IV | 33.63 |
| 49001 | 55 | Breast | Female | never | Infiltrating ductal carcinoma | T1cN0M0 | I | 33.46 |

TABLE 11-continued

Clinical characteristics of non-lung cancer patients in cohort.

| ID | Age at Excision | Cancer Type | Gender | Smoking Status | Clinical Diagnosis | Stage | Stage Group | Average Ct |
|---|---|---|---|---|---|---|---|---|
| 47468 | 31 | Colorectal | Male | never | Mucinous Adenocarcinoma of the colon | T2N1M0 | IIIA | 33.44 |
| 43445 | 70 | prostate | Male | current (na) | Adenocarcinoma | T2N0M0 | II | 33.37 |
| 36492 | 37 | Breast | Female | 2 smokes/Day | Infiltrating ductal carcinoma | T1cNXM0 | I | 33.35 |
| 30567 | 47 | | Male | 25 smokes/Day | Papillary transitional cell carcinoma | T2bN0MX | II | 33.33 |
| 43969 | 64 | Breast | Female | never | Lobular carcinoma | T2N3M0 | IIIC | 32.95 |
| 19159 | 69 | prostate | Male | previous (20) | Adenocarcinoma | T2aN0M0 | II | 32.9 |
| 30545 | 67 | prostate | Male | previous (20) | Adenocarcinoma | T2cN0M0 | II | 32.75 |
| 43991 | 59 | Colorectal | Male | 6 smokes/Day | Adenocarcinoma of the rectum | T3NXM0 | IIA | 32.53 |
| 48433 | 54 | Breast | Female | never | Infiltrating ductal carcinoma | T2N2M0 | IIIA | 32.45 |
| 42979 | 66 | Colorectal | Female | never | Adenocarcinoma of the colon | T2N1MX | IIIA | 32.32 |
| 43994 | 57 | Breast | Female | never | Infiltrating ductal carcinoma | T1cN2M0 | IIIA | 32.26 |
| 47318 | 57 | Breast | Female | never | Carcinoma | T2NXM0 | IIA | 31.75 |
| 40017 | 58 | prostate | Male | never | Adenocarcinoma | T3bN0M0 | III | 31.45 |
| 49734 | 48 | Breast | Female | 5 smokes/Day | Infiltrating ductal carcinoma | T2N0M0 | IIA | 31.09 |
| 48574 | 48 | Breast | Female | never | Infiltrating ductal carcinoma | T2N1M0 | IIB | 31.01 |
| 49152 | 70 | Colorectal | Female | never | Adenocarcinoma of the colon | T3N1M0 | IIIB | 29.81 |

Detection of Small U2 in Serum of Non-Lung Cancer Patients by qRT-PCR

Total RNA from one ml of serum from each of the patients listed in Table 11 was isolated as described above in Example 3.

TaqMan® quantitative RT-PCR (qRT-PCR; Applied Biosystems) assays were used to measure small U2 levels in the total RNA samples isolated from the serum of the individuals in the cohort. The average Ct value from three assays is shown for each individual in Table 11.

Figure 7:
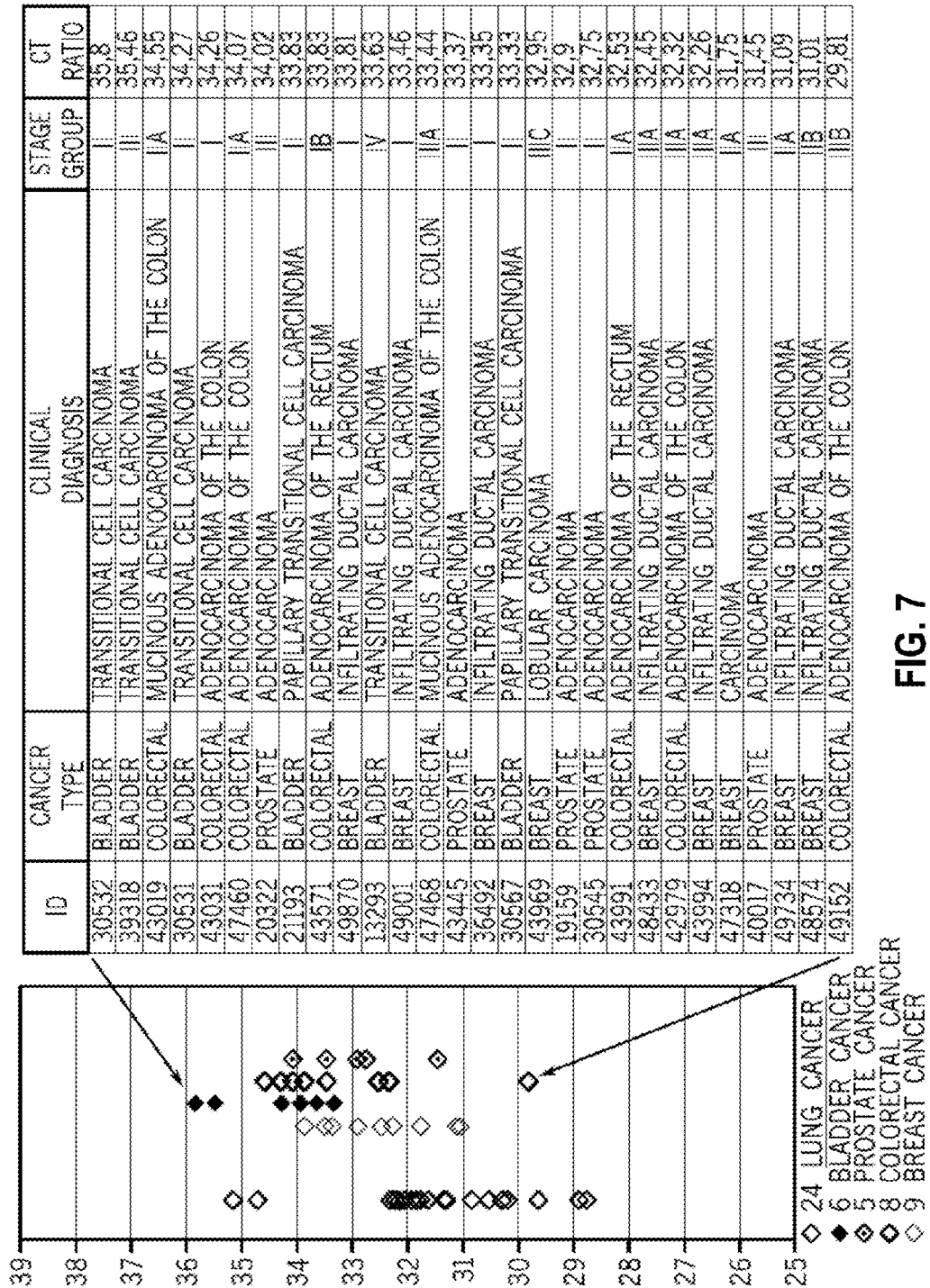
FIG. 7 shows a plot of the qRT-PCR Ct values for small U2 in serum from cancer patients with various types of cancers, as described in Example 4.

FIG. 7 shows a plot of the Ct values shown in Table 11. Each cancer type is plotted as a single column in the Figure. The data labeled as "Ct ratio" is the average Ct from three reactions, shown in Table 11. From left to right, the columns are lung cancer (data from Example 3), breast cancer, bladder cancer, colorectal cancer, and prostate cancer. Only six of the non-lung cancer patients had Ct values below the 100% specificity value (Ct=32.28) determined in Example 3. In contrast, 22 (79%) of the non-lung cancer patients had Ct values in a similar range as healthy individuals in Example 3. Thus, higher levels of small U2 are specifically associated with lung cancer.

Figure 8:
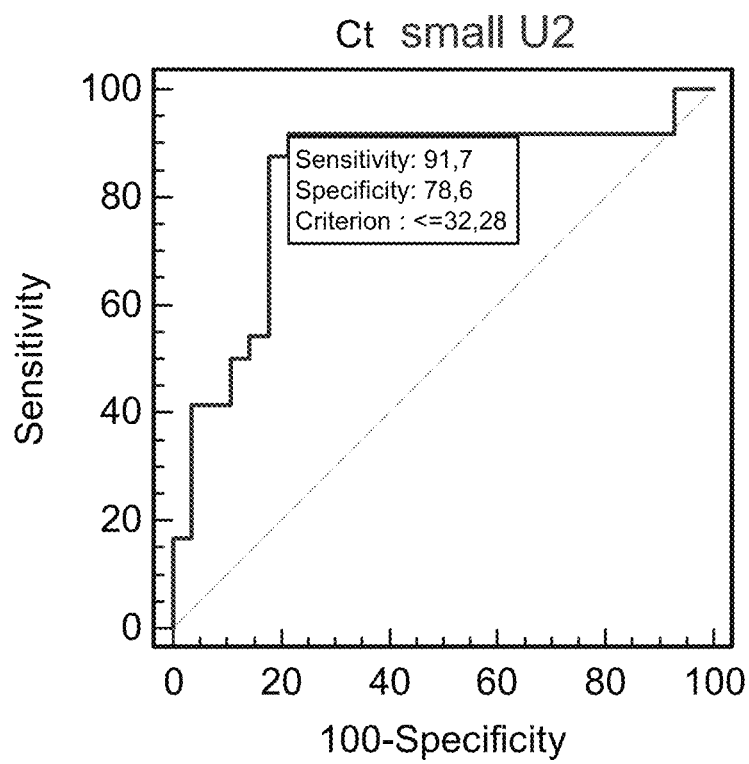
FIG. 8 shows a ROC plot of the data shown in FIG. 7, as described in Example 4.

A ROC plot of the data is shown in FIG. 8. The ROC plot shows good separation between lung cancer patients and non-lung cancer patients. Measurement of serum levels of small U2 is able to identify individuals with lung cancer versus other cancers with 91.7% sensitivity at 78.6% specificity using a criterion of Ct 32.28.

Of the six patients that had Ct values below the threshold (32.28), three of them had late-stage cancer (patients 43994, 40017 and 49152). Two more late-stage cancer patients had Ct values immediately above the threshold (48433 and 42979). Among the remaining 20 patients above the threshold, only three are at stage III and one at stage IV. Further, among the eight non-lung cancer patients very close to, or below, the threshold Ct value, five were breast cancer patients, suggesting the small U2 may more frequently be at higher levels in breast cancer. Four other breast cancer patients had higher Ct values, in the normal range. Overall, these results suggest that at later stages of cancer, small U2 levels may be higher in cancers other than lung. At earlier stages, however, small U2 levels are consistently high only in lung cancers.

MiR-720 was found to be less specific for lung cancer than small U2. A plot of the Ct values for miR-720 in patients with lung cancer and patients with other cancers showed a sensitivity of 83.3% and a specificity of 64.3% at a Ct cut-off of 29.4. (Data not shown.) When the other cancers are considered individually, miR-720 distinguished lung cancer from bladder cancer and prostate cancer, but not from breast cancer or colorectal cancer in that experiment. (Data not shown.) 13207 did not distinguish lung cancer from other cancers in that experiment. (Data not shown.)

5.5 Example 5

Identified Small RNAs are not Markers of Smoking Status or Gender

Figure 9:
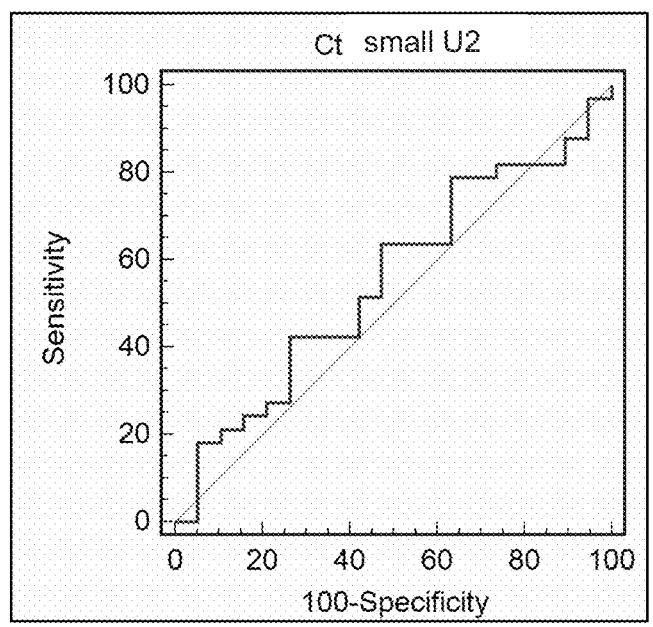
FIG. 9 shows a ROC plot of qRT-PCR Ct values for small U2 according to smoking history, as described in Example 5.

A ROC plot of Ct values for small U2 levels in all patients, including both cancer patients and healthy individuals, versus smoking history is shown in FIG. 9. That plot shows that small U2 is not a marker of smoking status. Similar results were obtained with miR-720, miR-451, and 13207. (Data not shown.)

When the Ct values were plotted according to the gender of the individual, small U2, miR-720, miR-451, and 13207 were also found not to be markers for gender. (Data not shown.)

Finally, combinations of the small RNAs, such as the combination of small U2 and miR-720, were also found not to be markers for gender or smoking status. (Data not shown.)

5.6 Example 6

Small RNA Combinations Improve Detection Sensitivity and Specificity

The Ct data shown in Table 9 (small U2) and Table 10 (miR-720, miR-451, and 13207) were combined in various ways to determine if the sensitivity and/or specificity of the assay would be improved. For each combination, the Ct values were added to one another (in the case of two RNAs that are both up-regulated) or subtracted from one another (in the case of an RNAs that is upregulated and an RNAs that is down-regulated).

Figure 10:
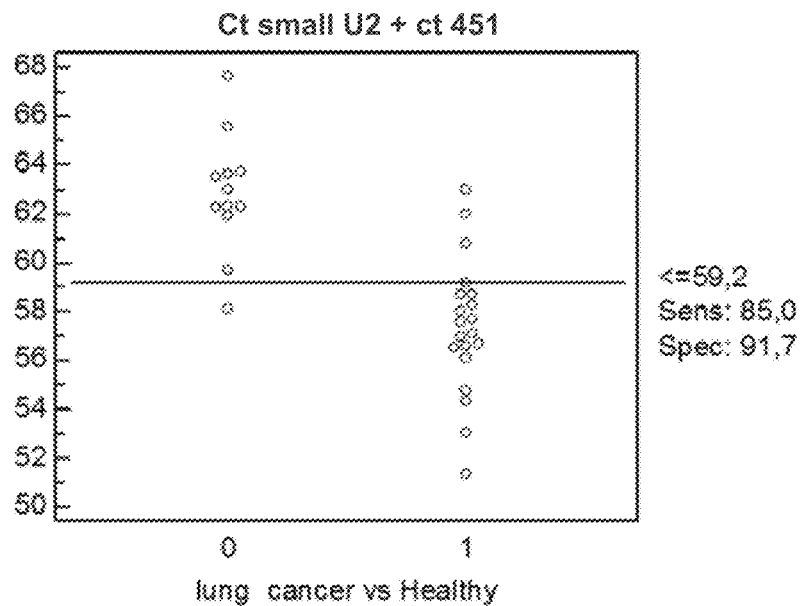
FIG. 10 shows a plot of the sum of the qRT-PCR Ct values for small U2 and miR-451 in serum from lung cancer patients and healthy individuals, as described in Example 6.

FIG. 10 shows the combination of small U2 and miR-451. The Ct values for small U2 and miR-451 for each patient were added together. The sensitivity and specificity were 85% and 91.7%, respectively, for the combination of small U2 and miR-451.

Figure 11:
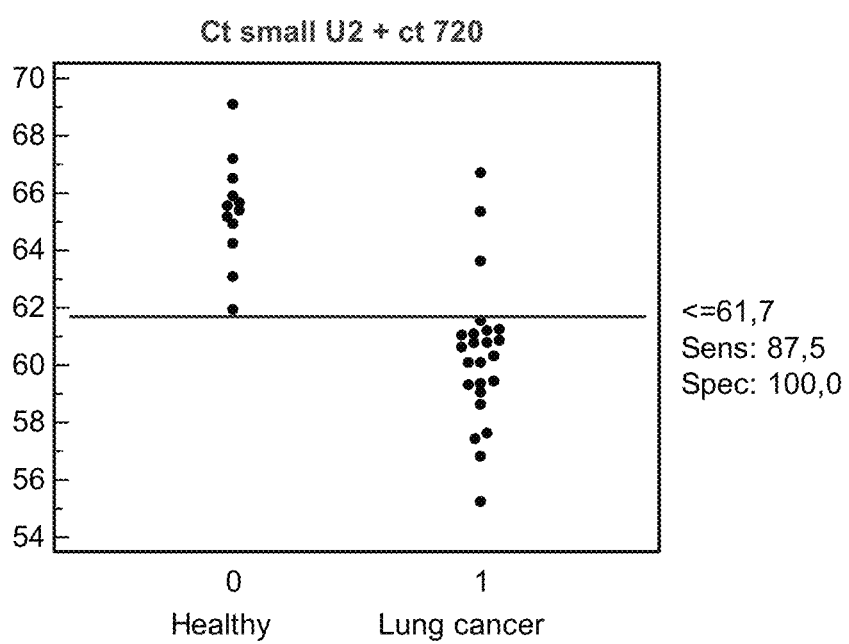
FIG. 11 shows a plot of the sum of the qRT-PCR Ct values for small U2 and miR-720 in serum from lung cancer patients and healthy individuals, as described in Example 6.

FIG. 11 shows the combination of small U2 and miR-720. The Ct values for small U2 and miR-720 for each patient were added together. The sensitivity and specificity were 87.5% and 100%, respectively, for the combination of small U2 and miR-720.

Figure 12:
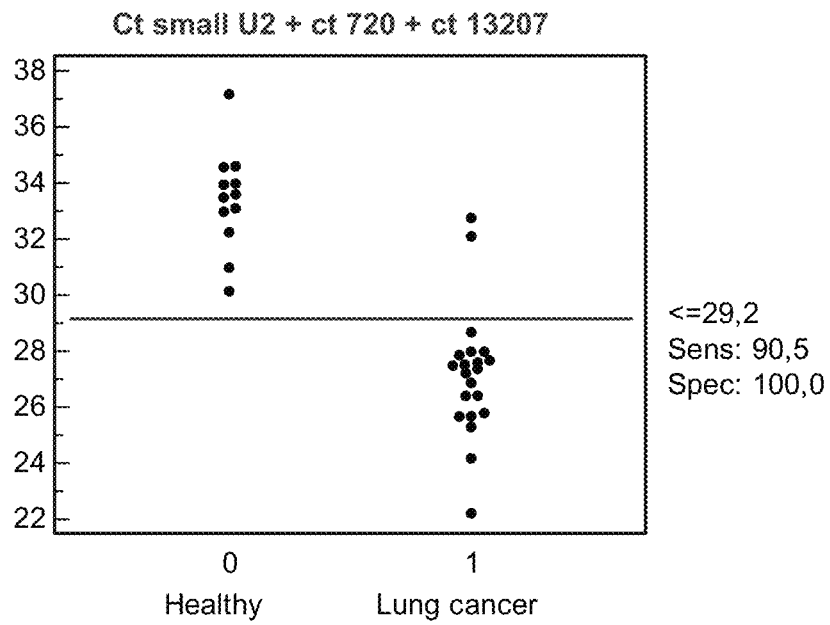
FIG. 12 shows a plot of the sum of the qRT-PCR Ct values for small U2 and miR-720, less the qRT-PCR Ct values for 13207, in serum from lung cancer patients and healthy individuals, as described in Example 6.

FIG. 12 shows the combination of small U2, miR-720, and 13207. The Ct values for 13207 were subtracted from the sum of the Ct values for small U2 and miR-720. The sensitivity and specificity were 90.5% and 100%, respectively, for the combination of small U2, miR-720, and 13207.

Table 12 summarizes the sensitivity and specificity data for small U2, miR-720, and 13207, and combinations thereof

TABLE 12

Sensitivity and specificity of certain small RNAs and combinations thereof for detecting lung cancer.

| RNA(s) | Lung cancer v. Healthy | |
| --- | --- | --- |
| | Sensitivity | Specificity |
| small U2 | 83.3 | 100 |
| 13207 | 75.0 | 91.7 |
| miR-720 | 83.3 | 100 |
| miR-451 | 85.0 | 75.0 |
| small U2 − 13207 | 83.5 | 100 |
| small U2 + miR-451 | 85.0 | 91.7 |
| small U2 + miR-720 | 87.5 | 100 |
| small U2 + miR-720-13207 | 90.5 | 100 |

Figure 13:
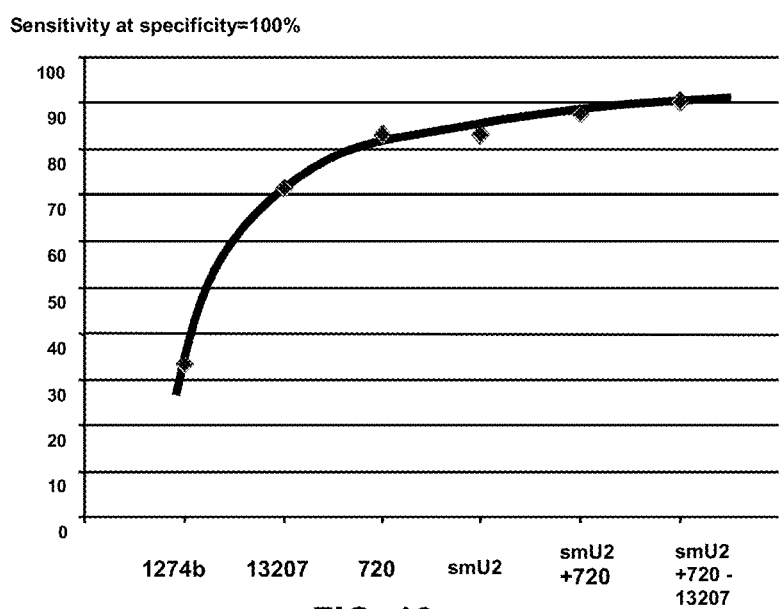
FIG. 13 shows a plot of the sensitivity of certain RNAs for detecting lung cancer when the specificity is set at 100%, as described in Example 6.

FIG. 13 shows a plot of sensitivity for detection of lung cancer by detecting certain RNAs, when the specificity is set at 100%. To set the specificity at 100%, the Ct cut-off is set such that all of the healthy samples are above (or below) the Ct cut-off line. The sensitivity is then determined with that Ct cut-off. As shown in that figure, the sensitivity increases when detection of certain small RNAs are combined.

Figure 14:
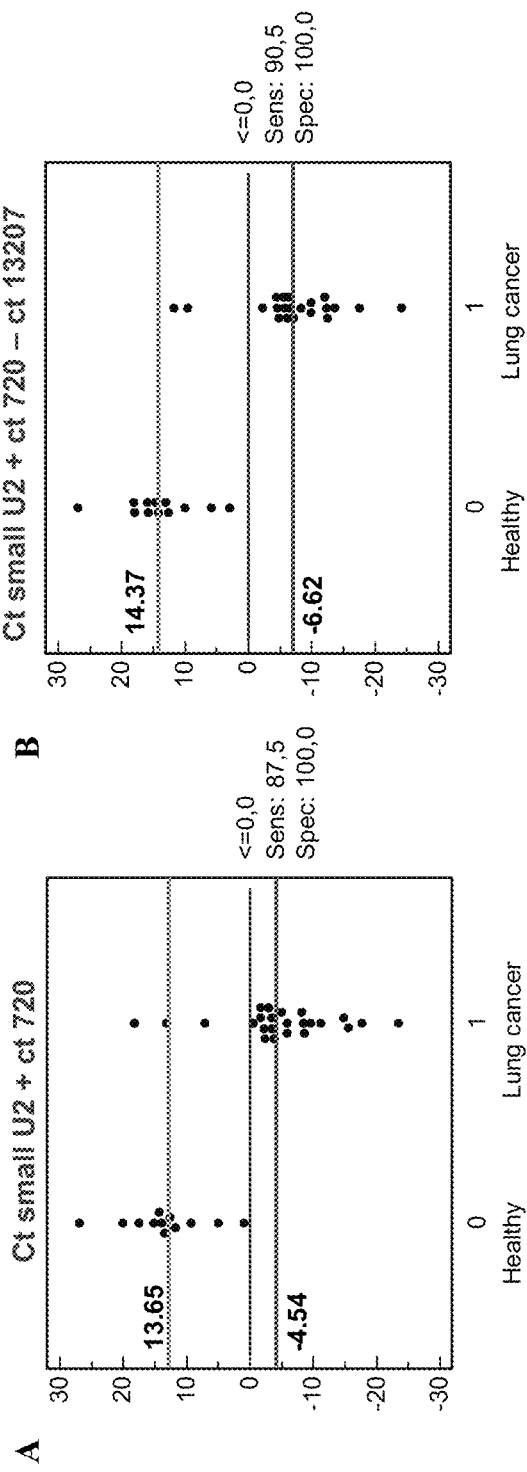
FIG. 14 shows plots of the normalized Cts for (A) the combination of small U2 and miR-720, and (B) the combination of small U2, miR-720, and 13207, as described in Example 6.

In order to determine the separation between the median Cts for certain RNA combinations in lung cancer patients versus healthy individuals, the Cts for the combination of small U2 and miR-720 and the Cts for the combination of small U2, miR-720, and 13207 were normalized as follows. First, the sum of the Cts was determined, as above (i.e., Ct(small U2)+Ct(miR-720); and Ct(small U2)+Ct(miR-720)−Ct(13207)). The sum of the Cts were then normalized to the 100% specificity cutoff: (((sum Cts)/(sum Cts at 100% specificity))−1)×100. As a result, the cut-off Ct is zero for both combinations. As shown in FIG. 14, in addition to increasing sensitivity, certain combinations of RNAs also result in greater separation between the median Cts for the lung cancer patients and healthy patients. The combination of small U2 and miR-720 (A) gives a specificity of 85.7 and a median separation of about 18 for the normalized data (as indicated by the distance between the upper and lower lines), while the combination of small U2, miR-720, and 13207 (B) gives a specificity of 90.5 and a median separation of about 21 for the normalized data (as indicated by the distance between the upper and lower lines).

5.7 Example 7

Small RNA Levels Determined by qRT-PCR in Another Cohort

Selected Cohort

Twenty-one individuals were selected, 11 of which had been diagnosed with lung cancer, and 10 of which were healthy. This study demonstrates that small U2 can be used as an early detection marker for lung cancer using a minimally invasive assay.

The 11 lung cancer patients had early-stage lung cancer: five were diagnosed with stage IA lung cancer, four with stage IB, and two with stage IIB. The cohort included six men and five women. Four of the patients were smokers, one was a former smoker, and six had never been smokers. None of the patients had been diagnosed with diabetes, infectious disease, other cancers, obesity, or cardiac problems. None of the patients were taking medication at the time the tissue was collected. The 10 healthy individuals in the cohort did not have any of diabetes, infectious disease, cancer, obesity, or cardiac problems. None of the healthy individuals were taking medication at the time tissue was collected. Table 13 shows the 11 patients with lung cancer in the cohort and various clinical characteristics of each patient, as well as the 10 healthy individuals in the cohort.

TABLE 13

Clinical characteristics of lung cancer patients in cohort-2

| ID | Age at Excision | Gender | Smoking Status | Clinical Diagnosis | Stage | Stage Group |
| --- | --- | --- | --- | --- | --- | --- |
| 49731 | 67 | Female | Never Used | Adenocarcinoma | T1NXM0 | IA |
| 51088 | 47 | Male | Current Use | Adenocarcinoma | T2NXM0 | IB |
| 51952 | 61 | Female | Never Used | Adenocarcinoma | T1N0M0 | IA |
| 55185 | 55 | Male | Previous Use | Adenocarcinoma | T3N0M0 | IIB |
| 45415 | 75 | Female | Never Used | Squamous cell carcinoma | T1N0M0 | IA |
| 47041 | 62 | Male | Current Use | Squamous cell carcinoma | T1NXM0 | IA |
| 49133 | 72 | Male | Current Use | Squamous cell carcinoma | T2N0M0 | IB |
| 50542 | 55 | Male | Current Use | Squamous cell carcinoma | T1N0M0 | IA |
| 55189 | 59 | Female | Never Used | Adenocarcinoma | T2aN0M0 | IB |
| 56318 | 50 | Male | Never Used | Adenocarcinoma | T2aNXM0 | IB |
| 52017 | 65 | Female | Never Used | Squamous cell carcinoma | T2N1M0 | IIB |
| 31473 | 25 | Female | Previous Use | Healthy | | |
| 31476 | 29 | Female | Current Use | Healthy | | |
| 31506 | 23 | Female | Never Used | Healthy | | |
| 55781 | 40 | Female | Current Use | Healthy | | |
| 31466 | 33 | Female | Never Used | Healthy | | |
| 31468 | 36 | Female | Current Use | Healthy | | |
| 31462 | 24 | Male | Current Use | Healthy | | |
| 31465 | 25 | Male | Never Used | Healthy | | |
| 31471 | 49 | Female | Never Used | Healthy | | |
| 31472 | 32 | Female | Current Use | Healthy | | |

For each individual in the cohort, 1 ml of serum was used to extract RNA for use in a TaqMan® quantitative RT-PCR assays (qRT-PCR; Applied Biosystems). RNA was isolated as described in Example 3.

TaqMan® quantitative RT-PCR assays were used to measure small RNA levels in the total RNA samples isolated from the serum of the individuals in the cohort. The small RNA levels detected were small U2, and miR-720, and CelmiR-39 (*C. elegans* miR-39). CelmiR-39 was added as a spike-in control to correct for variations in RNA purification from serum. The average Ct from three reactions is shown in Table 14 for each individual in the cohort, along with certain characteristics from Table 13.

TABLE 14

Average Ct for small U2, and miR-720, and CelmiR-39 spike-in control

| ID | Clinical Diagnosis | Stage | Stage Group | Ct CelmiR-39 | Ct small U2 | Ct miR-720 |
| --- | --- | --- | --- | --- | --- | --- |
| 49731 | Adeno-carcinoma | T1NXM0 | IA | 25.25 | 30.26 | 29.12 |
| 51088 | Adeno-carcinoma | T2NXM0 | IB | 22.98 | 29.6 | 28.73 |
| 51952 | Adeno-carcinoma | T1N0M0 | IA | 24.7 | 30.04 | 28.66 |
| 55185 | Adeno-carcinoma | T3N0M0 | IIB | 22.87 | 28.75 | 28.5 |
| 45415 | Squamous cell carcinoma | T1N0M0 | IA | 23.34 | 30.57 | 28.84 |
| 47041 | Squamous cell carcinoma | T1NXM0 | IA | 23 | 30.06 | 29.62 |
| 49133 | Squamous cell carcinoma | T2N0M0 | IB | 23.43 | 29.31 | 28.72 |
| 50542 | Squamous cell carcinoma | T1N0M0 | IA | 19.78 | 28.27 | 28.69 |
| 55189 | Adeno-carcinoma | T2aN0M0 | IB | 22.28 | 28.06 | 27.62 |
| 56318 | Adeno-carcinoma | T2aNXM0 | IB | 22.54 | 28.42 | 28.32 |
| 52017 | Squamous cell carcinoma | T2N1M0 | IIB | 22.92 | 31.72 | 28.8 |
| 31473 | Healthy | | | 23.92 | 31.6 | 29.49 |
| 31476 | Healthy | | | 22.78 | 30.66 | 28.65 |
| 31506 | Healthy | | | 23.35 | 31.07 | 29.25 |
| 55781 | Healthy | | | 22.85 | 31.07 | 29.29 |
| 31466 | Healthy | | | 23.37 | 32.35 | 29.83 |
| 31468 | Healthy | | | 21.6 | 31.84 | 30.06 |
| 31462 | Healthy | | | 22.94 | 32.06 | 29.21 |
| 31465 | Healthy | | | 22.51 | 29.87 | 28.7 |
| 31471 | Healthy | | | 22.5 | 30.4 | 28.08 |
| 31472 | Healthy | | | 22.49 | 31.86 | 29.78 |

Table 15 shows the ΔCt values for small U2 and miR-720, relative to the Ct values for CelmiR-39, by subtracting the Ct for CelmiR-39 from the Ct for each RNA and combination of RNAs. In addition, ΔCt values for the combination of U2 and miR-720 are also shown in Table 15.

TABLE 15

ΔCt values for small U2 and miR-720, and the combination thereof

| ID | Clinical Diagnosis | Stage | Stage Group | ΔCt small U2 | ΔCt miR-720 | ΔCt U2 + 720 |
| --- | --- | --- | --- | --- | --- | --- |
| 49731 | Adenocarc. | T1NXM0 | IA | 5.21 | 4.07 | 9.28 |
| 51088 | Adenocarc. | T2NXM0 | IB | 6.62 | 5.75 | 12.37 |
| 51952 | Adenocarc. | T1N0M0 | IA | 5.54 | 4.16 | 9.7 |
| 55185 | Adenocarc. | T3N0M0 | IIB | 6.08 | 5.83 | 11.91 |
| 45415 | Squamous cell carcinoma | T1N0M0 | IA | 7.23 | 5.5 | 12.73 |

TABLE 15-continued

ΔCt values for small U2 and miR-720, and the combination thereof

| ID | Clinical Diagnosis | Stage | Stage Group | ΔCt small U2 | ΔCt miR-720 | ΔCt U2 + 720 |
| --- | --- | --- | --- | --- | --- | --- |
| 47041 | Squamous cell carcinoma | T1NXM0 | IA | 7.06 | 6.62 | 13.68 |
| 49133 | Squamous cell carcinoma | T2N0M0 | IB | 5.88 | 5.29 | 11.17 |
| 50542 | Squamous cell carcinoma | T1N0M0 | IA | 8.49 | 8.91 | 17.4 |
| 55189 | Adenocarc. | T2aN0M0 | IB | 5.98 | 5.54 | 11.52 |
| 56318 | Adenocarc. | T2aNXM0 | IB | 6.08 | 5.98 | 12.06 |
| 52017 | Squamous cell carcinoma | T2N1M0 | IIB | 8.8 | 5.88 | 14.68 |
| 31473 | Healthy | | | 8.08 | 5.97 | 14.05 |
| 31476 | Healthy | | | 8.28 | 6.27 | 14.55 |
| 31506 | Healthy | | | 8.02 | 6.2 | 14.22 |
| 55781 | Healthy | | | 8.62 | 6.84 | 15.46 |
| 31466 | Healthy | | | 9.08 | 6.56 | 15.64 |
| 31468 | Healthy | | | 10.24 | 8.46 | 18.7 |
| 31462 | Healthy | | | 9.12 | 6.27 | 15.39 |
| 31465 | Healthy | | | 7.47 | 6.3 | 13.77 |
| 31471 | Healthy | | | 8 | 5.68 | 13.68 |
| 31472 | Healthy | | | 9.46 | 7.38 | 16.84 |

Figure 15:
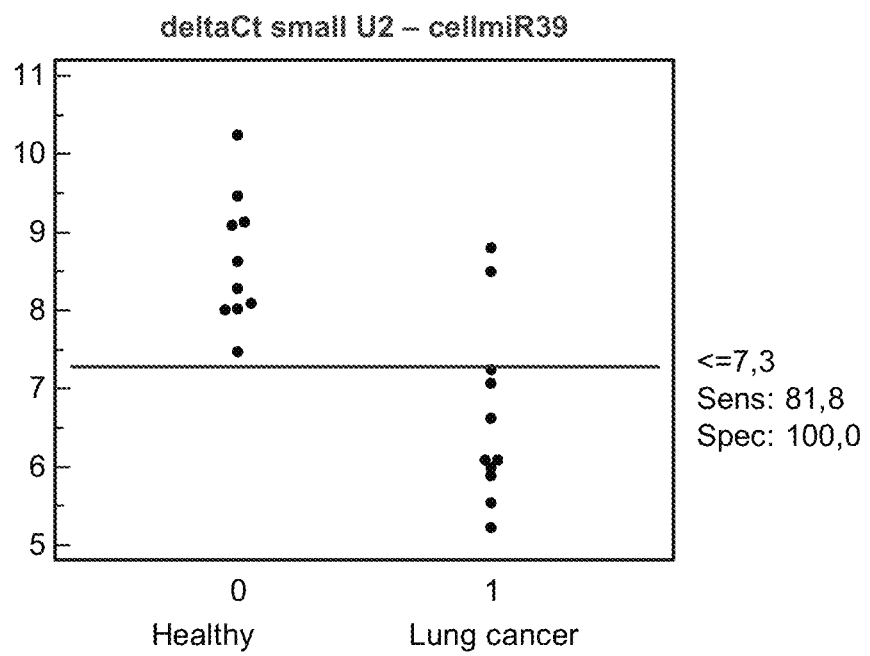
FIG. 15 shows a plot of the qRT-PCR ΔCt values for small U2, relative to CelmiR-39, in serum from lung cancer patients and healthy individuals, as described in Example 7.
Figure 16:
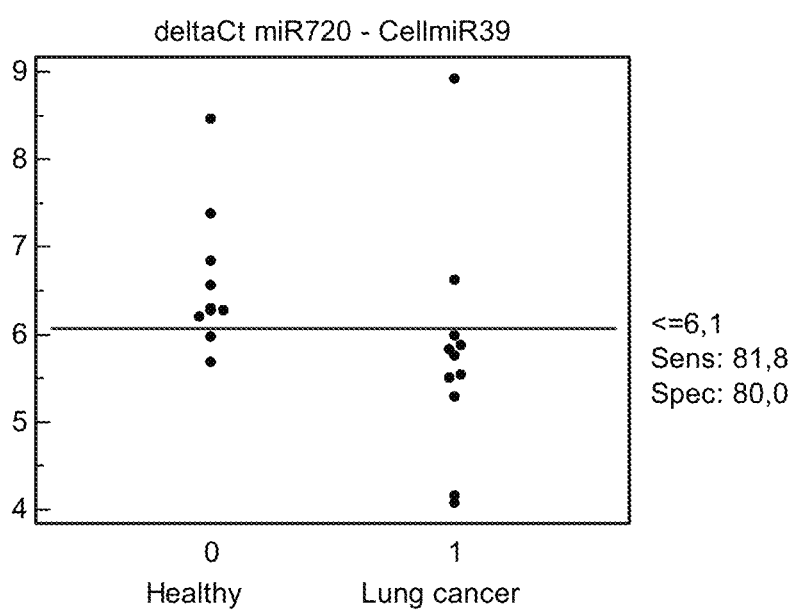
FIG. 16 shows a plot of the qRT-PCR ΔCt values for miR-720, relative to CelmiR-39, in serum from lung cancer patients and healthy individuals, as described in Example 7.

FIG. 15 shows a plot of the ΔCt values for small U2, relative to CelmiR-39. In this experiment, the ΔCt for small U2 gave a sensitivity of 81.8% and a specificity of 100% for detecting lung cancer. FIG. 16 shows a plot of the ΔCt values for miR-720, relative to CelmiR-39. In this experiment, the ΔCt for miR-720 gave a sensitivity of 81.8% and a specificity of 80% for detecting lung cancer.

Figure 17:
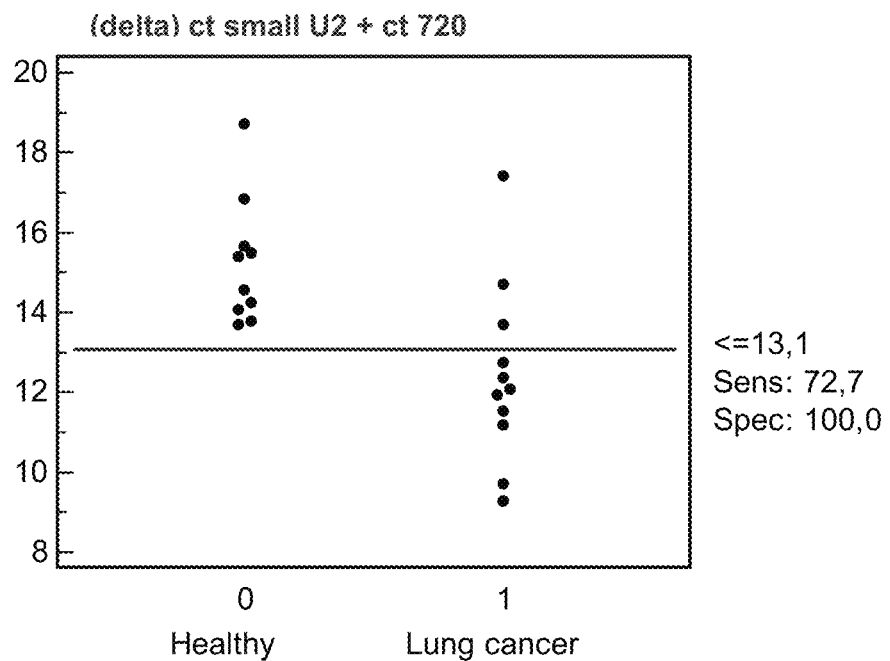
FIG. 17 shows a plot of the sum of the qRT-PCR ΔCt values for small U2 and miR-720, each relative to CelmiR039, in serum from lung cancer patients and healthy individuals, as described in Example 7.

FIG. 17 shows a plot of the sum of the ΔCt values for small U2 and miR-720, each relative to CelmiR-39. In this experiment, the sum of the ΔCt values gave a sensitivity of 72.7% and a specificity of 100% for detecting lung cancer.

5.8 Example 8

Preliminary Sequencing of Small RNAs from Serum

Small RNAs were sequenced from two different pools of serum from stage IA, IIA, IB, and IIB lung cancer patients: Pool I included serum from 15 patients and Pool II included serum from three patients. Small RNAs were also sequenced from a pool of serum from three healthy individuals. In addition, small RNAs were sequenced from two primary lung tumor samples, an adenocarcinoma and a squamous cell carcinoma. For Pool I, small RNAs (length <200 nucleotides) were purified using a mirVana™ miRNA isolation kit and sequenced by Fasteris SA (Switzerland). For primary tumors, RNA was size-fractionated and sequenced by Fasteris SA. For Pool II and serum from healthy individuals, total RNA was extracted by Norgen Biotek (Canada) and sequenced at LC Sciences (Houston, Tex.).

The following list shows some of the small RNA sequences that were sequenced from at least one of the pools of serum from lung cancer patients or in at least one of the primary lung tumor samples:

(SEQ ID NO: 2; small U2)
5'-UGGAUUUUUGGAGCAGGG-3'

(SEQ ID NO: 3; small U2)
5'-AAAUGGAUUUUUGGAGCAGGGAGAUGGAAU-3'

-continued

```
                           (SEQ ID NO: 4; small U2)
5'-AAAUGGAUUUUUGGAGCAGGGAGAU-3'

(SEQ ID NO: 5; small U2)
5'-AAAUGGAUUUUUGGAGCAGGGAGA-3'

(SEQ ID NO: 6; small U2)
5'-AAAUGGAUUUUUGGAGCAGGGAG-3'

(SEQ ID NO: 7; small U2)
5'-AAAUGGAUUUUUGGAGCAGGGA-3'

(SEQ ID NO: 8; small U2)
5'-AAAUGGAUUUUUGGAGCAGGG-3'

(SEQ ID NO: 9; small U2)
5'-AAUGGAUUUUUGGAGCAGGGAGAU-3'

(SEQ ID NO: 10; small U2)
5'-AAUGGAUUUUUGGAGCAGGGAGA-3'

(SEQ ID NO: 11; small U2)
5'-AAUGGAUUUUUGGAGCAGGGAG-3'

(SEQ ID NO: 12; small U2)
5'-AAUGGAUUUUUGGAGCAGGGA-3'

(SEQ ID NO: 13; small U2)
5'-AUGGAUUUUUGGAGCAGGGAGAU-3'

(SEQ ID NO: 14; small U2)
5'-AUGGAUUUUUGGAGCAGGGAGA-3'

(SEQ ID NO: 15; small U2)
5'-AUGGAUUUUUGGAGCAGGGAG-3'

(SEQ ID NO: 16; small U2)
5'-AUGGAUUUUUGGAGCAGGGA-3'

(SEQ ID NO: 17; small U2)
5'-AUGGAUUUUUGGAGCAGGG-3'

(SEQ ID NO: 18; small U2)
5'-UGGAUUUUUGGAGCAGGGAGA-3'

(SEQ ID NO: 19; small U2)
5'-UGGAUUUUUGGAGCAGGGAG-3'

(SEQ ID NO: 20; small U2)
5'-UGGAUUUUUGGAGCAGGGA-3'

(SEQ ID NO: 21; miR-720)
5'-UCUCGCUGGGGCCUCCA-3';

(SEQ ID NO: 23; miR-720)
5'-AUCUCGCUGGGGCCUCCA-3';

(SEQ ID NO: 24; miR-451)
5'-AAACCGUUACCAUUACUGAGUU-3';

(SEQ ID NO: 29; miR-451)
5'-AAACCGUUACCAUUACUGAGU-3';

(SEQ ID NO: 30; miR-451)
5'-AAACCGUUACCAUUACUGAG-3';

(SEQ ID NO: 28; miR-451)
5'-AAACCGUUACCAUUACUGAGUUU-3';

(SEQ ID NO: 27; miR-451)
5'-UUUAGUAAUGGUAAUGGUUCU-3';

(SEQ ID NO: 26; miR-451)
5'-UAAUGGUAAUGGUUCUCUUG-3';

(SEQ ID NO: 31; 13207)
5'-UGUCUUUCCUUGUUGGAGCAGG-3';

(SEQ ID NO: 35; 13750)
5'-TGTAGAGCAGGGAGCAGGAAGCT-3';

(SEQ ID NO: 38; 13750)
5'-TGTAGAGCAGGGAGCAGGAAGC-3';

(SEQ ID NO: 39; 13750)
5'-TGTAGAGCAGGGAGCAGGAAG-3';

(SEQ ID NO: 40; 13750)
5'-TGTAGAGCAGGGAGCAGGAA-3';
and
                           (SEQ ID NO: 41; 13750)
5'-TGTAGAGCAGGGAGCAGGA-3'.
```

5.9 Example 9

Small RNA Levels Determined by qRT-PCR in a Larger Cohort

Selected Cohort

One hundred and seventy-four individuals were selected for this cohort. One group of individuals were healthy, with no known cancer or inflammatory or infectious disease; one group of individuals had been diagnosed with other cancers, various inflammatory diseases, such as asthma, allergies, and sarcoidosis, and/or various infectious diseases (these individuals are divided into "MD" and "SI" groups; "MD" indicated mild disease and "SI" indicates "serious illness"); one group of individuals had been diagnosed with chronic obstructive pulmonary disease (COPD) and lung cancer; one group of individuals had been diagnosed with COPD, but without lung cancer; one group of individuals had been diagnosed with lung cancer; and one group of individuals had been diagnosed with lung fibrosis. In addition, nine individuals were suspected of having lung cancer, but had no confirmed diagnosis at the time of sample collection. Those individuals were used for validating the markers, and not for the initial analysis, as discussed below. Table 16 shows the clinical characteristics of the patients in the cohort.

TABLE 16

Clinical characteristics of patients in cohort

| ID | Age | Gender | Smoking Status | Group Status | SubGroup Status | Cancer history | Other Disease | Cancer type | SCLC | Cancer Stage | Relapse | Metastasis |
|---|---|---|---|---|---|---|---|---|---|---|---|---|
| SA-112 bis | 49 | M | never | Control | no disease | | | | | | | |
| SA-103a | 44 | F | smoker | Control | no disease | | | | | | | |
| SA-104 | 51 | M | never | Control | no disease | | | | | | | |
| SA-105 | 51 | M | smoker | Control | no disease | | | | | | | |
| SA-106 | 52 | F | never | Control | no disease | | | | | | | |
| SA-107 | 37 | M | smoker | Control | no disease | | | | | | | |

TABLE 16-continued

Clinical characteristics of patients in cohort

| ID | Age | Gender | Smoking Status | Group Status | SubGroup Status | Cancer history | Other Disease | Cancer type | SCLC | Cancer Stage | Relapse | Metastasis |
|---|---|---|---|---|---|---|---|---|---|---|---|---|
| SA-108 bis | 42 | M | never | Control | no disease | | | | | | | |
| SA-109 | 48 | M | never | Control | no disease | | | | | | | |
| SA-110 | 43 | M | smoker | Control | no disease | | | | | | | |
| SA-111 | 41 | F | never | Control | no disease | | | | | | | |
| SA-113 | 59 | M | never | Control | no disease | | | | | | | |
| SA-114 | 46 | M | never | Control | no disease | | | | | | | |
| SA-115 | 45 | M | smoker | Control | no disease | | | | | | | |
| SA-116 | 57 | F | never | Control | no disease | | | | | | | |
| SA-117 | 44 | M | never | Control | no disease | | | | | | | |
| SA-118 | 46 | F | never | Control | no disease | | | | | | | |
| SA-119 | 45 | M | never | Control | no disease | | | | | | | |
| SA-120 | 57 | F | never | Control | no disease | | | | | | | |
| SA-121 | 58 | M | smoker | Control | no disease | | | | | | | |
| SA-122 | 59 | F | never | Control | no disease | | | | | | | |
| SA-123 | 42 | F | never | Control | no disease | | | | | | | |
| SA-124 | 52 | F | never | Control | no disease | | | | | | | |
| SA-125 | 39 | M | never | Control | no disease | | | | | | | |
| SA-126 | 61 | M | never | Control | no disease | | | | | | | |
| SA-127 | 40 | F | never | Control | no disease | | | | | | | |
| SA-128 | 38 | F | never | Control | no disease | | | | | | | |
| SA-129 | 42 | M | never | Control | no disease | | | | | | | |
| SA-130 | 48 | M | smoker | Control | no disease | | | | | | | |
| SA-131 | 51 | F | never | Control | no disease | | | | | | | |
| SA-132 | 38 | M | never | Control | no disease | | | | | | | |
| SA-133 | 54 | M | smoker | Control | no disease | | | | | | | |
| SA-134 | 45 | F | never | Control | no disease | | | | | | | |
| SA-135 | 62 | M | never | Control | no disease | | | | | | | |
| SA-136 | 54 | M | never | Control | no disease | | | | | | | |
| SA-137 | 67 | M | never | Control | no disease | | | | | | | |
| SA-138 | 43 | M | smoker | Control | no disease | | | | | | | |
| SA-CTL-126 | 52 | M | never | Control | no disease | | | | | | | |
| SA-CTL-127 | 44 | M | never | Control | no disease | | | | | | | |
| SA-CTL-128 | 44 | M | never | Control | no disease | | | | | | | |
| SA-CTL-129 | 33 | M | smoker | Control | no disease | | | | | | | |
| SA-CTL-130 | 33 | M | never | Control | no disease | | | | | | | |
| SA-CTL-131 | 35 | M | smoker | Control | no disease | | | | | | | |
| SA-CTL-132 | 30 | F | never | Control | no disease | | | | | | | |
| SA-CTL-133 | 46 | F | never | Control | no disease | | | | | | | |
| SA-CTL-578 | 41 | F | never | Control | no disease | | | | | | | |
| SL-04 | 40 | F | never | Control MD | | | sarcoidosis | | | | | |
| SL-159 | 19 | M | never | Control MD | | | allergies | | | | | |
| SL-190_500 | 22 | M | na | Control MD | | | asthma, allergies | | | | | |
| SL-163 | 40 | F | never | Control MD | | | allergies | | | | | |
| SL-99 | 23 | F | na | Control MD | | | sarcoidosis | | | | | |
| SL-161 | 39 | F | smoker | Control MD | | | asthma | | | | | |
| SL-188_500 | 24 | F | na | Control MD | | | asthma, allergies | | | | | |
| SL-164 | 27 | F | smoker | Control MD | | | allergies | | | | | |
| SL-167 | 33 | M | never | Control MD | | | allergies | | | | | |
| SL-165 | 18 | F | never | Control MD | | | allergies | | | | | |
| SL-93 | 55 | F | never | Control MD | | | asthma | | | | | |
| SL-160 | 26 | F | never | Control MD | | | allergies | | | | | |
| SL-92 | 40 | F | na | Control MD | | | asthma | | | | | |
| SL-162 | 23 | M | never | Control MD | | | allergies | | | | | |
| SL-166 | 31 | M | former | Control MD | | | allergies | | | | | |
| SL-104 | 61 | M | na | Control SI | melanoma | melanoma | Pulmonary infection | | | | | |
| SL-18 | 42 | F | former | Control SI | | | pneumothorax | | | | | |
| SL-97 | 59 | F | na | Control SI | bronchectasia | | Bronchectasia | | | | | |
| SL-30 | 79 | F | never | Control SI | bronchectasia | | bronchectasia | | | | | |
| SL-82 | 45 | M | smoker | Control SI | infectious | | infection: *Fusobacterium nucleatum* | | | | | |

TABLE 16-continued

Clinical characteristics of patients in cohort

| ID | Age | Gender | Smoking Status | Group Status | SubGroup Status | Cancer history | Other Disease | Cancer type | SCLC | Cancer Stage | Relapse | Metastasis |
|---|---|---|---|---|---|---|---|---|---|---|---|---|
| SL-29 | 72 | M | never | Control SI | kidney Cancer | fibromyxo-sarcoma | Lipome | | | | | |
| SL-124 | 45 | F | na | Control SI | hamarto-chondromia | | hamarto-chondrome | | | | | |
| SL-05 | 56 | M | smoker | Control SI | | | | | | | | |
| SL-138 | 71 | F | never | Control SI | breast cancer | breast cancer | | | | | | |
| SL-14 | 80 | F | na | Control SI | inflammation | | polyarthrite rhumatoïde | | | | | |
| SL-94 | 58 | F | na | Control SI | breast Cancer | breast neoplasia | mycobactériose | | | | | |
| SL-139 | 37 | M | never | Control SI | | | cough | | | | | |
| SL-111 | 42 | M | na | Control SI | bronchectasia | | asthma | | | | | |
| SL-95 | 56 | M | na | Control SI | tuberculosis | | Tuberculosis | | | | | |
| SL-03 | 65 | F | smoker | COPD + lung cancer | | | | SCC | | IIB | 1 | 0 |
| SL-79 | 62 | F | smoker | COPD + lung cancer | | 1st lung Cancer | | Adk | 0 | IIIA | 1 | 0 |
| SL-115 | 60 | M | smoker | COPD + lung cancer | | | | SCC | 0 | IIIA | 0 | 0 |
| SL-140_500 | 64 | M | smoker | COPD + lung cancer | | | | | | IIB | 0 | 0 |
| SL-81 | 73 | M | former | COPD + lung cancer | | | | Adk | 0 | IV | 0 | 1 |
| SL-110 | 69 | M | former | COPD + lung cancer | | | | SCC | 0 | IB | 1 | 0 |
| SL-42 | 65 | M | former | COPD + lung cancer | | | | Adk | 0 | IV | 0 | 1 |
| SL-08 | 68 | F | smoker | COPD + lung cancer | | | | Adk | 0 | IA | 0 | 0 |
| SL-91 | 55 | M | smoker | COPD + lung cancer | | | | Adk | 0 | IB | 0 | 0 |
| SL-45 | 84 | M | former | COPD + lung cancer | | | | SCC | 0 | IIB | 0 | 0 |
| SL-100 | 53 | M | smoker | COPD + lung cancer | | | | Adk | 0 | IA | 0 | 0 |
| SL-107 | 51 | M | smoker | COPD + lung cancer | | | | SCC | 0 | IIIB | 0 | 0 |
| SL-65 | 75 | M | former | COPD + lung cancer | | | | Adk | 0 | IIIA | 0 | 0 |
| SL-72 | 70 | F | smoker | COPD + lung cancer | | | | SCC | 0 | IV | 0 | 0 |
| SL-49 | 85 | F | smoker | COPD + lung cancer | | | | SCC | 0 | ND | 0 | 0 |
| SL-75 | 67 | M | smoker | COPD + lung cancer | | vesical Cancer | | Adk | 0 | IB | 0 | 0 |
| SA-95 | 66 | F | smoker | COPD − lung cancer | | | | | | | | |
| SA-96a | 70 | M | former | COPD − lung cancer | | | | | | | | |
| SA-97 | 53 | M | smoker | COPD − lung cancer | | | | | | | | |
| SA-98a | 57 | F | smoker | COPD − lung cancer | | | | | | | | |
| SL-152 | 70 | M | former | COPD − lung cancer | | | | | | | | |
| SL-149 | 64 | F | smoker | COPD − lung cancer | | | | | | | | |
| SL-146 | 68 | M | former | COPD − lung cancer | | | | | | | | |
| SL-153 | 56 | M | former | COPD − lung cancer | | | | | | | | |
| SL-169_500 | 64 | M | former | COPD − lung cancer | | | | | | | | |
| SL-154 | 66 | M | former | COPD − lung cancer | | | | | | | | |
| SL-143 | 76 | M | former | COPD − lung cancer | | | | | | | | |
| SL-150 | 56 | M | former | COPD − lung cancer | | | | | | | | |
| SL-141 | 60 | F | smoker | COPD − lung cancer | | | | | | | | |
| SL-142 | 45 | M | smoker | COPD − lung cancer | | | | | | | | |

TABLE 16-continued

Clinical characteristics of patients in cohort

| ID | Age | Gender | Smoking Status | Group Status | SubGroup Status | Cancer history | Other Disease | Cancer type | SCLC | Cancer Stage | Relapse | Metastasis |
|---|---|---|---|---|---|---|---|---|---|---|---|---|
| SL-06 | 65 | M | former | COPD – lung cancer | | | | | | | | |
| SL-170_500 | 59 | M | former | COPD – lung cancer | | | | | | | | |
| SL-172_500 | 54 | M | former | COPD – lung cancer | | | | | | | | |
| SL-134 | 80 | M | former | COPD – lung cancer | | | | | | | | |
| SL-151 | 62 | M | former | COPD – lung cancer | | | | | | | | |
| SL-98 | 74 | F | former | COPD – lung cancer | | | COPD | | | | | |
| SL-176_500 | 66 | M | former | COPD – lung cancer | | | | | | | | |
| SL-127 | 72 | M | na | COPD – lung cancer | | | | | | | | |
| SL-156 | 69 | M | former | fibrosis | | | | | | | | |
| SL-130 | 79 | M | former | fibrosis | | | | | | | | |
| SL-157 | 75 | M | never | fibrosis | | | | | | | | |
| SL-137 | 71 | F | never | fibrosis | | | | | | | | |
| SL-171_500 | 64 | M | passive | fibrosis | | | COPD | | | | | |
| SL-46 | 32 | M | never | Lung Cancer | | | | other | | IIA | 0 | 0 |
| SL-47 | 63 | F | never | Lung Cancer | | | | Adk | | IV | 0 | 1a |
| SL-57 | 54 | F | smoker | Lung Cancer | | | | Adk | | IA | 0 | 1a |
| SL-80 | 70 | M | former | Lung Cancer | | | | SCC | | IV | 0 | 1 |
| SL-106 | 58 | F | former | Lung Cancer | | | Lupus, allergy | Adk | | 0 | 0 | 0 |
| SL-105 | 62 | F | never | Lung Cancer | | | | Adk | | IIIA | 1 | 0 |
| SL-71 | 65 | M | never | Lung Cancer | | | | Adk | | IIIA | 0 | 0 |
| SL-67 | 64 | M | former | Lung Cancer | | | | Adk | | IV | 0 | 1 |
| SL-58 | 57 | F | former | Lung Cancer | | | | SCLC | 1 | IIIB | 0 | 0 |
| SL-54 | 53 | M | former | Lung Cancer | | | | Other | | IIIA | 0 | 0 |
| SL-41 | 64 | M | na | Lung Cancer | | | | Other | | IIIA | 0 | 0 |
| SL-108 | 67 | M | former | Lung Cancer | | | | SCLC | 1 | IV | 0 | 1 |
| SL-61 | 53 | F | former | Lung Cancer | | | | LCNC | | IIIA | 0 | 0 |
| SL-66 | 60 | M | former | Lung Cancer | | | | SCC | | IIIA | 0 | 0 |
| SL-63 | 46 | M | smoker | Lung Cancer | | | | Adk | | IIIB | 0 | 0 |
| SL-60 | 64 | M | former | Lung Cancer | | | | Adk | | IB | 0 | 0 |
| SL-89 | 71 | F | na | Lung Cancer | | | | Adk | | IIA | 0 | 0 |
| SL-43 | 75 | M | former | Lung Cancer | | | | Other | | IV | na | 1 |
| SL-62 | 73 | M | smoker | Lung Cancer | | | | Adk | | IIB | 0 | 0 |
| SL-44 | 60 | M | na | Lung Cancer | | | Asthma | Adk | | IA | 0 | 0 |
| SL-70 | 72 | F | smoker | Lung Cancer | | | | Adk | | IIIA | 2nd cancer | 0 |
| SL-90 | 56 | M | smoker | Lung Cancer | | | | Other | | IB | 0 | 0 |
| SL-96 | 50 | M | former | Lung Cancer | | | | Adk | | IV | 0 | 1 |
| SL-64 | 51 | M | smoker | Lung Cancer | | | | LCNC | | IV | 0 | 1 |
| SL-50 | 67 | M | smoker | Lung Cancer | | | | SCC | | IIA | 0 | 0 |
| SL-59 | 58 | M | smoker | Lung Cancer | | | | SCC | | IV | na | 1 |
| SL-51 | 55 | F | smoker | Lung Cancer | | endometrial Cancer | | Adk | | IIIA | 0 | 0 |
| SL-78 | 73 | M | former | Lung Cancer | | Prostate Cancer | | SCC | | IIIA | 1 | 0 |
| SL-34 | 56 | M | former | Lung Cancer | | | | Other | | IIIB | 0 | 0 |
| SL-87 | 38 | M | never | Lung Cancer | | | | Adk | | IV | 0 | 1a |
| SL-77 | 57 | M | na | Lung Cancer | | | | Adk | | IV | | 1 |
| SL-73 | 56 | M | former | Lung Cancer | | | | SCC | | IV | 0 | 1 |
| SL-56 | 62 | M | former | Lung Cancer | | | | Adk | | IIA | 0 | 0 |
| SL-37 | 42 | F | na | Lung Cancer | | | | Other | | IV | 0 | 1 |
| SL-55 | 58 | M | smoker | Lung Cancer | | | | Adk | | IV | 1 | 0 |
| SL-69 | 72 | M | former | Lung Cancer | | bladder Cancer | | SCC | | | | |
| SL-109 | 64 | M | former | Lung Cancer | | | | SCC | | IV | 1 | 1a |
| SL-68 | 67 | M | na | Lung Cancer | | | | Adk | | IIA | 0 | 0 |
| SL-53 | 63 | M | former | Lung Cancer | | lung adk | | Adk | | IV | 1 | 1a |
| SL-101 | 49 | M | former | Lung Cancer | | | | Adk | | IA | 0 | 0 |
| SL-52 | 64 | F | smoker | Lung Cancer | | | | SCLC | 1 | IIIB | na | 0 |
| SL-39 | 71 | M | former | Lung Cancer | | | | SCLC | 1 | 0 | 0 | 0 |
| SL-88 | 54 | F | smoker | Lung Cancer | | | | Adk | | IV | 0 | 1 |
| SL-40 | 68 | M | former | Lung Cancer | | head & neck cancer | | Adk | | IB | 1 | 0 |
| SL-85 | 77 | M | former | Lung Cancer | | | | SCC | | IIB | 0 | 0 |

TABLE 16-continued

Clinical characteristics of patients in cohort

| ID | Age | Gender | Smoking Status | Group Status | SubGroup Status | Cancer history | Other Disease | Cancer type | SCLC | Cancer Stage | Relapse | Metastasis |
|---|---|---|---|---|---|---|---|---|---|---|---|---|
| SL-74 | 63 | M | smoker | Other cancer | Head and neck cancer + metastasis | | | | | | | |
| SL-38 | 73 | M | na | Other cancer | Colorectal Cancer + lung metastasis | colorectal adk | | | | | | |
| SL-155 | 49 | F | former | Other cancer | Thyroide Cancer | | asthma | | | | | |
| SL-83 | 66 | M | former | Validation | Lung Cancer | COPD | | Adk | 0 | IIIA | 0 | 0 |
| SL-158 | 55 | F | na | Validation | suspected neoplasia | | | Adk | | | | |
| SL-84 | 51 | F | smoker | Validation | Lung Cancer | COPD | aspergilosis | Adk | 0 | IIIA | | 0 |
| SL-117 | 70 | M | former | Validation | Lung Cancer | COPD | | SCC | 0 | IIB | 0 | 0 |
| SL-192_500 | 66 | F | former | Validation | suspected neoplasia | | | Adk | | | | |
| SL-35 | 60 | M | former | Validation | Lung Cancer | urothelial Cancer | | LCNC | | IV | 0 | 1 |
| SL-36 | 65 | M | smoker | Validation | Lung Cancer | COPD | | Other | 0 | IIIA | 0 | 0 |
| SL-48 | 63 | M | smoker | Validation | Lung Cancer | bladder Cancer | | SCC | | IIA | na | 0 |
| SL-187_500 | 39 | F | smoker | Validation | suspected neoplasia | | | | | | | |

For each individual in the cohort, 1 ml of serum was used to extract RNA for use in a TaqMan® quantitative RT-PCR assays (qRT-PCR; Applied Biosystems; used for miR-720 and miR-451), or qRT-PCR using Exiqon custom LNA primers (Exiqon, Vedbaek, DK; used for small U2 and 13750). RNA was isolated as described in Example 3.

TaqMan® quantitative RT-PCR assays or qRT-PCR using Exiqon primers were used to measure small RNA levels in the total RNA samples isolated from the serum of the individuals in the cohort. The small RNA levels detected were small U2, miR-720, miR-451, 13750, and CelmiR-39 (C. elegans miR-39). CelmiR-39 was added as a spike-in control to correct for variations in RNA purification from serum. The average Ct from three reactions is shown in Table 17 for each individual in the cohort.

TABLE 17

Average Ct for small U2, miR-720, miR-451, 13750, and CelmiR-39 spike-in control

| ID | Group Status | small U2 | miR-720 | miR-451 | 13750 | Spike-CelmiR-39 |
|---|---|---|---|---|---|---|
| SA-112 bis | Control | 22.62 | 25.06 | 20.56 | 30.97 | 17.66 |
| SA-103a | Control | 25.38 | 26.28 | 25.06 | 31.83 | 18.58 |
| SA-104 | Control | 24.94 | 25.74 | 23.69 | 28.25 | 18.58 |
| SA-105 | Control | 24.19 | 24.87 | 24.36 | 30.06 | 19.49 |
| SA-106 | Control | 20.94 | 23.66 | 23.33 | 29.92 | 18.93 |
| SA-107 | Control | 23.28 | 25.24 | 22.63 | 31.03 | 19.00 |
| SA-108 bis | Control | 22.34 | 25.51 | 21.22 | 28.67 | 17.78 |
| SA-109 | Control | 22.61 | 25.36 | 20.92 | 27.21 | 18.11 |
| SA-110 | Control | 24.09 | 25.82 | 21.97 | 31.07 | 18.54 |
| SA-111 | Control | 22.96 | 25.05 | 22.26 | 29.05 | 18.48 |
| SA-113 | Control | 23.61 | 25.45 | 21.86 | 31.94 | 18.77 |
| SA-114 | Control | 23.36 | 24.65 | 20.96 | 32.73 | 18.27 |
| SA-115 | Control | 23.82 | 25.80 | 21.06 | 32.55 | 18.76 |
| SA-116 | Control | 22.92 | 25.77 | 21.85 | 31.35 | 18.49 |
| SA-117 | Control | 22.79 | 25.68 | 20.42 | 31.72 | 17.80 |
| SA-118 | Control | 22.81 | 25.29 | 19.89 | 31.33 | 18.16 |
| SA-119 | Control | 20.87 | 24.09 | 19.35 | 31.53 | 17.02 |
| SA-120 | Control | 22.80 | 25.47 | 20.63 | 31.45 | 17.61 |
| SA-121 | Control | 22.69 | 24.66 | 21.00 | 32.25 | 19.35 |
| SA-122 | Control | 23.12 | 26.66 | 22.05 | 32.03 | 19.33 |
| SA-123 | Control | 21.81 | 25.23 | 19.90 | 32.6 | 17.44 |
| SA-124 | Control | 22.21 | 25.24 | 20.55 | 32.66 | 18.47 |
| SA-125 | Control | 22.86 | 24.82 | 19.12 | 31.44 | 18.42 |
| SA-126 | Control | 21.72 | 24.88 | 19.88 | 31.78 | 18.37 |
| SA-127 | Control | 24.06 | 25.37 | 19.94 | 32.63 | 17.64 |
| SA-128 | Control | 24.02 | 25.36 | 18.88 | 30.95 | 15.87 |
| SA-129 | Control | 24.14 | 25.56 | 25.75 | 33.14 | 15.83 |
| SA-130 | Control | 22.11 | 24.62 | 18.88 | 31.3 | 15.14 |
| SA-131 | Control | 22.21 | 25.28 | 20.26 | 32.44 | 15.40 |
| SA-132 | Control | 24.10 | 26.02 | 24.49 | 34.84 | 15.31 |
| SA-133 | Control | 23.68 | 24.82 | 21.30 | 31.16 | 18.21 |
| SA-134 | Control | 24.03 | 25.18 | 20.80 | 30.53 | 16.91 |
| SA-135 | Control | 25.53 | 24.42 | 20.46 | 32.73 | 18.45 |
| SA-136 | Control | 22.98 | 24.76 | 21.07 | 31.67 | 17.09 |
| SA-137 | Control | 22.39 | 24.60 | 19.57 | 31.98 | 17.17 |
| SA-138 | Control | 22.35 | 24.78 | 19.76 | 30.66 | 17.96 |
| SA-CTL-126 | Control | 23.18 | 26.88 | 23.38 | 30.89 | 17.45 |
| SA-CTL-127 | Control | 24.71 | 26.84 | 21.99 | 29.90 | 17.57 |
| SA-CTL-128 | Control | 21.77 | 26.47 | 23.14 | 29.71 | 17.66 |
| SA-CTL-129 | Control | 23.09 | 25.45 | 20.37 | 28.39 | 16.59 |
| SA-CTL-130 | Control | 21.98 | 26.10 | 21.97 | 29.08 | 17.15 |
| SA-CTL-131 | Control | 24.27 | 26.92 | 22.48 | 30.20 | 18.07 |
| SA-CTL-132 | Control | 23.35 | 27.34 | 22.70 | 29.62 | 17.98 |
| SA-CTL-133 | Control | 22.83 | 26.71 | 23.14 | 31.96 | 17.19 |
| SA-CTL-578 | Control | 24.11 | 26.74 | 22.77 | 33.16 | 16.58 |
| SL-04 | Control MD | 22.23 | 24.39 | 22.84 | 28.53 | 17.90 |
| SL-159 | Control MD | 22.10 | 23.48 | 15.33 | 28.05 | 16.42 |
| SL-190_500 | Control MD | 20.75 | 24.21 | | 28.84 | 16.17 |

TABLE 17-continued

Average Ct for small U2, miR-720, miR-451, 13750, and CelmiR-39 spike-in control

| ID | Group Status | small U2 | miR-720 | miR-451 | 13750 | Spike-CelmiR-39 |
|---|---|---|---|---|---|---|
| SL-163 | Control MD | 20.80 | 23.06 | 19.19 | 29.87 | 16.86 |
| SL-99 | Control MD | 22.26 | 23.67 | 19.68 | 27.52 | 17.04 |
| SL-161 | Control MD | 23.16 | 23.41 | 18.88 | 30.46 | 16.62 |
| SL-188_500 | Control MD | 21.57 | 25.03 | 16.75 | 29 | 16.46 |
| SL-164 | Control MD | 21.71 | 23.19 | 18.56 | 30.59 | 16.65 |
| SL-167 | Control MD | 20.90 | 22.69 | 17.91 | 29.66 | 17.19 |
| SL-165 | Control MD | 21.69 | 23.37 | 17.43 | 30.35 | 15.99 |
| SL-93 | Control MD | 23.00 | 25.97 | 21.50 | 29.67 | 16.97 |
| SL-160 | Control MD | 22.12 | 23.54 | 18.01 | 30.99 | 16.55 |
| SL-92 | Control MD | 23.16 | 25.22 | 20.77 | 28.01 | 17.31 |
| SL-162 | Control MD | 21.74 | 23.46 | 18.07 | 30.76 | 16.06 |
| SL-166 | Control MD | 22.49 | 23.82 | 16.71 | 30.56 | 15.88 |
| SL-46 | Lung Ca | 21.09 | 26.55 | 22.38 | 32.73 | 16.91 |
| SL-47 | Lung Ca | 21.05 | 27.11 | 22.37 | 32.07 | 17.04 |
| SL-57 | Lung Ca | 21.51 | 25.10 | 21.09 | 29.73 | 15.97 |
| SL-80 | Lung Ca | 21.97 | 26.65 | 21.15 | 30.42 | 17.76 |
| SL-106 | Lung Ca | 22.87 | 24.78 | 20.03 | 31.79 | 19.13 |
| SL-105 | Lung Ca | 19.62 | 23.06 | 17.95 | 29.48 | 17.93 |
| SL-71 | Lung Ca | 20.90 | 27.12 | 22.31 | 32.8 | 17.95 |
| SL-67 | Lung Ca | 19.42 | 25.48 | 21.20 | 30.94 | 17.46 |
| SL-58 | Lung Ca | 21.24 | 26.41 | 21.58 | 31.58 | 15.73 |
| SL-54 | Lung Ca | 19.37 | 26.84 | 21.89 | 29.87 | 17.89 |
| SL-41 | Lung Ca | 22.69 | 26.92 | 23.26 |  | 17.79 |
| SL-108 | Lung Ca | 17.96 | 22.18 | 18.55 | 29.8 | 17.38 |
| SL-61 | Lung Ca | 20.91 | 27.01 | 20.13 | 30.26 | 16.21 |
| SL-66 | Lung Ca | 19.11 | 25.25 | 20.21 | 29.99 | 16.47 |
| SL-63 | Lung Ca | 21.31 | 26.54 | 22.47 | 32.17 | 16.86 |
| SL-60 | Lung Ca | 20.84 | 26.14 | 21.18 | 30.15 | 16.44 |
| SL-89 | Lung Ca | 20.77 | 23.56 | 20.51 | 31.86 | 18.93 |
| SL-43 | Lung Ca | 20.28 | 26.61 | 22.00 | 32.34 | 16.79 |
| SL-62 | Lung Ca | 23.07 | 28.25 | 22.61 | 30.93 | 18.20 |
| SL-44 | Lung Ca | 20.18 | 27.37 | 22.50 | 30.26 | 17.82 |
| SL-70 | Lung Ca | 20.33 | 26.21 | 19.22 | 29.56 | 16.84 |
| SL-90 | Lung Ca | 20.53 | 23.08 | 19.28 | 30.51 | 17.76 |
| SL-96 | Lung Ca | 21.50 | 23.32 | 21.47 | 30.33 | 18.48 |
| SL-64 | Lung Ca | 20.64 | 24.74 | 21.39 | 30.76 | 16.75 |
| SL-50 | Lung Ca | 22.07 | 26.89 | 22.57 | 31.22 | 18.01 |
| SL-59 | Lung Ca | 19.31 | 26.01 | 21.67 | 30.59 | 15.36 |
| SL-51 | Lung Ca | 21.81 | 28.01 | 22.73 | 30.10 | 18.12 |
| SL-78 | Lung Ca | 20.93 | 27.00 | 21.98 | 30.98 | 16.70 |
| SL-34 | Lung Ca | 20.25 | 26.80 | 22.16 |  | 16.93 |
| SL-87 | Lung Ca | 19.80 | 23.86 | 17.90 | 31.12 | 17.06 |
| SL-77 | Lung Ca | 19.50 | 24.67 | 22.78 | 32.42 | 17.21 |
| SL-73 | Lung Ca | 20.50 | 26.57 | 24.03 | 34.69 | 17.54 |
| SL-56 | Lung Ca | 21.66 | 27.58 | 21.11 | 32.16 | 15.35 |
| SL-37 | Lung Ca | 21.05 | 26.19 | 22.41 |  | 17.15 |
| SL-55 | Lung Ca | 18.55 | 25.69 | 18.63 | 30.44 | 15.62 |
| SL-69 | Lung Ca | 22.26 | 25.84 | 22.23 | 32.45 | 18.84 |
| SL-109 | Lung Ca | 19.88 | 23.74 | 20.68 | 31.85 | 17.06 |
| SL-68 | Lung Ca | 22.21 | 27.03 | 22.64 | 31.54 | 17.64 |
| SL-53 | Lung Ca | 20.02 | 26.66 | 20.10 | 30.81 | 17.01 |
| SL-101 | Lung Ca | 20.80 | 23.06 | 18.86 | 30.1 | 18.01 |
| SL-52 | Lung Ca | 19.99 | 25.95 | 22.34 | 30.07 | 16.85 |
| SL-39 | Lung Ca | 22.93 | 27.88 | 23.72 |  | 17.35 |
| SL-88 | Lung Ca | 20.77 | 23.64 | 20.65 | 32.05 | 19.09 |
| SL-40 | Lung Ca | 22.85 | 27.74 | 22.36 | 29.91 | 17.28 |
| SL-85 | Lung Ca | 22.64 | 24.98 | 22.23 | 32.41 | 18.34 |
| SL-03 | COPD + lung Ca | 21.01 | 23.51 | 24.06 | 30.66 | 17.74 |
| SL-79 | COPD + lung Ca | 21.85 | 26.06 | 22.06 | 31.82 | 17.04 |
| SL-115 | COPD + lung Ca | 19.14 | 23.31 | 20.84 | 31.07 | 15.94 |
| SL-140_500 | COPD + lung Ca | 20.16 | 22.80 | 21.68 | 30.45 | 16.16 |
| SL-81 | COPD + lung Ca | 20.87 | 25.01 | 22.00 | 30.63 | 17.75 |
| SL-110 | COPD + lung Ca | 20.00 | 24.99 | 23.23 | 31.87 | 16.82 |
| SL-42 | COPD + lung Ca | 20.96 | 27.48 | 22.17 | 30.8 | 16.78 |
| SL-08 | COPD + lung Ca | 22.18 | 24.80 | 20.70 | 30.21 | 19.53 |
| SL-91 | COPD + lung Ca | 21.06 | 25.52 | 20.14 | 29.99 | 17.01 |
| SL-45 | COPD + lung Ca | 22.95 | 28.73 | 23.11 | 31.85 | 17.77 |
| SL-100 | COPD + lung Ca | 21.27 | 25.94 | 22.34 | 31.06 | 17.14 |
| SL-107 | COPD + lung Ca | 20.73 | 23.82 | 20.52 | 31.76 | 17.11 |
| SL-65 | COPD + lung Ca | 21.24 | 26.70 | 21.34 | 28.57 | 17.72 |
| SL-72 | COPD + lung Ca | 22.20 | 27.54 | 23.70 | 31.82 | 18.54 |
| SL-49 | COPD + lung Ca | 22.17 | 26.84 | 24.33 | 33.57 | 18.05 |
| SL-75 | COPD + lung Ca | 20.89 | 26.58 | 21.50 | 33.01 | 16.98 |
| SL-156 | fibrosis | 21.38 | 24.32 | 16.80 | 30.1 | 16.90 |
| SL-130 | fibrosis | 21.39 | 24.49 | 17.70 | 31.54 | 16.56 |
| SL-157 | fibrosis | 19.74 | 22.61 | 15.24 | 30.26 | 15.59 |
| SL-137 | fibrosis | 20.28 | 22.39 | 17.71 | 32.8 | 15.18 |
| SL-171_500 | fibrosis | 22.47 | 24.41 | 21.35 | 31.58 | 15.85 |
| SA-95 | COPD – lung Ca | 22.73 | 25.98 | 23.62 | 29.08 | 18.09 |
| SA-96a | COPD – lung Ca | 22.56 | 25.47 | 23.74 | 29.36 | 18.40 |
| SA-97 | COPD – lung Ca | 21.60 | 24.35 | 23.14 | 28.83 | 17.44 |
| SA-98a | COPD – lung Ca | 24.04 | 25.89 | 26.26 | 30.24 | 17.84 |
| SL-152 | COPD – lung Ca | 24.36 | 25.59 | 19.82 | 31.28 | 18.23 |
| SL-149 | COPD – lung Ca | 22.38 | 24.62 | 20.35 | 28.67 | 18.01 |
| SL-146 | COPD – lung Ca | 23.66 | 25.41 | 22.04 | 29.46 | 18.65 |
| SL-153 | COPD – lung Ca | 23.53 | 25.71 | 22.88 |  | 18.28 |
| SL-169_500 | COPD – lung Ca | 21.84 | 25.49 | 21.21 | 29.56 | 18.00 |
| SL-154 | COPD – lung Ca | 22.06 | 24.90 | 19.35 | 31.62 | 18.68 |
| SL-143 | COPD – lung Ca | 23.11 | 25.42 | 24.39 | 30.82 | 18.37 |
| SL-150 | COPD – lung Ca | 22.13 | 25.17 | 18.45 | 28.18 | 17.60 |
| SL-141 | COPD – lung Ca | 24.73 | 24.76 | 23.75 | 28.95 | 18.58 |
| SL-142 | COPD – lung Ca | 24.88 | 29.72 | 25.50 |  | 17.65 |
| SL-06 | COPD – lung Ca | 24.98 | 25.99 | 24.47 | 31.03 | 19.12 |
| SL-170_500 | COPD – lung Ca | 20.58 | 23.76 | 22.42 | 30.55 | 18.63 |
| SL-172_500 | COPD – lung Ca | 21.76 | 24.48 | 16.67 | 28.56 | 16.07 |
| SL-134 | COPD – lung Ca | 22.87 | 24.76 | 22.96 | 29.28 | 19.72 |
| SL-151 | COPD – lung Ca | 23.05 | 25.47 | 21.25 | 29.53 | 17.66 |
| SL-98 | COPD – lung Ca | 21.92 | 24.53 | 21.75 | 28.88 | 16.71 |
| SL-176_500 | COPD – lung Ca | 21.72 | 25.71 | 17.07 | 30.2 | 16.95 |
| SL-127 | COPD – lung Ca | 22.53 | 24.78 | 22.84 | 28.70 | 19.72 |
| SL-104 | Control SI | 21.69 | 24.41 | 21.10 | 28.28 | 17.80 |
| SL-18 | Control SI | 22.33 | 24.05 | 21.83 | 28.16 | 17.96 |
| SL-97 | Control SI | 24.36 | 27.39 | 22.56 | 29.30 | 18.67 |
| SL-30 | Control SI | 22.30 | 24.97 | 23.17 | 29.61 | 18.54 |
| SL-82 | Control SI | 23.19 | 26.29 | 19.85 | 28.40 | 16.38 |
| SL-29 | Control SI | 22.98 | 24.68 | 22.41 | 30.92 | 17.71 |
| SL-124 | Control SI | 21.49 | 23.53 | 20.09 | 29.62 | 17.36 |
| SL-05 | Control SI | 22.44 | 25.00 | 21.98 | 28.11 | 17.39 |
| SL-138 | Control SI | 22.30 | 24.59 | 17.27 | 30.73 | 16.86 |
| SL-14 | Control SI | 23.45 | 23.87 | 21.02 | 27.99 | 17.98 |
| SL-94 | Control SI | 24.50 | 26.37 | 20.62 | 31.00 | 17.05 |
| SL-139 | Control SI | 20.42 | 24.42 | 16.45 | 30.15 | 16.02 |
| SL-111 | Control SI | 22.23 | 23.81 | 19.61 | 27.67 | 16.97 |
| SL-95 | Control SI | 23.44 | 26.09 | 20.36 | 29.69 | 17.15 |
| SL-74 | Other ca | 21.91 | 26.67 | 23.63 | 34.37 | 18.14 |
| SL-38 | Other ca | 23.50 | 26.89 | 24.56 | 33.53 | 18.03 |
| SL-155 | Other ca | 20.37 | 23.83 | 19.60 | 31.94 | 18.20 |

In this experiment, with a much larger cohort, it was confirmed that small U2 is present at elevated levels in serum from lung cancer patients, while miR-720, miR-451, and 13750 are present at reduced levels in serum from lung cancer patients.

Figure 18:
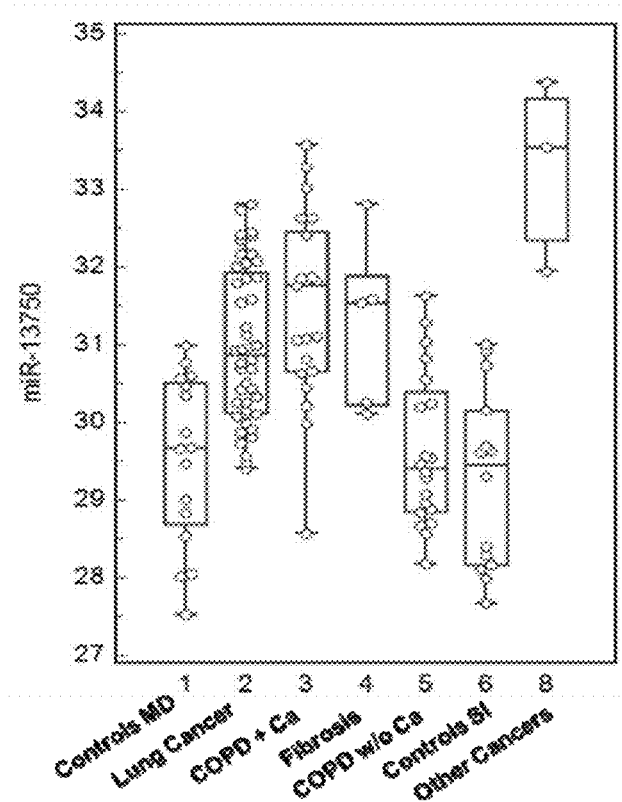
FIG. 18 shows a plot of the average Ct values for 13750 in serum from various individuals in a larger cohort, as described in Example 9.

FIG. 18 shows a plot of the Ct values for 13750. In this experiment, 13750 distinguished between lung cancer and the controls, including COPD, with a p value of <0.001.

An analysis of variance (ANOVA) was carried out on the four markers tested in Table 17 to determine each marker's ability to distinguish lung cancer from non-lung cancer. The results of the ANOVA are shown in Table 18.

TABLE 18

ANOVA results for small U2, miR-720, miR-451, and 13750

| RNA | Sq F value | Pr (>F) |
|---|---|---|
| Small U2 | 137.6 | <2.2e-16 |
| miR-720 | 45.8 | 6.4e-10 |
| miR-451 | 4.6 | 0.035 |
| 13750 | 31.1 | 1.72e-7 |

Small U2, miR-720, and 13750 are each able to distinguish between lung cancer and non-lung cancer with p values of <0.001. MiR-451 is able to distinguish between lung cancer and non-lung cancer with a p value of <0.05.

The Linear Discriminant Analysis (LDA) approach was used to maximize the ratio of the between-class variance to the within-class variance in the data, in order to maximize separability of lung cancer from non-lung cancer. See, e.g., Nikas et al. Cancer Inform. 11: 1-14 (2012); R Development Core Team (2011); R: A language and environment for statistical computing. R Foundation for Statistical Computing, Vienna, Austria. ISBN 3-900051-07-0. Using this approach, the coefficient of linear discriminant was determined for each RNA, and is shown in Table 19:

TABLE 19

Coefficients of linear discriminants

| RNA | Coefficient |
|---|---|
| Small U2 | 1.0712027 |
| miR-720 | −0.4534064 |
| miR-451 | −0.1715311 |
| 13750 | −0.2694863 |

The coefficients were then applied to the Cts for each microRNA for each patient using the formula: (Ct small U2×1.0712027)−(Ct 13750×0.2694863)−(miR-720×0.4534064)−(miR-451×0.1715311). This formula was referred to as "Canon LDA-1."

Figure 19:
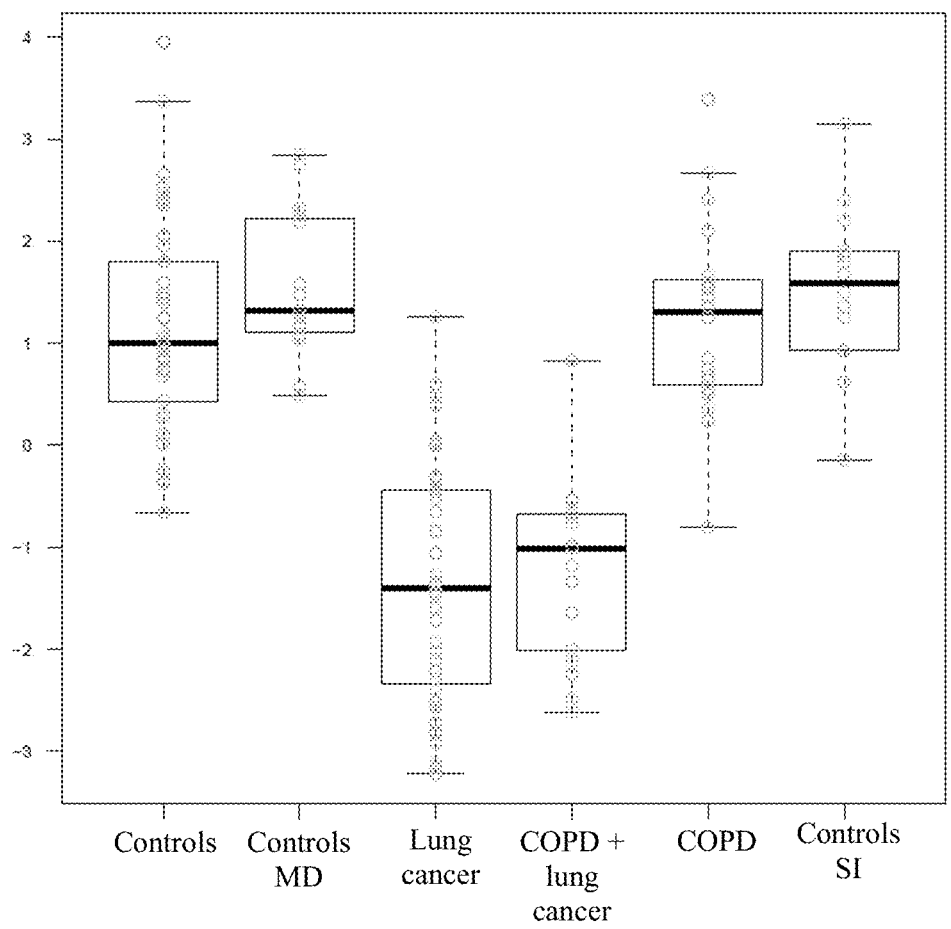
FIG. 19 shows a plot of the results of the Canon LDA-1 formula calculated using the Cts for small U2, miR-451, miR-720, and 13750 in serum from various individuals in a larger cohort, as described in Example 9.

Canon LDA-1, which uses a combination of the four RNAs, was then tested for the ability to distinguish lung cancer from other conditions. The fibrosis samples were omitted from this analysis. The results are shown in FIG. 19. The combination of small U2, miR-720, miR-451, and 13750 is able to distinguish patients with lung cancer from patients having other conditions.

Because many lung cancer patients also suffer from COPD, the ability of each of small U2, miR-451, miR-720, and 13750 to distinguish between COPD without cancer and COPD with cancer was determined Table 20 shows the ANOVA results for the four RNAs.

TABLE 20

ANOVA results for small U2, miR-720, miR-451, and 13750

| RNA | Sq F value | Pr (>F) |
|---|---|---|
| Small U2 | 47.2 | 2.0e-6 |
| miR-720 | 1.9 | 0.18 |
| miR-451 | 0.07 | 0.79 |
| 13750 | 24.7 | 9.8e-5 |

Small U2 and 13750 are able to distinguish between COPD without lung cancer and COPD with lung cancer, with p values of <0.001.

Again, the LDA approach was used to maximize the ratio of the between-class variance to the within-class variance in the data, in order to maximize separability of COPD with cancer from COPD without cancer. Using this approach, the coefficients of linear discriminant was determined for small U2 and 13750, and are shown in Table 21:

TABLE 21

Coefficients of linear discriminants

| RNA | Coefficient |
|---|---|
| Small U2 | −0.7535686 |
| 13750 | 0.7190100 |

5.10 Example 10

Validation of Canon LDA-1

Samples from the nine "validation" patients shown in Table 16 were tested using the four RNA combination (Canon LDA-1) to determine the ability of the combination to detect lung cancer at an early stage, prior to diagnosis by other methods. Table 22 shows the nine patients in the validation cohort, and the number of months prior to diagnosis that the serum was collected. In the last three patients, the samples were analyzed prior to diagnosis, so the unbiased predictive value of the combination was determined.

TABLE 22

Validation cohort

| ID | Annotation | Serum drawn x months before diagnosis | Diagnosis |
|---|---|---|---|
| S10-551 | COPD + Ca | −1 | Lung Cancer |
| S10-826-d | Bladder Ca + Lung Ca | −0.5 | Lung Cancer |
| S10-518 | Lung Ca | −8 | Lung Cancer |
| S10-1058 | COPD + Ca | −1 | Lung Cancer |
| S10-1861 | COPD + Ca | −1 | Lung Cancer |
| S10-1963 | COPD + Ca | −0.5 | Lung Cancer |
| S10-1353 | Suspected Ca | −2 | Lung Cancer |
| S10-971 | Suspected Ca | −2.5 | NO Lung Cancer |
| S10-31 | Suspected Ca | −2.5 | Lung Cancer |

Figure 20:
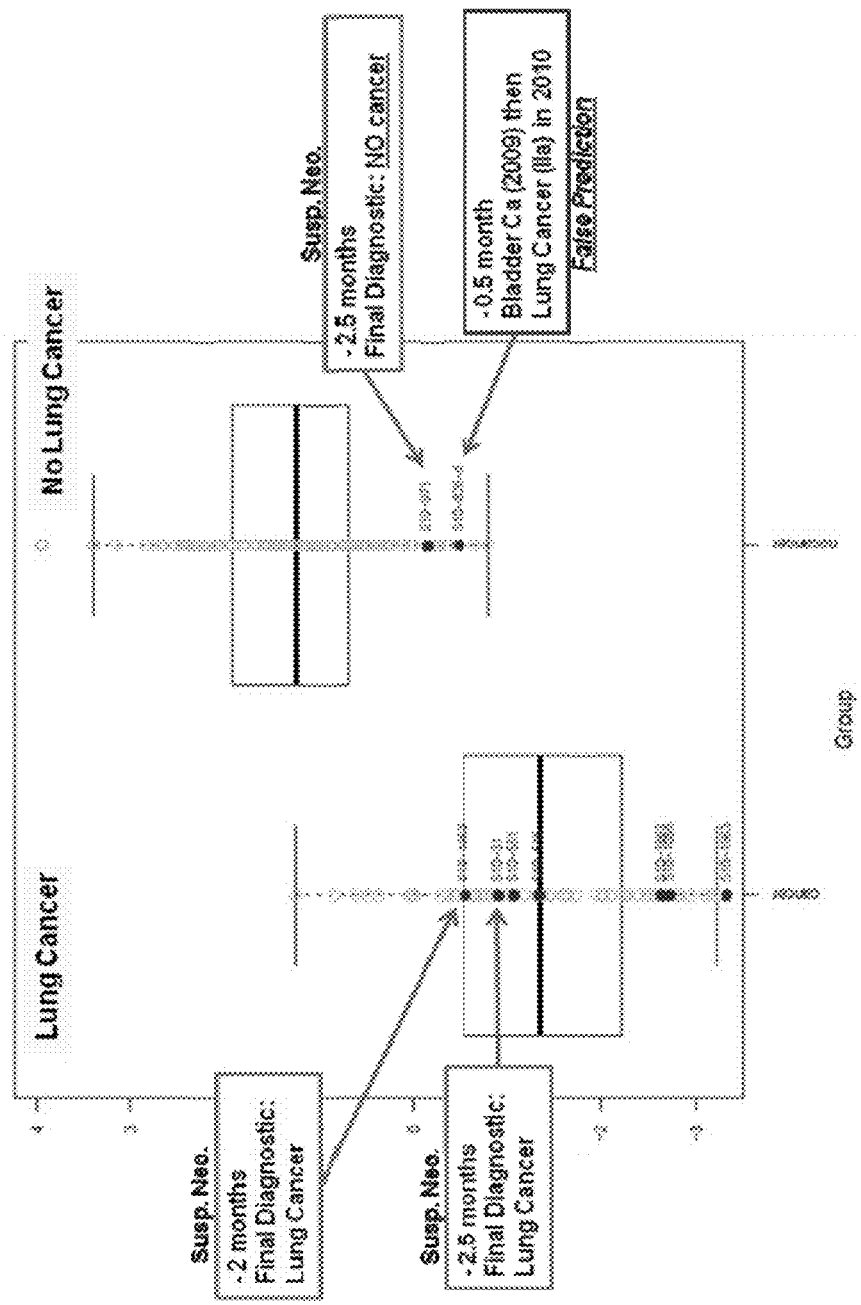
FIG. 20 shows a plot of the predicted lung cancer status, determined using the combination of small U2, miR-720, miR-451, and 13750, and serum from nine "validation" individuals in the cohort, as described in Example 10.
Figure 21:
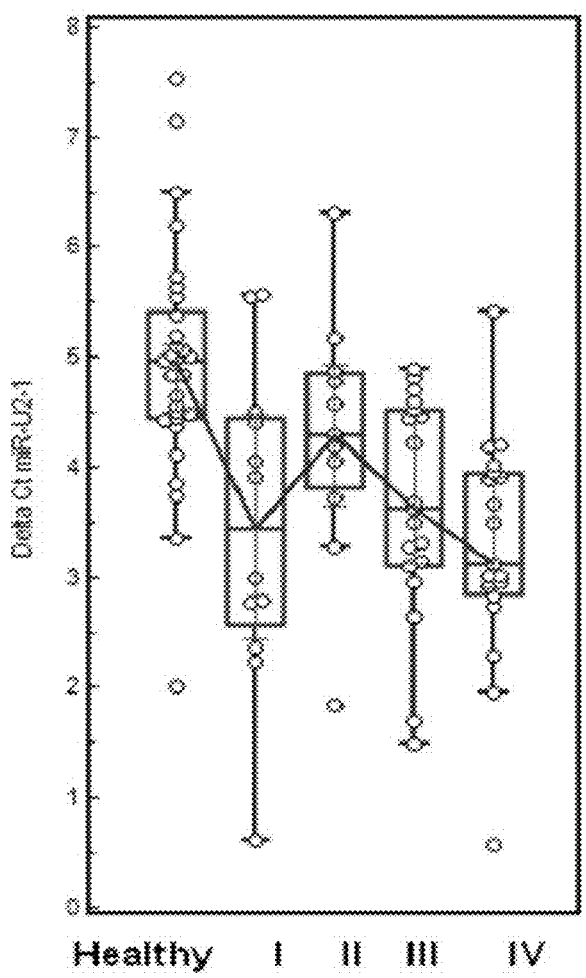
FIG. 21 shows a plot of the deltaCt values for small U2 according to lung cancer stage, as described in Example 11.

The combination of small U2, miR-720, miR-451, and 13750 was used to predict the lung cancer status of each of the patients in the validation cohort. As shown in FIG. 20, the lung cancer status of eight out of nine patients in the validation cohort was correctly predicted. The only incorrect result was returned for patient S10-826-d, who was ultimately diagnosed with lung cancer, which was probably due to metastasis of a preexisting bladder cancer. Further, patient S10-971, who was identified by clinicians as having a suspected neoplasia, was determined in the assay to not have lung cancer. This patient was ultimately diagnosed as not having lung cancer.

These results demonstrate that the Canon LDA-1 (small U2, miR-720, miR-451, and 13750) was able to predict the presence of lung cancer (or its absence) several months before a clinician was able to do so with currently available technology.

5.11 Example 11

Small U2 is Highly Expressed in Early Stage Lung Cancer

The data for small U2 shown in Table 17 was plotted according to lung cancer stage. The results are shown in FIG.

21. Small U2 is highly expressed in stage I lung cancer. Thus, at least small U2 may be a particularly good marker for detecting early stage lung cancer. This result is consistent with the validation results discussed above in Example 10 and shown in FIG. 20.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that changes can be made without departing from the spirit and scope of the invention(s).

What is claimed is:

1. A composition comprising: (i) a first polynucleotide comprising a sequence that is fully identical or fully complementary to the sequence of SEQ ID NO: 2, and (ii) a second polynucleotide comprising a sequence that is fully identical or fully complementary to the sequence of SEQ ID NO: 23; wherein the first and second polynucleotides are each between 18 and 100 nucleotides long, and wherein the first and second polynucleotides each comprise at least one detectable moiety selected from fluorophore, electron spin label, biotin, horseradish peroxidase, and radiolabel and/or wherein the first and second polynucleotides each comprise an affinity-enhancing nucleotide analog.

2. The composition of claim 1, wherein the first and second polynucleotides each comprise at least one detectable moiety, which is a fluorescent dye.

3. The composition of claim 2, wherein the first and second polynucleotides are fluorescence resonance energy transfer (FRET) probes comprising a fluorescent dye and a quencher molecule.

4. The composition of claim 1, wherein the first and second polynucleotides further comprise a region comprising a sequence that is not identical or complementary to a region of SEQ ID NO: 1 or 22.

5. The composition of claim 1, wherein the composition does not comprise a microarray.

6. The composition of claim 5, wherein each polynucleotide comprises a region comprising a sequence that is not identical or complementary to a region of a target RNA selected from SEQ ID NOS: 1, 22, 25, 32, and 36.

7. The composition of claim 1, wherein the composition comprises RNAs of a sample from a subject or cDNAs reverse transcribed from RNAs of a sample from a subject.

8. A kit comprising the composition of claim 1.

9. The kit of claim 8, wherein the kit further comprises at least one polymerase.

10. The kit of claim 8, wherein the kit further comprises dNTPs.

* * * * *

SEQUENCE LISTING

```
<160> NUMBER OF SEQ ID NOS: 82

<210> SEQ ID NO 1
<211> LENGTH: 188
<212> TYPE: RNA
<213> ORGANISM: Homo sapiens

<400> SEQUENCE: 1
aucgcuucuc ggccuuuugg cuaagaucaa guguaguauc uguucuuauc aguuuaauau      60
cugauacguc cucuauccga ggacaauaua uuaaauggau uuuuggagca gggagaugga     120
auaggagcuu gcuccgucca cuccacgcau cgaccuggua uugcaguacc uccaggaacg     180
gugcaccc                                                             188

<210> SEQ ID NO 2
<211> LENGTH: 18
<212> TYPE: RNA
<213> ORGANISM: Homo sapiens

<400> SEQUENCE: 2
uggauuuuug gagcaggg                                                   18

<210> SEQ ID NO 3
<211> LENGTH: 30
<212> TYPE: RNA
<213> ORGANISM: Homo sapiens

<400> SEQUENCE: 3
aaauggauuu uuggagcagg gagauggaau                                      30

<210> SEQ ID NO 4
<211> LENGTH: 25
<212> TYPE: RNA
<213> ORGANISM: Homo sapiens

<400> SEQUENCE: 4
aaauggauuu uuggagcagg gagau                                           25

<210> SEQ ID NO 5
<211> LENGTH: 24
<212> TYPE: RNA
<213> ORGANISM: Homo sapiens

<400> SEQUENCE: 5
aaauggauuu uuggagcagg gaga                                            24

<210> SEQ ID NO 6
<211> LENGTH: 23
<212> TYPE: RNA
<213> ORGANISM: Homo sapiens

<400> SEQUENCE: 6
aaauggauuu uuggagcagg gag                                             23
```

```
<210> SEQ ID NO 7
<211> LENGTH: 22
<212> TYPE: RNA
<213> ORGANISM: Homo sapiens

<400> SEQUENCE: 7 aaauggauuuu uuggagcagg ga                                              22

<210> SEQ ID NO 8
<211> LENGTH: 21
<212> TYPE: RNA
<213> ORGANISM: Homo sapiens

<400> SEQUENCE: 8 aaauggauuuu uuggagcagg g                                               21

<210> SEQ ID NO 9
<211> LENGTH: 24
<212> TYPE: RNA
<213> ORGANISM: Homo sapiens

<400> SEQUENCE: 9 aauggauuuuu uggagcaggg agau                                            24

<210> SEQ ID NO 10
<211> LENGTH: 23
<212> TYPE: RNA
<213> ORGANISM: Homo sapiens

<400> SEQUENCE: 10 aauggauuuuu uggagcaggg aga                                             23

<210> SEQ ID NO 11
<211> LENGTH: 22
<212> TYPE: RNA
<213> ORGANISM: Homo sapiens

<400> SEQUENCE: 11 aauggauuuuu uggagcaggg ag                                              22

<210> SEQ ID NO 12
<211> LENGTH: 21
<212> TYPE: RNA
<213> ORGANISM: Homo sapiens

<400> SEQUENCE: 12 aauggauuuuu uggagcaggg a                                               21

<210> SEQ ID NO 13
<211> LENGTH: 23
<212> TYPE: RNA
<213> ORGANISM: Homo sapiens

<400> SEQUENCE: 13
auggauuuuu ggagcaggga gau                                              23

<210> SEQ ID NO 14
<211> LENGTH: 22
<212> TYPE: RNA
<213> ORGANISM: Homo sapiens

<400> SEQUENCE: 14
auggauuuuu ggagcaggga ga                                               22
```

```
<210> SEQ ID NO 15
<211> LENGTH: 21
<212> TYPE: RNA
<213> ORGANISM: Homo sapiens

<400> SEQUENCE: 15
auggauuuuu ggagcaggga g                                             21

<210> SEQ ID NO 16
<211> LENGTH: 20
<212> TYPE: RNA
<213> ORGANISM: Homo sapiens

<400> SEQUENCE: 16
auggauuuuu ggagcaggga                                               20

<210> SEQ ID NO 17
<211> LENGTH: 19
<212> TYPE: RNA
<213> ORGANISM: Homo sapiens

<400> SEQUENCE: 17
auggauuuuu ggagcaggg                                                19

<210> SEQ ID NO 18
<211> LENGTH: 21
<212> TYPE: RNA
<213> ORGANISM: Homo sapiens

<400> SEQUENCE: 18
uggauuuuug gagcagggag a                                             21

<210> SEQ ID NO 19
<211> LENGTH: 20
<212> TYPE: RNA
<213> ORGANISM: Homo sapiens

<400> SEQUENCE: 19
uggauuuuug gagcagggag                                               20

<210> SEQ ID NO 20
<211> LENGTH: 19
<212> TYPE: RNA
<213> ORGANISM: Homo sapiens

<400> SEQUENCE: 20
uggauuuuug gagcaggga                                                19

<210> SEQ ID NO 21
<211> LENGTH: 17
<212> TYPE: RNA
<213> ORGANISM: Homo sapiens

<400> SEQUENCE: 21
ucucgcuggg gccucca                                                  17

<210> SEQ ID NO 22
<211> LENGTH: 110
<212> TYPE: RNA
<213> ORGANISM: Homo sapiens

<400> SEQUENCE: 22
```

```
ccggaucuca cacgguggug uuaauaucuc gcuggggccu ccaaaauguu gugcccaggg     60
guguuagaga aaacaccaca cuugagaug aauuaagagu ccuuuauuag                110
```

<210> SEQ ID NO 23
<211> LENGTH: 18
<212> TYPE: RNA
<213> ORGANISM: Homo sapiens

<400> SEQUENCE: 23

```
aucucgcugg ggccucca                                                   18
```

<210> SEQ ID NO 24
<211> LENGTH: 22
<212> TYPE: RNA
<213> ORGANISM: Homo sapiens

<400> SEQUENCE: 24

```
aaaccguuac cauuacugag uu                                              22
```

<210> SEQ ID NO 25
<211> LENGTH: 72
<212> TYPE: RNA
<213> ORGANISM: Homo sapiens

<400> SEQUENCE: 25

```
cuugggaaug gcaaggaaac cguuaccauu acugaguuua guaaugguaa ugguucucuu     60
gcuauaccca ga                                                         72
```

<210> SEQ ID NO 26
<211> LENGTH: 20
<212> TYPE: RNA
<213> ORGANISM: Homo sapiens

<400> SEQUENCE: 26

```
uaaugguaau gguucucuug                                                 20
```

<210> SEQ ID NO 27
<211> LENGTH: 21
<212> TYPE: RNA
<213> ORGANISM: Homo sapiens

<400> SEQUENCE: 27

```
uuuaguaaug guaaugguuc u                                               21
```

<210> SEQ ID NO 28
<211> LENGTH: 23
<212> TYPE: RNA
<213> ORGANISM: Homo sapiens

<400> SEQUENCE: 28

```
aaaccguuac cauuacugag uuu                                             23
```

<210> SEQ ID NO 29
<211> LENGTH: 21
<212> TYPE: RNA
<213> ORGANISM: Homo sapiens

<400> SEQUENCE: 29

```
aaaccguuac cauuacugag u                                               21
```

<210> SEQ ID NO 30
<211> LENGTH: 20

```
<212> TYPE: RNA
<213> ORGANISM: Homo sapiens

<400> SEQUENCE: 30
aaaccguuac cauuacugag                                               20

<210> SEQ ID NO 31
<211> LENGTH: 22
<212> TYPE: RNA
<213> ORGANISM: Homo sapiens

<400> SEQUENCE: 31
ugucuuuccu uguuggagca gg                                            22

<210> SEQ ID NO 32
<211> LENGTH: 120
<212> TYPE: RNA
<213> ORGANISM: Homo sapiens

<400> SEQUENCE: 32 gcccccaaa augcuucugu accccugccc caacaaggaa ggacaagagg ugugagccac     60
acacacgccu ggccuccugu cuuuccuugu uggagcaggg auguagaagc acuugccgca   120

<210> SEQ ID NO 33
<211> LENGTH: 21
<212> TYPE: RNA
<213> ORGANISM: Homo sapiens

<400> SEQUENCE: 33
gccccaacaa ggaaggacaa g                                             21

<210> SEQ ID NO 34
<211> LENGTH: 22
<212> TYPE: RNA
<213> ORGANISM: Homo sapiens

<400> SEQUENCE: 34
gccccaacaa ggaaggacaa ga                                            22

<210> SEQ ID NO 35
<211> LENGTH: 20
<212> TYPE: RNA
<213> ORGANISM: Homo sapiens

<400> SEQUENCE: 35
gagagcaggg agcaggaagc                                               20

<210> SEQ ID NO 36
<211> LENGTH: 73
<212> TYPE: RNA
<213> ORGANISM: Homo sapiens

<400> SEQUENCE: 36
ggccgcgagg gagcgagagc agggagcagg aagcggggcc agcccgaccg ccgcgccccc    60
agcccccaca ggc                                                      73

<210> SEQ ID NO 37
<211> LENGTH: 14
<212> TYPE: RNA
<213> ORGANISM: Homo sapiens

<400> SEQUENCE: 37
```

```
gcccgaccgc cgcg                                                14

<210> SEQ ID NO 38
<211> LENGTH: 20
<212> TYPE: RNA
<213> ORGANISM: Homo sapiens

<400> SEQUENCE: 38
gagagcaggg agcaggaagc                                          20

<210> SEQ ID NO 39
<211> LENGTH: 19
<212> TYPE: RNA
<213> ORGANISM: Homo sapiens

<400> SEQUENCE: 39
gagagcaggg agcaggaag                                           19

<210> SEQ ID NO 40
<211> LENGTH: 18
<212> TYPE: RNA
<213> ORGANISM: Homo sapiens

<400> SEQUENCE: 40
gagagcaggg agcaggaa                                            18

<210> SEQ ID NO 41
<211> LENGTH: 17
<212> TYPE: RNA
<213> ORGANISM: Homo sapiens

<400> SEQUENCE: 41
gagagcaggg agcagga                                             17

<210> SEQ ID NO 42
<211> LENGTH: 18
<212> TYPE: DNA
<213> ORGANISM: Artificial sequence
<220> FEATURE:
<223> OTHER INFORMATION: Synthetic

<400> SEQUENCE: 42
ccctgctcca aaatcca                                             18

<210> SEQ ID NO 43
<211> LENGTH: 18
<212> TYPE: DNA
<213> ORGANISM: Artificial sequence
<220> FEATURE:
<223> OTHER INFORMATION: Synthetic

<400> SEQUENCE: 43 tggattttg gagcaggg                                             18

<210> SEQ ID NO 44
<211> LENGTH: 17
<212> TYPE: DNA
<213> ORGANISM: Artificial sequence
<220> FEATURE:
<223> OTHER INFORMATION: Synthetic

<400> SEQUENCE: 44
tggaggcccc agcgaga                                             17
```

```
<210> SEQ ID NO 45
<211> LENGTH: 17
<212> TYPE: DNA
<213> ORGANISM: Artificial sequence
<220> FEATURE:
<223> OTHER INFORMATION: Synthetic

<400> SEQUENCE: 45
tctcgctggg gcctcca                                                        17

<210> SEQ ID NO 46
<211> LENGTH: 22
<212> TYPE: DNA
<213> ORGANISM: Artificial sequence
<220> FEATURE:
<223> OTHER INFORMATION: Synthetic

<400> SEQUENCE: 46
aactcagtaa tggtaacggt tt                                                  22

<210> SEQ ID NO 47
<211> LENGTH: 22
<212> TYPE: DNA
<213> ORGANISM: Artificial sequence
<220> FEATURE:
<223> OTHER INFORMATION: Synthetic

<400> SEQUENCE: 47
aaaccgttac cattactgag tt                                                  22

<210> SEQ ID NO 48
<211> LENGTH: 22
<212> TYPE: DNA
<213> ORGANISM: Artificial sequence
<220> FEATURE:
<223> OTHER INFORMATION: Synthetic

<400> SEQUENCE: 48
cctgctccaa caaggaaaga ca                                                  22

<210> SEQ ID NO 49
<211> LENGTH: 22
<212> TYPE: DNA
<213> ORGANISM: Artificial sequence
<220> FEATURE:
<223> OTHER INFORMATION: Synthetic

<400> SEQUENCE: 49
tgtctttcct tgttggagca gg                                                  22

<210> SEQ ID NO 50
<211> LENGTH: 23
<212> TYPE: DNA
<213> ORGANISM: Artificial sequence
<220> FEATURE:
<223> OTHER INFORMATION: Synthetic

<400> SEQUENCE: 50
agcttcctgc tccctgctct aca                                                 23

<210> SEQ ID NO 51
<211> LENGTH: 23
<212> TYPE: DNA
<213> ORGANISM: Artificial sequence
<220> FEATURE:
<223> OTHER INFORMATION: Synthetic
```

<400> SEQUENCE: 51
tgtagagcag ggagcaggaa gct                                              23

<210> SEQ ID NO 52
<211> LENGTH: 188
<212> TYPE: DNA
<213> ORGANISM: Artificial sequence
<220> FEATURE:
<223> OTHER INFORMATION: Synthetic

<400> SEQUENCE: 52
gggtgcaccg ttcctggagg tactgcaata ccaggtcgat gcgtggagtg gacggagcaa      60
gctcctattc catctccctg ctccaaaaat ccatttaata tattgtcctc ggatagagga     120
cgtatcagat attaaactga taagaacaga tactacactt gatcttagcc aaaaggccga    180
gaagcgat                                                             188

<210> SEQ ID NO 53
<211> LENGTH: 188
<212> TYPE: DNA
<213> ORGANISM: Artificial sequence
<220> FEATURE:
<223> OTHER INFORMATION: Synthetic

<400> SEQUENCE: 53
atcgcttctc ggccttttgg ctaagatcaa gtgtagtatc tgttcttatc agtttaatat      60
ctgatacgtc ctctatccga ggacaatata ttaaatggat ttttggagca gggagatgga    120
ataggagctt gctccgtcca ctccacgcat cgacctggta ttgcagtacc tccaggaacg    180
gtgcaccc                                                             188

<210> SEQ ID NO 54
<211> LENGTH: 110
<212> TYPE: DNA
<213> ORGANISM: Artificial sequence
<220> FEATURE:
<223> OTHER INFORMATION: Synthetic

<400> SEQUENCE: 54
ctaataaagg actcttaatt catctcaaag tgtggtgttt tctctaacac ccctgggcac      60
aacattttgg aggccccagc gagatattaa caccaccgtg tgagatccgg               110

<210> SEQ ID NO 55
<211> LENGTH: 110
<212> TYPE: DNA
<213> ORGANISM: Artificial sequence
<220> FEATURE:
<223> OTHER INFORMATION: Synthetic

<400> SEQUENCE: 55
ccggatctca cacggtggtg ttaatatctc gctgggcct ccaaaatgtt gtgcccaggg       60
gtgttagaga aaacaccaca ctttgagatg aattaagagt cctttattag                110

<210> SEQ ID NO 56
<211> LENGTH: 72
<212> TYPE: DNA
<213> ORGANISM: Artificial sequence
<220> FEATURE:
<223> OTHER INFORMATION: Synthetic

<400> SEQUENCE: 56
tctgggtata gcaagagaac cattaccatt actaaactca gtaatggtaa cggtttcctt      60

```
gccattccca ag                                                          72

<210> SEQ ID NO 57
<211> LENGTH: 72
<212> TYPE: DNA
<213> ORGANISM: Artificial sequence
<220> FEATURE:
<223> OTHER INFORMATION: Synthetic

<400> SEQUENCE: 57
cttgggaatg gcaaggaaac cgttaccatt actgagttta gtaatggtaa tggttctctt      60
gctataccca ga                                                          72

<210> SEQ ID NO 58
<211> LENGTH: 121
<212> TYPE: DNA
<213> ORGANISM: Artificial sequence
<220> FEATURE:
<223> OTHER INFORMATION: Synthetic

<400> SEQUENCE: 58
ctgcggcaag tgcttctaca tccctgctcc aacaaggaaa gacaggaggc caggcgtgtg      60
tgtggctcac acctcttgtc cttccttgtt ggggcagggg tacagaagca ttttgggggg     120
c                                                                     121

<210> SEQ ID NO 59
<211> LENGTH: 121
<212> TYPE: DNA
<213> ORGANISM: Artificial sequence
<220> FEATURE:
<223> OTHER INFORMATION: Synthetic

<400> SEQUENCE: 59 gcccccaaa atgcttctgt accctgccc caacaaggaa ggacaagagg tgtgagccac         60
acacacgcct ggcctcctgt ctttccttgt tggagcaggg atgtagaagc acttgccgca     120
g                                                                     121

<210> SEQ ID NO 60
<211> LENGTH: 91
<212> TYPE: DNA
<213> ORGANISM: Artificial sequence
<220> FEATURE:
<223> OTHER INFORMATION: Synthetic

<400> SEQUENCE: 60
agcactgtga ggggctgggg gcagaacagg acaggtcagg gctggacaca cacagcttcc      60
tgctccctgc tctacagctc cctcgcaggc c                                     91

<210> SEQ ID NO 61
<211> LENGTH: 91
<212> TYPE: DNA
<213> ORGANISM: Artificial sequence
<220> FEATURE:
<223> OTHER INFORMATION: Synthetic

<400> SEQUENCE: 61
ggcctgcgag ggagctgtag agcagggagc aggaagctgt gtgtgtccag ccctgacctg      60
tcctgttctg cccccagccc ctcacagtgc t                                     91

<210> SEQ ID NO 62
```

```
<211> LENGTH: 15
<212> TYPE: DNA
<213> ORGANISM: Artificial sequence
<220> FEATURE:
<223> OTHER INFORMATION: Synthetic

<400> SEQUENCE: 62
ttgtaatacg actca                                                          15

<210> SEQ ID NO 63
<211> LENGTH: 19
<212> TYPE: DNA
<213> ORGANISM: Artificial sequence
<220> FEATURE:
<223> OTHER INFORMATION: Synthetic

<400> SEQUENCE: 63
tccctgatcc aaaaatcca                                                      19

<210> SEQ ID NO 64
<211> LENGTH: 22
<212> TYPE: RNA
<213> ORGANISM: Artificial sequence
<220> FEATURE:
<223> OTHER INFORMATION: Synthetic

<400> SEQUENCE: 64
cgcgcgucgc uuuaucuacu gu                                                  22

<210> SEQ ID NO 65
<211> LENGTH: 22
<212> TYPE: RNA
<213> ORGANISM: Artificial sequence
<220> FEATURE:
<223> OTHER INFORMATION: Synthetic

<400> SEQUENCE: 65
uuaucguucg auaagucgcg uu                                                  22

<210> SEQ ID NO 66
<211> LENGTH: 22
<212> TYPE: RNA
<213> ORGANISM: Artificial sequence
<220> FEATURE:
<223> OTHER INFORMATION: Synthetic

<400> SEQUENCE: 66
gaaguuacua uguaggcaac cu                                                  22

<210> SEQ ID NO 67
<211> LENGTH: 22
<212> TYPE: RNA
<213> ORGANISM: Artificial sequence
<220> FEATURE:
<223> OTHER INFORMATION: Synthetic

<400> SEQUENCE: 67
cgcgggacua auuguuaccg gg                                                  22

<210> SEQ ID NO 68
<211> LENGTH: 22
<212> TYPE: RNA
<213> ORGANISM: Artificial sequence
<220> FEATURE:
<223> OTHER INFORMATION: Synthetic

<400> SEQUENCE: 68
```
ucgcgucgaa cuccgcaacc ga                                          22

<210> SEQ ID NO 69
<211> LENGTH: 22
<212> TYPE: RNA
<213> ORGANISM: Artificial sequence
<220> FEATURE:
<223> OTHER INFORMATION: Synthetic

<400> SEQUENCE: 69
accgaacgcc guacccaucg gg                                          22

<210> SEQ ID NO 70
<211> LENGTH: 22
<212> TYPE: RNA
<213> ORGANISM: Artificial sequence
<220> FEATURE:
<223> OTHER INFORMATION: Synthetic

<400> SEQUENCE: 70
cgaggguaac gacucucgug uc                                          22

<210> SEQ ID NO 71
<211> LENGTH: 37
<212> TYPE: DNA
<213> ORGANISM: Artificial sequence
<220> FEATURE:
<223> OTHER INFORMATION: Synthetic

<400> SEQUENCE: 71
ttgtaatacg actcaacagt agataaagcg acgcgcg                          37

<210> SEQ ID NO 72
<211> LENGTH: 37
<212> TYPE: DNA
<213> ORGANISM: Artificial sequence
<220> FEATURE:
<223> OTHER INFORMATION: Synthetic

<400> SEQUENCE: 72
ttgtaatacg actcaaacgc gacttatcga acgataa                          37

<210> SEQ ID NO 73
<211> LENGTH: 37
<212> TYPE: DNA
<213> ORGANISM: Artificial sequence
<220> FEATURE:
<223> OTHER INFORMATION: Synthetic

<400> SEQUENCE: 73
ttgtaatacg actcaaggtt gcctacatag taacttc                          37

<210> SEQ ID NO 74
<211> LENGTH: 37
<212> TYPE: DNA
<213> ORGANISM: Artificial sequence
<220> FEATURE:
<223> OTHER INFORMATION: Synthetic

<400> SEQUENCE: 74
ttgtaatacg actcacccgg taacaattag tcccgcg                          37

<210> SEQ ID NO 75
<211> LENGTH: 37
<212> TYPE: DNA

```
<213> ORGANISM: Artificial sequence
<220> FEATURE:
<223> OTHER INFORMATION: Synthetic

<400> SEQUENCE: 75
ttgtaatacg actcatcggt tgcggagttc gacgcga                              37

<210> SEQ ID NO 76
<211> LENGTH: 37
<212> TYPE: DNA
<213> ORGANISM: Artificial sequence
<220> FEATURE:
<223> OTHER INFORMATION: Synthetic

<400> SEQUENCE: 76
ttgtaatacg actcacccga tgggtacggc gttcggt                              37

<210> SEQ ID NO 77
<211> LENGTH: 37
<212> TYPE: DNA
<213> ORGANISM: Artificial sequence
<220> FEATURE:
<223> OTHER INFORMATION: Synthetic

<400> SEQUENCE: 77
ttgtaatacg actcagacac gagagtcgtt accctcg                              37

<210> SEQ ID NO 78
<211> LENGTH: 37
<212> TYPE: DNA
<213> ORGANISM: Artificial sequence
<220> FEATURE:
<223> OTHER INFORMATION: Synthetic

<400> SEQUENCE: 78
ttgtaatacg actcacccgg taacaattag acccgcg                              37

<210> SEQ ID NO 79
<211> LENGTH: 13
<212> TYPE: RNA
<213> ORGANISM: Homo sapiens

<400> SEQUENCE: 79
gcccgaccgc cgc                                                        13

<210> SEQ ID NO 80
<211> LENGTH: 22
<212> TYPE: RNA
<213> ORGANISM: Homo sapiens

<400> SEQUENCE: 80
uccugucuuu ccuuguugga gc                                              22

<210> SEQ ID NO 81
<211> LENGTH: 22
<212> TYPE: DNA
<213> ORGANISM: Artificial sequence
<220> FEATURE:
<223> OTHER INFORMATION: Synthetic

<400> SEQUENCE: 81
gctccaacaa ggaaagacag ga                                              22

<210> SEQ ID NO 82
<211> LENGTH: 22
```

```
<212> TYPE: DNA
<213> ORGANISM: Artificial sequence
<220> FEATURE:
<223> OTHER INFORMATION: Synthetic

<400> SEQUENCE: 82
tcctgtcttt ccttgttgga gc                                           22
```